United States Patent [19]

Hutchinson et al.

[11] Patent Number: 5,202,321
[45] Date of Patent: Apr. 13, 1993

[54] THIOPYRANO(2,3,4-C,D)INDOLES AS INHIBITORS OF LEUKOTRIENE BIOSYNTHESIS

[75] Inventors: John H. Hutchinson, Montreal; Yves Girard, Bizard; Rejean Fortin, Montreal Nord; Dwight MacDonald, Ile Bizard; John Scheigetz, Dollard des Ormeaux; Daniel Delorme, St. Lazare; Michel Therien, Laval; Pierre Hamel, Vimont, all of Canada

[73] Assignee: Merck Frosst Canada, Inc., Kirkland, Canada

[21] Appl. No.: 714,478

[22] Filed: Jun. 13, 1991

[51] Int. Cl.$^5$ .................. C07D 401/00; A61K 31/54
[52] U.S. Cl. .................. 514/727.5; 514/237.8; 514/253; 514/321; 514/338; 514/411; 514/826; 514/886; 544/60; 544/111; 544/372; 546/189; 546/194; 546/198; 548/431; 548/436
[58] Field of Search .............. 546/270, 198, 189, 194; 548/431, 436; 514/338, 411, 826, 886, 227.5, 237.8, 321, 253; 544/60, 111, 372

[56] References Cited

U.S. PATENT DOCUMENTS 5,021,420  6/1991  Comte et al. .................. 514/338

FOREIGN PATENT DOCUMENTS 0030979  3/1981  Japan .................. 514/411

Primary Examiner—C. Warren Ivy
Assistant Examiner—Raymond Covington
Attorney, Agent, or Firm—Gabriel Lopez; Joseph F. DiPrima

[57] ABSTRACT

Compounds having the formula I:

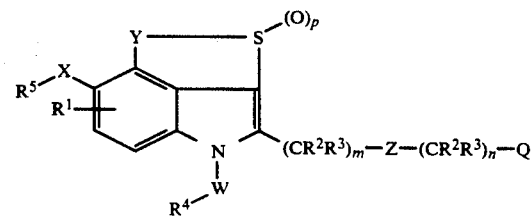

are inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, psoriasis, uveitis and allograft rejection and in preventing the formation of atherosclerotic plaques.

15 Claims, No Drawings

THIOPYRANO(2,3,4-C,D)INDOLES AS INHIBITORS OF LEUKOTRIENE BIOSYNTHESIS

BACKGROUND OF THE INVENTION

The leukotrienes constitute a group of locally acting hormones, produced in living systems from arachidonic acid. The major leukotrienes are Leukotriene $B_4$ (abbreviated as $LTB_4$), $LTC_4$, $LTD_4$ and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

The ring system of the compounds of the present invention, thiopyrano[2,3,4-c,d]indole, is novel; that is, it has not been described in the prior art. A few derivatives of the natural product chuangxinmycin, which contains the thiopyrano [4,3,2-c,d]indole ring system, have been described as showing antibiotic and anticancer utilities. However, in addition to being isomeric with the present ring system, the substitution pattern is very different. The compounds of the present invention have complex substituents at positions 2 and 6, whereas such substitution is for the most part absent or very simple in the thiopyrano[4,3,2-c,d]indoles described. The following structures and references are illustrative of the compounds in the prior art.

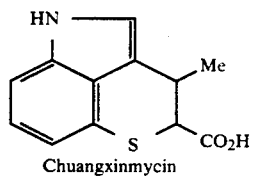

Chuangxinmycin

Kozikowski, et al.,
J. Am. Chem. Soc.,
104, 7622-26, 1982.
and Matsumoto, et al.
Japan Kokai Tokkyo
Koho 63-216890

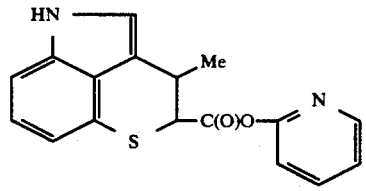

Chuangxinmycin 2-pyridinyl ester

Su, et al., Yiyao
Gougye, pp. 17-21,
1984 [Chem. Abst.
Vol. 101, No. 72492]

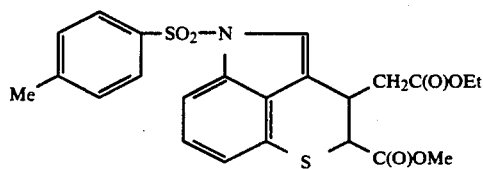

Matsumoto, et
al., Japan Kokai
Tokkyo Koho,
63-277683

SUMMARY OF THE INVENTION

The present invention relates to certain thiopyrano[2,3,4-c,d]indoles having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, psoriasis, uveitis and allograft rejection and in preventing the formation of atherosclerotic plaques.

DETAILED DESCRIPTION OF THE INVENTION

The present invention provides novel compounds of the Formula I:

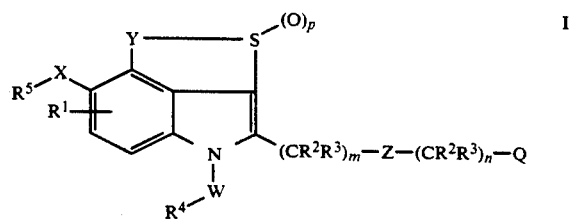

wherein:

$R^1$ is H, lower alkyl, cycloalkyl, lower alkoxy, perhalo lower alkenyl, CN, $NO_2$, $CF_3$, $N_3$, $N(R^6)_2$, $NR^6COR^7$, $NR^6CON(R^6)_2$, $OR^6$, $SR^8$, $S(O)R^8$, $S(O)_2R^8$, $S(O)_2N(R^6)_2$, $COR^7$, $CON(R^6)_2$, $CO_2R^9$, or halogen;

$R^2$ is H, lower alkyl, hydroxy, or lower alkoxy, or two $R^2$ groups on adjacent carbon atoms may be a bond;

$R^3$ is H or lower alkyl;

$R^2$ and $R^3$ on the same carbon atom may be a double-bonded oxygen (=O);

$R^4$ is H, [aryl($R^{10})_2]_t$, lower alkyl, alkyl, cycloalkyl, lower alkenyl, phenyl lower alkenyl, perhalophenyl, or substituted lower alkyl wherein the substituent is [aryl($R^{10})_2]_t$, phenoxy, or N-morpholino;

$R^5$ is alkyl, cycloalkyl, aryl($R^{10})_2$, $CONR^6R^{11}$, substituted lower alkyl wherein the substituent is [aryl($R^{10})_2]_t$, or substituted tetrahydropyridyl wherein the substituent is phenyl or lower alkyl;

$R^6$ is H or lower alkyl, or two $R^6$ groups attached to the same nitrogen may form a saturated ring of 5 or 6 members, optionally containing a second heteroatom chosen from O, S, or $NR^2$;

$R^7$ is H, lower alkyl, phenyl, p-tolyl, or $CF_3$;

$R^8$ is lower alkyl, phenyl, p-tolyl, or $CF_3$;

$R^9$ is H, lower alkyl, or benzyl;

$R^{10}$ is H, lower alkyl, cycloalkyl, lower alkoxy, benzyl, benzyloxy, perhalo lower alkenyl, CN, $NO_2$, $CF_3$, $N_3$, $N(R^6)_2$, $NR^6COR^7$, $NR^6CON(R^6)_2$, $OR^6$, $SR^8$, $S(O)R^8$, $S(O)_2R^8$, $S(O)_2N(R^6)_2$, $COR^7$, $CON(R^6)_2$, $CO_2R^9$, halogen, hydroxy- or lower alkoxy-tetrahydropyranyl, or 1-hydroxy- or 1-lower alkoxy-1-thiazol-2,4, or 5-yl lower alkyl;

$R^{11}$ is $R^{10}$-phenyl lower alkyl;
$R^{12}$ is H or lower alkyl;
$R^{13}$ is H or lower alkyl;
$R^{14}$ is lower alkyl, $R^{10}$-phenyl, $CF_3$, or $N(R^6)_2$;
$R^{15}$ is $CO_2H$, $N(R^6)_2$, or $NHCOR^7$;
$R^{16}$ is $-(CH_2)_s-C(R^{17})_2-(CH_2)_s-R^{18}$ or $-CH_2CON(R^{20})_2$;
$R^{17}$ is H or lower alkyl;
$R^{18}$ is
  a) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
  b) the radical $V-R^{19}$;

$R^{19}$ contains up to 20 carbon atoms and is (1) an alkyl group or (2) an alkyl carbonyl group of an organic acyclic or monocyclic carboxylic acid containing not more than 1 heteroatom in the ring;

$R^{20}$ is H or lower alkyl or 2 $R^{20}$ groups attached to the same nitrogen may form a saturated ring of 5 or 6 members, optionally containing a second heteroatom chosen from O, S, or $NR^2$;

$R^{21}$ is H, lower alkyl, lower alkylcarbonyl, or lower alkylsulfonyl;

Q is $CO_2R^9$, $CN_4H$, $-OH$, $-CH_2OH$, $-CHO$, $-CON(R^6)_2$, $-CON(OH)R^6$, $-CONHS(O)_2R^{14}$, $-COCN_4H$, $-CONR^6(CH_2)_rR^{15}$, $-N(R^6)_2$, $-NHCOR^7$, $-NHS(O)_2R^{14}$, $-NHCOCO_2R^9$, $-CO_2R^{16}$, $-CONHCN$, or $-CONHCN_4H$;

U is $CH_2$, O, or S;
V is O, S, or $NR^9$;
W is $CH_2$ or CO, or $S(O)_2$ when $R^4$ is not H;
X is $(CH_2)_qU-$, $-U(CH_2)_q-$, $-CH=CH-$, or $-CH_2OCH_2-$;
Y is $-CH_2C(R^{12})_2-$, $-CH=CR^{13}-$, $-CH_2=CHCH_2-$, or $-(CH_2)_3-$;
Z is a bond, O, S, $NR^{21}$, or $CONR^9$;
m is 0 to 3;
n is 1 to 3 when Z is O, S, $NR^{21}$, or $CONR^9$;
n is 0 to 3 when Z is a bond;
p is 0 to 2;
q is 0 to 3;
r is 1 to 3;
s is 0 or 1;
t is 1 or 2;
aryl is phenyl, pyridinyl, quinolinyl, isoquinolinyl, thiazolyl, thienyl, oxazolyl, pyrimidinyl, pyrazinyl, furopyridinyl, naphthyl, 1,8-naphthyridinyl, or methylenedioxyphenyl, or the N-oxides thereof;
or a pharmaceutically acceptable salt thereof.

A preferred embodiment of the present invention is represented by Formula Ia:

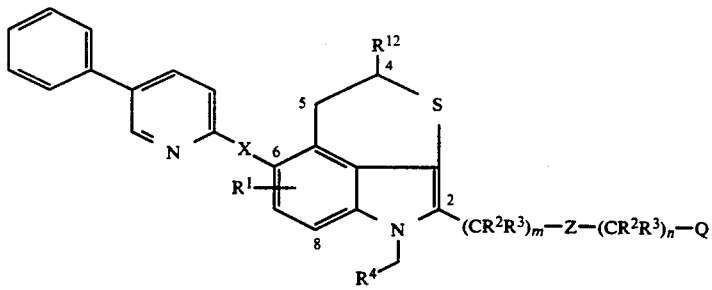

Ia wherein:
$R^1$ is H, lower alkyl, or halogen;
$R^4$ is alkyl, cycloalkyl, $[aryl(R^{10})_2]_t$, or substituted lower alkyl wherein the substituent is $[aryl(R^{10})_2]_t$;
$R^{10}$ is H or lower alkyl;
Q is $-CO_2H$, $CN_4H$, or $-CONHS(O)_2R^{14}$;
q is 1;
and the remaining substituents are as defined for Formula I.

Definitions

The following abbreviations have the indicated meanings:

| | |
|---|---|
| Ac = | acetyl |
| Ada = | adamantyl |
| Bz = | benzyl |
| c-Bu = | cyclobutyl |
| c-Pen = | cyclopentyl |
| c-Pr = | cyclopropyl |
| c-Hex = | cyclohexyl |
| DMAP = | 4-(dimethylamino)pyridine |
| DMF = | dimethylformamide |
| DMSO = | dimethyl sulfoxide |
| Et = | ethyl |
| $Et_3N$ = | triethylamine |
| Fur = | furandiyl |
| HMPA = | hexamethylphosphorictriamide |
| i-Bu = | isobutyl |
| i-Pr = | isopropyl |
| KHMDS = | potassium hexamethyldisilazide |
| LDA = | lithium diisopropylamide |
| Me = | methyl |
| n-Bu = | normal butyl |
| n-Pr = | normal propyl |
| Ph = | phenyl |
| Phe = | benzenediyl |
| psi = | pounds per square inch |
| Pye = | pyridinediyl |
| r.t. = | room temperature |
| t-Bu, t-butyl = | tertiary butyl |
| Th = | 2- or 3-thienyl |
| THF = | tetrahydrofuran |
| Thi = | thiophenediyl |
| TLC = | thin layer chromatography |
| Triton B = | benzyltrimethylammonium hydroxide |
| $CN_4H$ = | 1H (or 2H)-tetrazol-5-yl |
| $C_3H_5$ = | allyl |

Alkyl means linear and branched structures, and combinations thereof.

"Alkyl" means "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

"Lower alkyl" means alkyl groups of from 1 to 7 carbon atoms. Examples of lower alkyl groups include methyl, ethyl, propyl, isopropyl, butyl, sec- and tert-butyl, pentyl, hexyl, heptyl, and the like.

"Cycloalkyl" means a hydrocarbon containing one or more rings having from 3 to 12 carbon atoms, with the hydrocarbon having up to a total of 20 carbon atoms. Examples of cycloalkyl groups are cyclopropyl, cyclopentyl, cycloheptyl, adamantyl, cyclododecylmethyl, 2-ethyl-1-bicyclo[4.4.0]decyl and the like.

"Lower alkenyl" means alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl and the like.

"Lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Alkylcarbonyl" means alkylcarbonyl groups of 1 to 20 carbon atoms of a straight, branched or cyclic configuration. Examples of alkylcarbonyl groups are 2-methylbutanoyl, octadecanoyl, 11-cyclohexylundecanoyl and the like. Thus, the 11-cyclohexylundecanoyl group is c-Hex-$(CH_2)_{10}$—C(O)—.

"Lower alkylcarbonyl" means alkylcarbonyl groups of from 1 to 8 carbon atoms of a straight, branched, or cyclic configuration. Examples of lower alkylcarbonyl group are formyl, 2-methylbutanoyl, cyclohexylacetyl, etc. By way of illustration, the 2-methylbutanoyl groups signifies —COCH($CH_3$)$CH_2CH_3$.

"Lower alkylsulfonyl" means alkylsulfonyl groups of from 1 to 7 carbon atoms of a straight, branched, or cyclic configuration. Examples of lower alkylsulfonyl groups are methylsulfonyl, 2-butylsulfonyl, cyclohexylmethylsulfonyl, etc. By way of illustration, the 2-butylsulfonyl group signifies —S(O)$_2$CH($CH_3$)$CH_2CH_3$.

Halogen means F, Cl, Br, and I.

It is intended that the definitions of any substituent (e.g., $R^1$, $R^2$, $R^6$, etc.) in a particular molecule be independent of its definitions elsewhere in the molecule. Thus, N($R^6$)$_2$ represents —NHH, —NHMe, —N(Me)(Et), etc.

The heterocycles formed when two $R^6$ (or $R^{20}$) groups join through N include pyrrolidine, piperidine, morpholine, thiamorpholine, piperazine, and N-methylpiperazine.

The prodrug esters of Q (i.e., when Q=$CO_2R^{16}$) are intended to include the esters such as are described by Saari et al., J. Med. Chem., 21, No. 8, 746–753 (1978), Sakamoto et al., Chem. Pharm. Bull., 32, No. 6, 2241–2248 (1984) and Bundgaard et al., J. Med. Chem., 30, No. 3, 451–454 (1987). Within the definition of $R^{18}$, some representative monocyclic or bicyclic heterocyclic radicals are:
2,5-dioxo-1-pyrrolidinyl,
(3-pyridinylcarbonyl)amino,
1,3-dihydro-1,3-dioxo-2H-isoindol-2-yl,
1,3-dihydro-2H-isoindol-2-yl,
2,4-imidazolinedion-1-yl,
2,6-piperidinedion-1-yl,
2-imidazolyl,
2-oxo-1,3-dioxolen-4-yl,
piperidin-1-yl,
morpholin-1-yl, and
piperazin-1-yl.

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N$^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Mixed salts may at times be advantageous. For example the sodium salt of certain examples of compound I when mixed with an equivalent amount of tromethamine yields a more soluble salt form of I.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

Utilities

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, and 16) metastasis of tumors.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001-1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

Combinations with other drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the oxicams; and
(5) the biphenylcarboxylic acid derivatives;
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, sulindac, tiopinac, tolmetin, zidometacin and zomepirac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

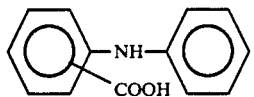

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

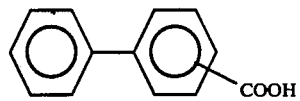

which can bear a variety of substituents and in which the free —COOH group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

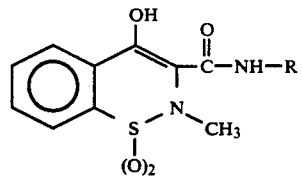

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac and tolmetin. Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$- or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126-131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Compounds of the formula I of the present invention may be prepared according to the synthetic routes outlined in the Schemes I to XII and by following the methods described herein.

Following the schemata, Table A provides alkylating agents, $R^4CH_2X^1$ and $R^5CH_2X^1$, as well as their literature or commercial sources. Tables 1-4 illustrate compounds representative of the present invention.

SCHEME I

The indole intermediate VI of Scheme I may be prepared by a Fischer-Indole condensation between ketone III and the 4-allyloxyphenyl hydrazine II in an organic solvent such as toluene with an organic acid such as acetic acid buffered with sodium acetate. Alternatively, the indole VI may be prepared by a Fischer-Indole condensation in the above manner but using a 4-methoxyphenylhydrazine II and the same ketone III to provide the intermediate IV. Demethylation of indole IV using, for example, lithium t-butyl thiolate in hot HMPA affords the phenol V which may then be treated with allylbromide using an organic solvent (e.g., DMF) and an inorganic base such as sodium hydride to give the indole intermediate VI. The indole VI may then be heated in a high boiling organic solvent e.g. 1,2-dichlorobenzene to affect a Claisen rearrangement to produce a 4-allyl-5-hydroxy substituted indole. Addition of an organic acid such as p-toluenesulfonic acid to the reaction mixture promotes the cyclisation and thus yields the thiopyranoindole intermediate VII. Coupling of the phenol VII with an alkylating agent $R^5CH_2X^1$, typified by 5-phenyl-2-picolyl chloride in an organic solvent (e.g., DMF) using an inorganic base (e.g., sodium hydride) provides the thiopyranoindole intermediate VIII where $R^5$ corresponds to 5-phenylpyridin-2-yl. Saponification of the ester of compound VIII using, for example, lithium hydroxide in aqueous methanol/tetrahydrofuran yields IA; both VIII and IA are examples of compound I of the present invention.

SCHEME I
PREPARATION OF FORMULA I COMPOUNDS

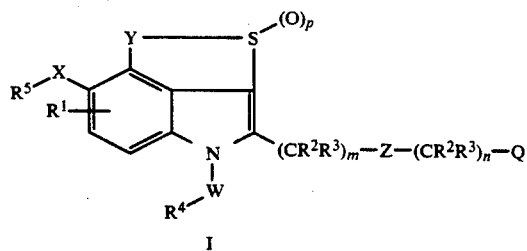

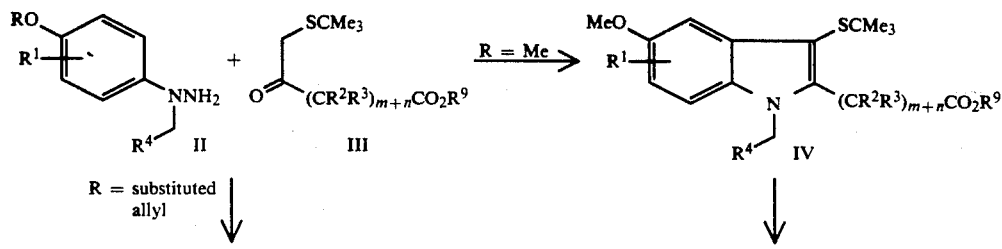

SCHEME I
PREPARATION OF FORMULA 1 COMPOUNDS

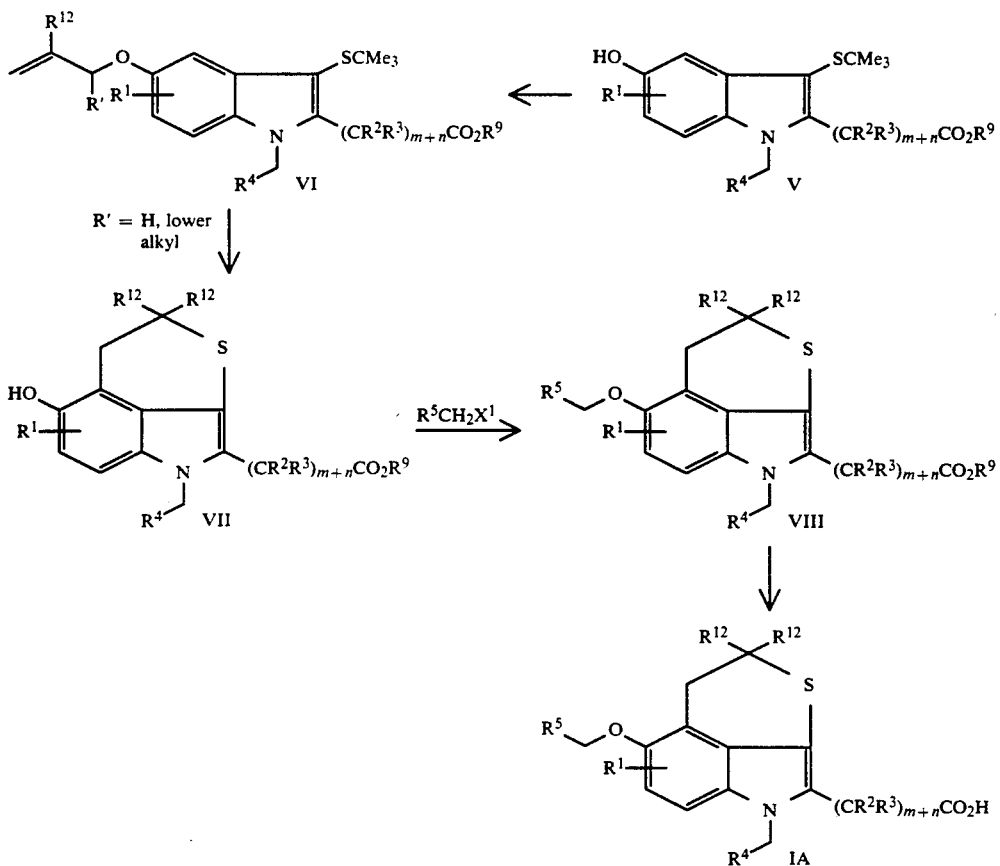

SCHEME II

Scheme II describes an alternative route for the synthesis of compounds of formula IA. In this case, the ketone III is condensed with a 4-methoxyphenylhydrazine in an alcohol solvent such as 2-methyl-2-propanol to provide the indole IX. Treatment of compound IX with molten pyridine hydrochloride leads to demethylation and lactamisation resulting in the formation of the indole X. Conversion of the indole X to the thiopyranoindole XIII via the allyl ether XI and the tetracycle XII may be achieved following the procedures previously described in Scheme I. Cleavage of the lactam ring of compound XIII may be achieved by stirring the lactam XIII in an organic solvent (e.g., THF) with an inorganic base such as lithium hydroxide to yield the indole acid XIV. Direct conversion of intermediate XIV to compounds of formula IA can be done by treatment of the indole-acid XIV with an inorganic base in an appropriate organic solvent (e.g., sodium hydride in appropriate organic solvent (e.g., sodium hydride in DMF) and subsequent reaction with an alkylating agent $R^4CH_2X^1$.

Using the above procedure but allowing a longer time for reaction, the indole acid XIV may be converted to the indole-ester XV which may then be saponified (using, for example, lithium hydroxide in aqueous methanol/THF) to provide the afore-mentioned acid corresponding to formula IA. In certain cases, reaction of the indole-acid XIV under the conditions described will produce as an additional product the ester XVI or the acid derived from ester XVI.

SCHEME II
ALTERNATIVE PREPARATION OF FORMULA IA COMPOUNDS

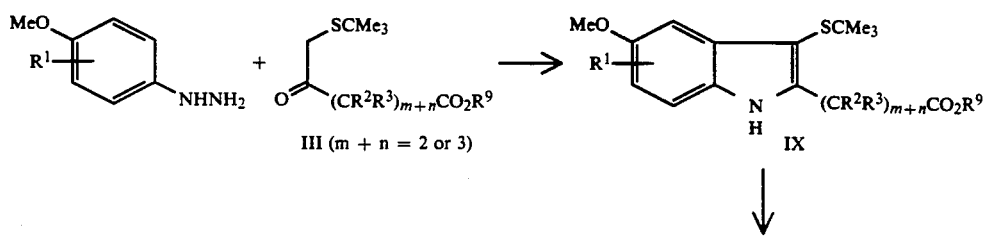

SCHEME II
ALTERNATIVE PREPARATION OF FORMULA IA COMPOUNDS

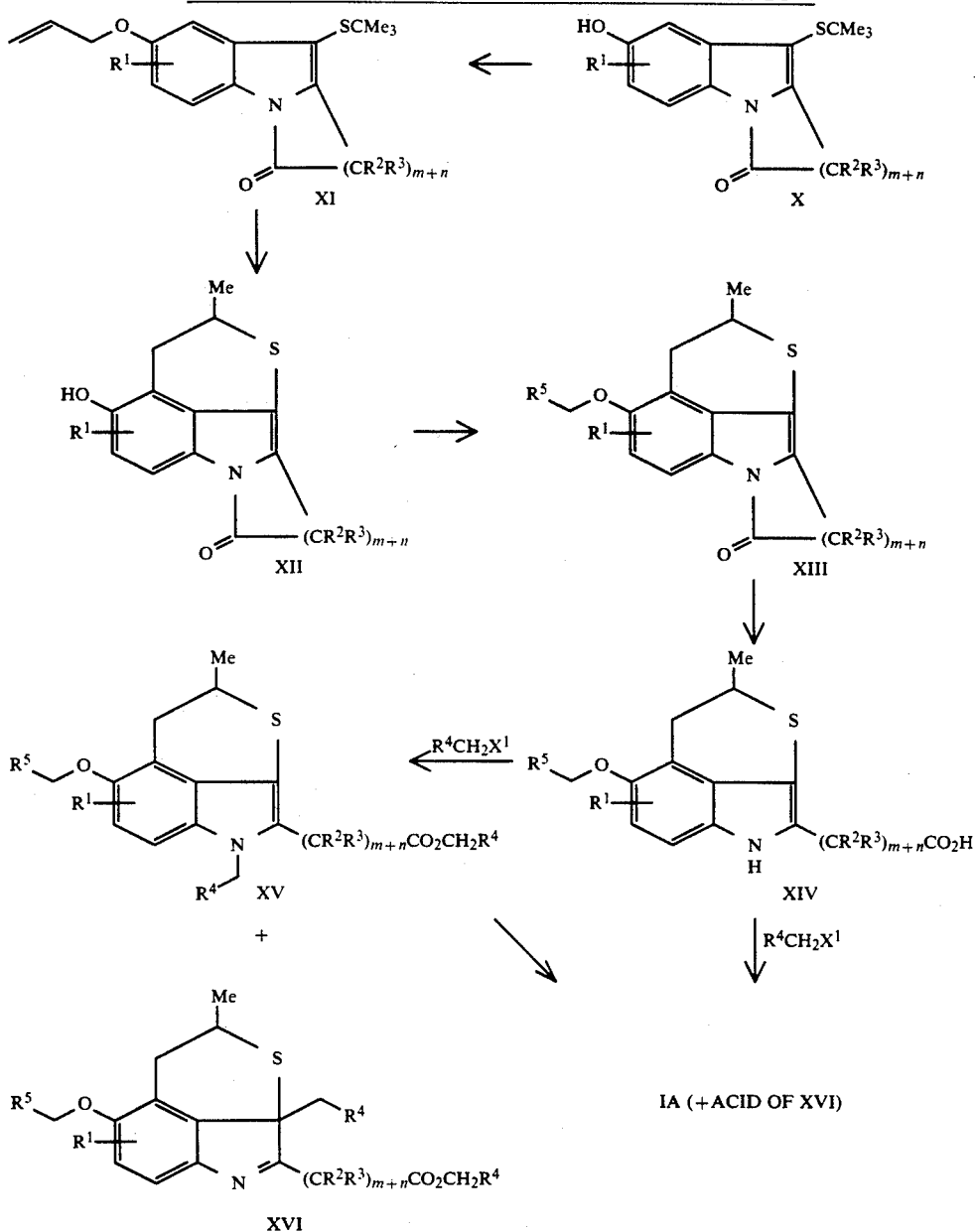

SCHEME III

Alternative methods for the preparation of formula VII compounds are shown in Scheme III. The intermediate indole IV (from Scheme I) on reaction with ethanethiol and $AlCl_3$ in an organic solvent such as dichloromethane leads to the production of the 5-hydroxyindole XIX ($R^9$=H). Compound XIX ($R^9$=H) can be esterified by treatment with ethereal diazomethane to provide the indole XIX where $R^9$=Me. Reaction of indole XIX ($R^9$=Me) with a premixed solution of dimethyl dithioacetate and sulfuryl chloride in a solvent such as 1,2-dichloroethane results in the formation of the intermediate diester XX. This diester XX may be monosaponified (lithium hydroxide in aqueous methanol) and the acid reduced using, for example, diborane in THF to yield the alcohol XXI. Oxidation of the alcohol XXI results in the formation of the aldehyde intermediate XXII. This transformation may be accomplished by adding the alcohol XXI to a cold, premixed solution of oxalyl chloride and DMSO in dichloromethane. After a short time an organic base such as triethylamine is added. Quenching the mixture by addition of ether followed by acidification and isolation of the organic phase gives the aldehyde XXII. Formation of the thiopyranoindole VII may be achieved by reaction of the aldehyde XXII with phenylboric acid and propionic acid in an organic solvent such as benzene. Isolation and reduction of the crude product using, for example, triethylsilane and boron trifluoride etherate in 1,2-dichloroethane provides the thiopyranoindole VII ($R^{12}$=$R^{12}$=H).

An alternative route to formula VII compounds commences with the indole intermediate V which, on treatment with an inorganic base such as potassium hydride in an organic solvent (e.g., p-xylene) followed by addition of zinc chloride and an alkenylhalide such as crotyl bromide gives as a product the indole XVII. A second product, the intermediate XVIII, which is the result of alkylation of the phenolic oxygen, is also isolated. The indole XVII can be converted to the thiopyranoindole VII by heating in an organic solvent for example 1,2-dichlorobenzene in the presence of an organic acid like p-toluenesulfonic acid.

ethylene glycol) provides the acid derivative IB, another representative of compound I.

The nitrile intermediate XXV may be prepared from the thiopyranoindole VII by initially converting the phenol to the t-butyldimethylsilyl ether derivative XXVI using t-butyldimethylsilyl chloride with an organic base, for example triethylamine, and an appropriate solvent e.g. dichloromethane. The intermediate XXVI may then be transformed to the nitrile XXIX via the alcohol XXVII and the mesylate XXVIII using the protocol described above. Removal of the silyl ether of intermediate XXIX is achieved using a source of fluo-

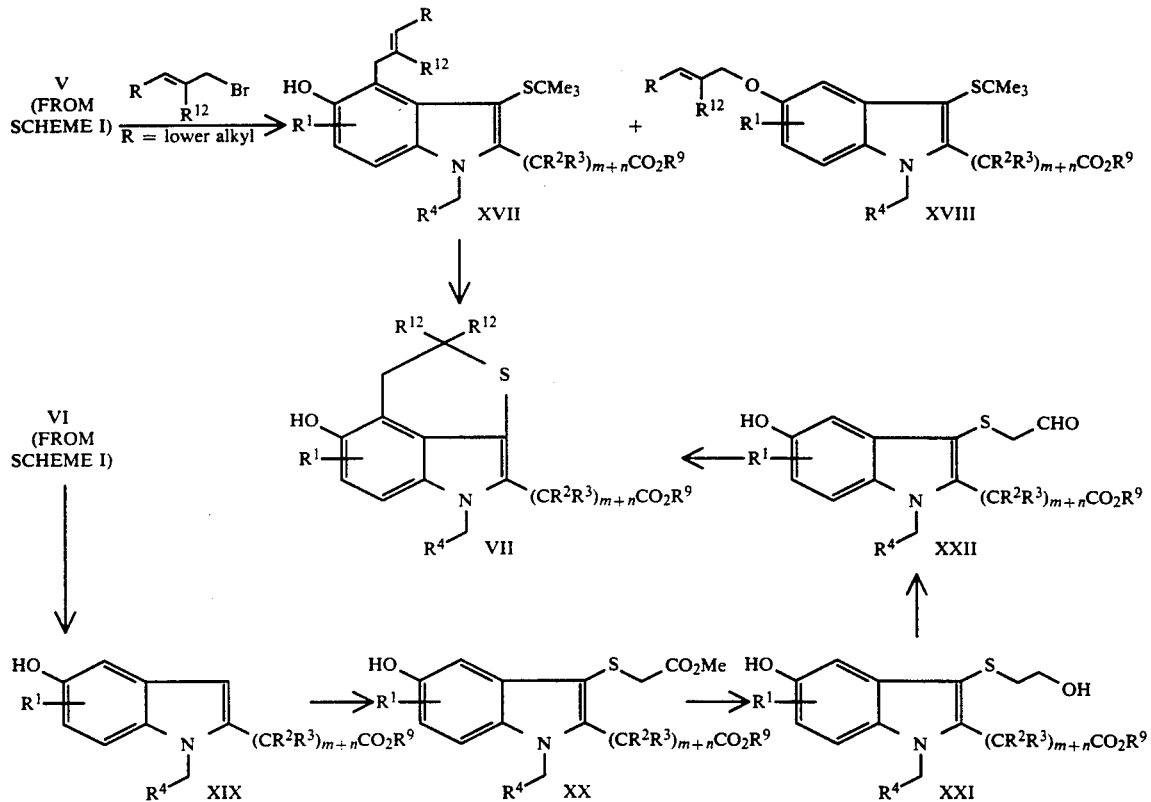

SCHEME III
ALTERNATIVE PREPARATION OF FORMULA VII COMPOUNDS

SCHEME IV

Scheme IV illustrates further methods for the preparation of formula I compounds. For example, the intermediate VIII (from Scheme I) may be reduced using an inorganic hydride such as lithium aluminum hydride in an organic solvent such as THF to give the alcohol XXIII, which is a representative of Formula I. Reaction of the alcohol XXIII with methane sulfonyl chloride in an organic solvent (e.g., THF) in the presence of an organic base, such as triethylamine, gives rise to the mesylate XXIV. The mesylate group of intermediate XXIV may be displaced by cyanide ion (sodium cyanide in an organic solvent such as DMF or DMSO) to yield the nitrile XXV. The nitrile XXV on heating in a high boiling organic solvent such as 1,2-dichlorobenzene with tri-n-butyltin azide affords the tetrazole derivative IC, a representative of compound I.

Alternatively, hydrolysis of the nitrile XXV using an inorganic base such as potassium hydroxide in a high boiling alcoholic solvent (e.g., 2-methoxyethanol and ride ion such as tetrabutylammonium fluoride in an organic solvent (e.g., THF) to afford the phenol XXX. The phenol XXX may then be reacted with an appropriate alkylating agent ($R^5CH_2X^1$) using conditions previously described in Scheme 1 to give the intermediate nitrile XXV.

SCHEME IV
PREPARATION OF FURTHER COMPOUNDS OF
FORMULA I

WHEREIN: W = —CH$_2$—
X = —CH$_2$O—
Y = —CH$_2$C(R$^{12}$)$_2$—
Z = a bond
p = 0
Q = —CO$_2$H, -TETRAZOL-5-YL

-continued
SCHEME IV
PREPARATION OF FURTHER COMPOUNDS OF FORMULA I

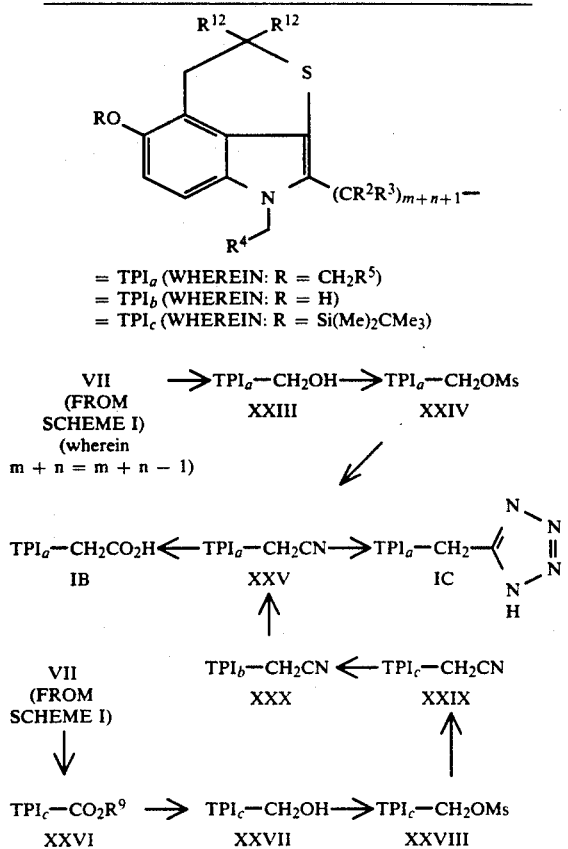

= TPI$_a$ (WHEREIN: R = CH$_2$R$^5$)
= TPI$_b$ (WHEREIN: R = H)
= TPI$_c$ (WHEREIN: R = Si(Me)$_2$CMe$_3$)

reduced to the alcohol XXXI using, for example, lithium aluminum hydride in an organic solvent such as THF. Treatment of a solution of the alcohol XXXI in DMSO (or another appropriate organic solvent) with an inorganic base (e.g., sodium hydride) and an α-bromoester such as ethyl 2-bromopropanoate provides the ester XXXII (an example of Formula I) which upon hydrolysis under standard conditions affords compounds I corresponding to formula ID. Alternatively, the ester XXXII can be transformed into the nitrile XXXIII in a two step process. Firstly, the ester is reacted with dimethylaluminum amide in refluxing xylene and then the amide produced can be dehydrated using, for example, trifluoroacetic anhydride in pyridine. The product, nitrile XXXIII, may then be reacted with tri-n-butyltin azide in 1,2-dichlorobenzene to give the tetrazole IE. The reaction of the alcohol XXXI with an acrylonitrile in an organic solvent such as THF in the presence of a base (e.g., Triton B) provides nitriles of formula XXXIII where n=2.

For the alcohol of formula XXXI where m=1, brief treatment of the alcohol in an organic solvent (for example 1,2-dichloroethane) with boron trifluoride etherate and an appropriate thiol acid derivative leads to compounds of formula XXXV (an example of Formula I) which contain a sulfur atom in the C-2 side chain. Where the thiol contains an acid functionality formula IF compounds are produced directly. If the thiol contains an ester, the product (which corresponds to the ester XXXV) may be subsequently hydrolysed using conditions previously described to provide the acid of formula IF. In the case where the alcohol XXXI has m>1, a sulfur containing side chain may be incorporated by initially converting the alcohol to the tosylate XXXIV (using p-toluenesulfonyl chloride and an organic base such as pyridine) and then displacement of the tosylate group using, for example, a sodium thiolate in an organic solvent such as DMF. The product resulting from this sequence of reactions, the ester XXXV may be converted to the nitrile XXXVI and then the tetrazole IG, following the procedures described above.

SCHEME V

The preparation of formula I compounds containing heteroatoms in the C-2 side chain is depicted in Scheme V. The thiopyranoindole VIII (from Scheme I) may be

SCHEME V
PREPARATION OF FORMULA I COMPOUNDS

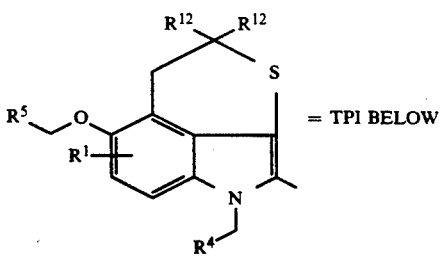 = TPI BELOW

WHEREIN: W = —CH$_2$—
X = —CH$_2$O—
Y = —CH$_2$C(R$^{12}$)$_2$—
Z = O, S
p = 0
Q = —CO$_2$H, -TETRAZOL-5-YL

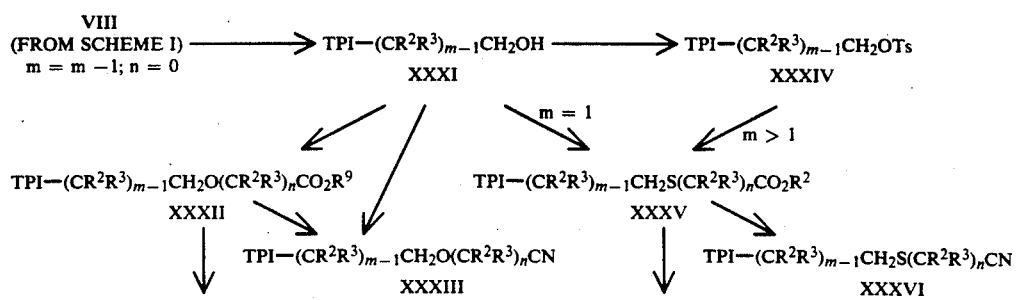

SCHEME V
PREPARATION OF FORMULA I COMPOUNDS

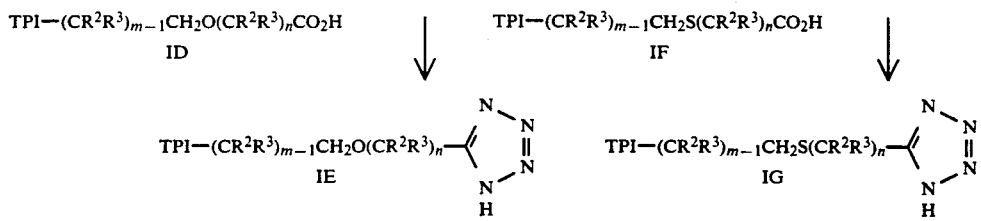

SCHEME VI

Sulfones and sulfoxides corresponding to compounds of formula I may be prepared according to the routes described in Scheme VI. The phenol VII (Scheme I) can be acetylated using, for example, acetyl chloride or acetic anhydride and an organic base such as pyridine in an organic solvent such as dichloromethane. The acetylated phenol, intermediate XXXVII, on treatment with a peracid (e.g., m-chloroperoxybenzoic acid) in an organic solvent such as dichloromethane affords the intermediate XXXVIII. When two equivalents of peracid are used, the product is the sulfone XXXVIII where p=2. But, when one equivalent of peracid is used the major products are the diastereomeric sulfoxides XXXVIII (if XXXVII contains an asymmetric centre) where p=1. These diastereomers can be separated by column chromatography on silica gel.

Removal of the acetate of the intermediate XXXVIII (p=1 or 2) using potassium carbonate in methanol provides the phenol XXXIX. The phenol XXXIX can be converted to the intermediate XL and then to the compound of formula IH using the procedures described in Scheme I.

Applying the above chemistry to intermediate XXX, the sulfoxides and sulfones of tetrazole IC can be prepared. Substituting XL for VIII in Scheme V allows the preparation of the sulfoxides and sulfones of ID-G.

SCHEME VI
PREPARATION OF SULFOXIDES AND SULFONES OF FORMULA I COMPOUNDS

WHEREIN: W = —CH$_2$—
X = —CH$_2$O—
Y = —CH$_2$C(R$^{12}$)$_2$—
Z = a bond
p = 1, 2
Q = —CO$_2$H

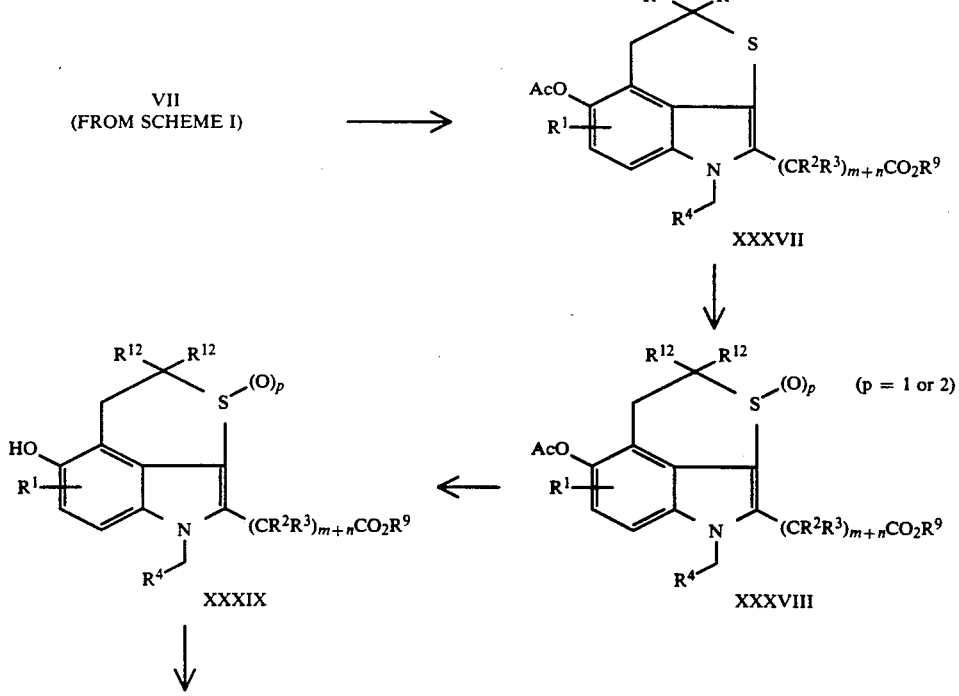

-continued
SCHEME VI
PREPARATION OF SULFOXIDES AND SULFONES OF FORMULA I COMPOUNDS

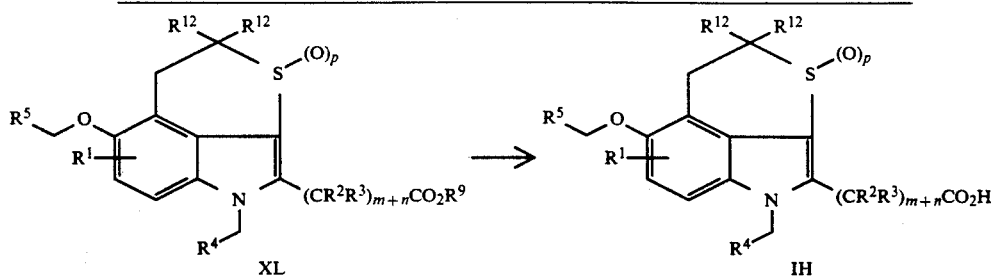

SCHEME VII

The synthesis of formula I compounds containing a seven-membered sulfur heterocycle is shown in Scheme VII. The indole XIX (Scheme III) on treatment with a premixed solution of sulfuryl chloride and 3,3'-dithiodipropionaldehyde in an organic solvent such as 1,2-dichloroethane provides the 3-substituted indole XLI. On stirring the indole XLI in an organic solvent (e.g., ether) saturated with gaseous HCl the tricyclic intermediate XLII is produced. Using the procedures described in Scheme I, the phenol of intermediate XLII may be coupled with $R^5CH_2X^1$ to afford the ester XLIII. Hydrolysis as before then provides the acid corresponding to formula IJ. The tricyclic intermediate XLII may also be hydrogenated using a catalyst such as 10% palladium on carbon in an alcoholic solvent (e.g., methanol) under an atmosphere of hydrogen to give the saturated tricyclic system XLIV. Standard methodology (as described above) allows the tricycle XLIV to be converted to the ester XLV and then to compounds of formula IK.

SCHEME VII
PREPARATION OF FORMULA I COMPOUNDS

WHEREIN: W = —CH$_2$—
X = —CH$_2$O—
Y = —CH=CHCH$_2$—, —(CH$_2$)$_3$—
Z = a bond
p = 0
Q = —CO$_2$H

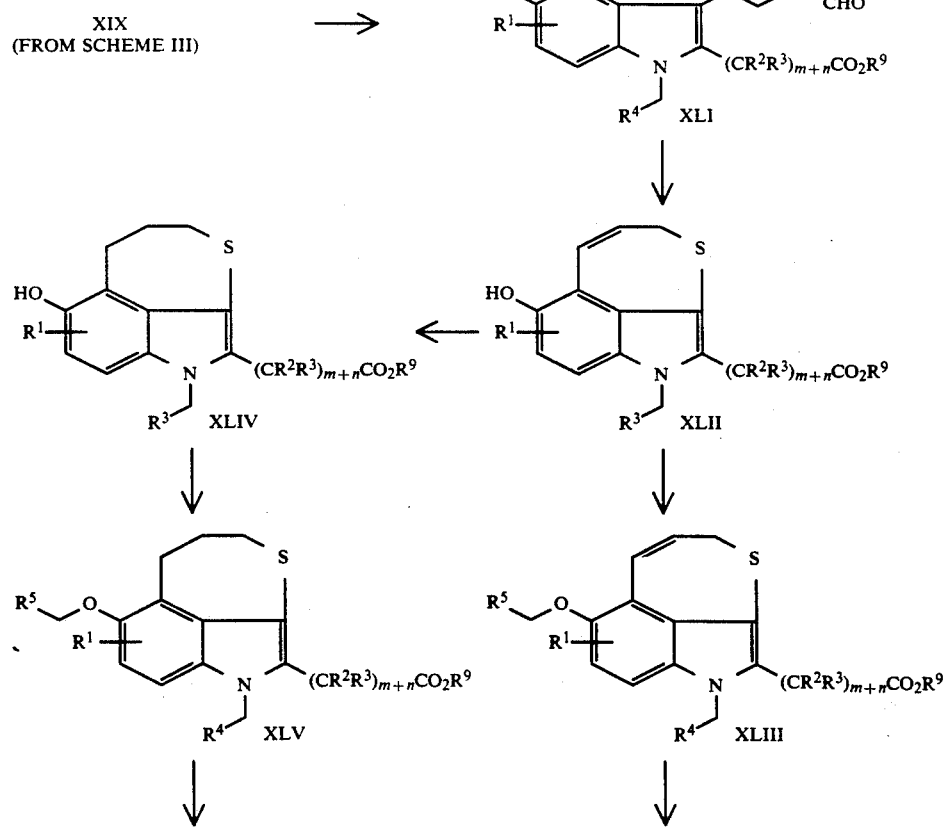

SCHEME VII
PREPARATION OF FORMULA I COMPOUNDS

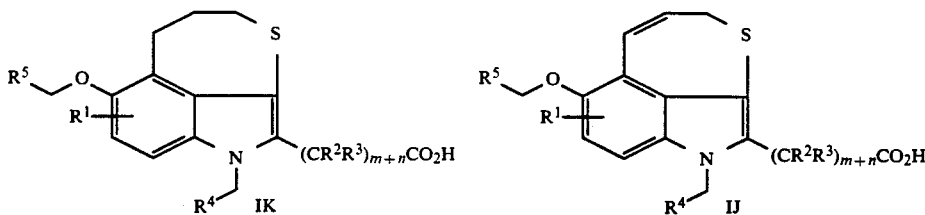

SCHEME VIII

Scheme VIII describes the preparation of compounds of formula I by modification of compounds of formula I wherein Q is —$CO_2H$. For example, the appropriate compound I (Schemes I, II, V, VI, or VII) may be treated with oxalyl chloride and a catalytic amount of DMF in a suitable organic solvent (e.g., dichloromethane) and then, after addition of a hydroxylamine, $R^6NHOH$, this affords the hydroxamic acid XLVI.

Stirring a solution of the acid I, an appropriate carbodiimide such as 1-cyclohexyl-3-(2-morpholinoethyl)carbodiimide metho-p-toluenesulfonate, an organic base such as DMAP and a sulfonamide, $R^{14}S(O)_2NH_2$, in an organic solvent (e.g., dichloromethane) gives the acylsulfonamide XLVII. Alternatively, the acid I may be reacted with a chloroformate such as isobutylchloroformate in the presence of an organic base (e.g., triethylamine) and an appropriate organic solvent (e.g., THF). When a primary or secondary amine $HN(R^6)_2$ is added the product is an amide of formula LV. The amido-acid LVI results from conversion of the acid I to the corresponding amido-ester (the acid I, oxalyl chloride, DMF, an amino ester such as glycine methyl ester hydrochloride in an organic solvent such as THF) followed by hydrolysis using previously described conditions.

The amino-amide LVII can be prepared using conditions similar to those used for the preparation of acylsulfonamide XLVII except in the reaction the alkylsulfonamide is replaced with a diamine such as 1,3-diaminopropane. The aminoamide LVII may then be further reacted (the aminoamide LVII, an organic base such as triethylamine, an acyl chloride such as acetyl chloride in an organic solvent (e.g., THF) to afford the compound LVIII.

When the acid I is dissolved in an organic solvent, for example THF, and treated sequentially with a chloroformate such as isobutylchloroformate, an organic base (e.g., triethylamine) and an aqueous solution of a tetraalkylammonium salt (e.g., tetrabutylammonium bromide) and sodium azide the product isolated is the acylazide XLVIII. This compound when heated in a suitable organic solvent such as chloroform rearranges to yield the isocyanate XLIX. The isocyanate XLIX when heated with an organic acid like, for example, acetic acid and an inorganic acid such as 6N HCl gives the amine L. The amide LII is prepared from amine L using the method used to prepare the diamide LVIII. Similarly, the compound LIII may be prepared from the amine L using the method described for the preparation of the diamide LVIII except replacing the acyl chloride with ethyl oxalyl chloride. Hydrolysis of compound LIII using standard conditions (described previously) then affords the acid LIV. Alternatively, stirring a solution of the amine L and a sulfonyl chloride, $R^{14}S(O)_2Cl$, in an organic solvent (e.g., THF) allows the preparation of compounds of formula LI. All the compounds in Scheme VIII are representatives of Formula I except for XLVIII and XLIX.

SCHEME VIII
PREPARATION OF FURTHER COMPOUNDS OF FORMULA I

WHEREIN: W = —$CH_2$—
X = —$CH_2O$—
Y = —$CH_2C(R^{12})_2$—
p = 0

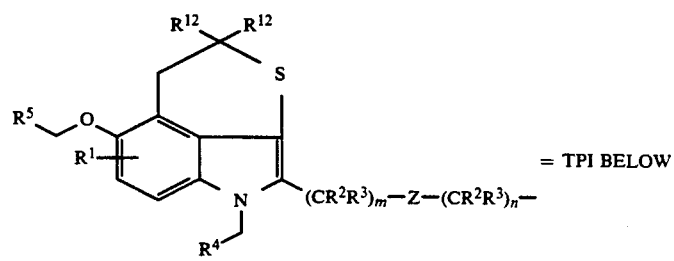

SCHEME VIII
PREPARATION OF FURTHER COMPOUNDS OF FORMULA I

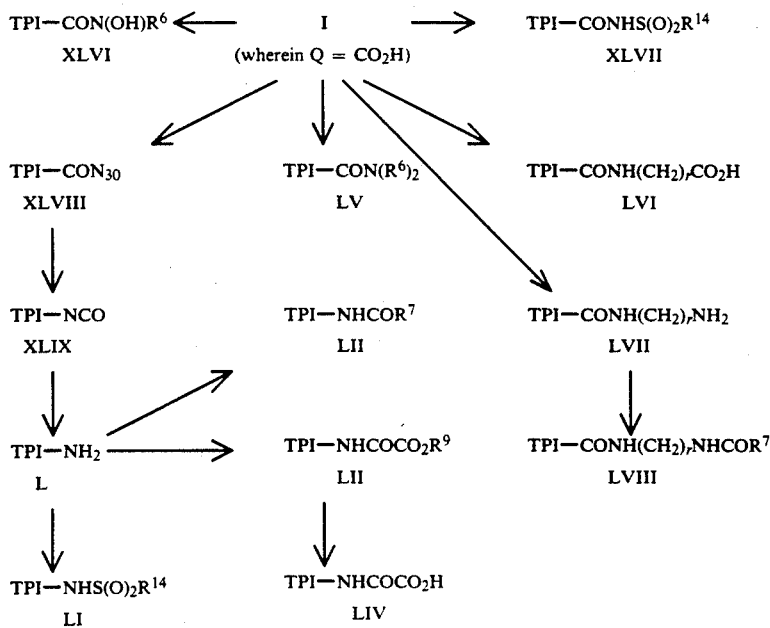

SCHEME IX

In Scheme IX the routes used to prepare compounds of formula I where X=—CH$_2$S— are described. As the first step, the tetracyclic indole XII (from Scheme II) is dissolved in an organic solvent (e.g., DMF) and is treated with an inorganic base such as NaH followed by the addition of dimethylthiocarbamoyl chloride to provide the intermediate LIX. Heating the intermediate LIX neat causes the compound to rearrange to give the thiophenol derivative LX. This compound when refluxed in a solution of, for example, sodium methoxide in methanol followed by subsequent reaction of the acid with thionyl chloride in methanol and then reduction of the disulfide bond (triphenylphosphine, 6N HCl in an organic solvent such as dioxane) gives the tricyclic thiophenol LXI. The thiol group of intermediate LXI may be alkylated by stirring a solution of the thiophenol LXI, an organic base such as triethylamine and an appropriate alkylating agent, R$^5$CH$_2$X$^1$ in a solvent such as THF. This procedure affords the intermediate LXII which may then be N-alkylated according to the method described in Scheme II to give the thiopyranoindole LXIII. Hydrolysis of the ester LXIII using standard conditions affords the acid IL. Alternatively, the ester LXIII may be transformed to the acid IM or the tetrazole IN according to the experimental procedures described in Scheme IV.

SCHEME IX
PREPARATION OF FORMULA I COMPOUNDS

WHEREIN: W = —CH$_2$—
X = —CH$_2$S—
Y = —CH$_2$C(R$^{12}$)$_2$—
Z = a bond
p = 0
Q = —CO$_2$H -TETRAZOL-5-YL

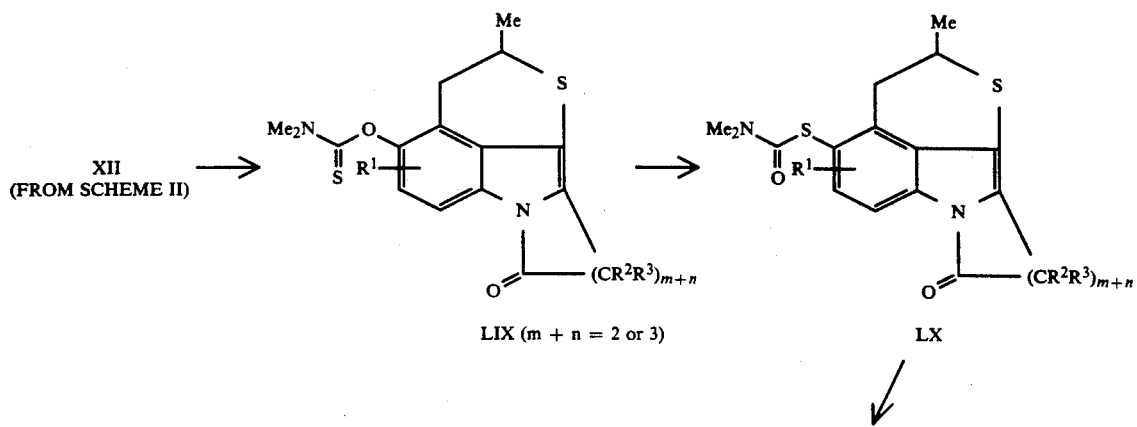

-continued
SCHEME IX
PREPARATION OF FORMULA I COMPOUNDS

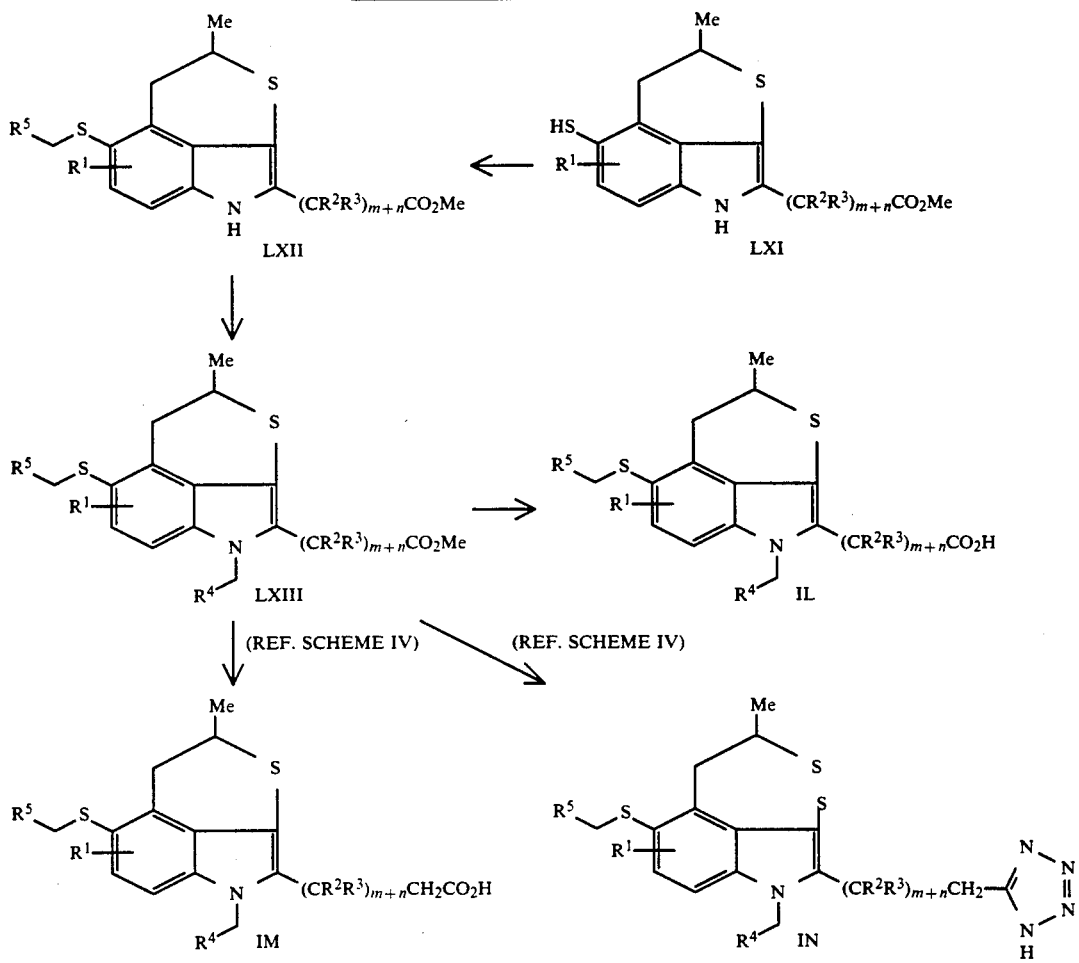

SCHEME X

Compounds corresponding to formula I where X=—CH=CH—, —(CH$_2$)$_2$—, or —CH$_2$OCH$_2$— are prepared using the reaction pathways outlined in Scheme X. The phenol XXX (from Scheme IV) may be converted to the triflate LXIV by stirring with trifluoromethanesulfonic anhydride, and an organic base (e.g., pyridine) in a solvent such as dichloromethane. A solution of the triflate LXIV in DMSO/methanol as solvent with an organic base such as triethylamine, a phosphine such as diphenylphosphinoethane, a palladium II salt (e.g., palladium(II) acetate) and an atmosphere of carbon monoxide gives the ester LXV. Reaction of the ester LXV with a reducing agent, for example lithium borohydride, in an organic solvent such as THF yields the alcohol LXVI. The coupling of the alcohol LXVI with an appropriate alkylating agent R$^5$CH$_2$X$^1$ to give intermediate LXX followed by conversion to the tetrazole IT or the acid IS may be done using the procedures described in Scheme IV for the synthesis of compounds of formula XXV, IC and IB respectively.

Alternatively, the alcohol LXVI may be oxidised using, for example, manganese dioxide in an organic solvent such as dichloromethane to produce the aldehyde LXVII. A Wittig reaction between the aldehyde LXVII and an ylid derived from deprotonation of a phosphonium salt, R$^5$CH$_2$P(C$_6$H$_5$)$_3$X$^1$, using an inorganic base (e.g., n-BuLi) in an organic solvent such as THF affords the unsaturated nitrile LXVIII. The nitrile LXVIII may then be converted to the acid IO or the tetrazole IP using conditions described previously. Alternatively, the nitrile LXVIII may be hydrogenated in an alcoholic solvent (e.g., methanol) using a catalyst such as 10% palladium on carbon and a hydrogen atmosphere to yield the saturated nitrile LXIX. The nitrile LXIX may then be converted as described above to provide the acid IQ and the tetrazole IR.

SCHEME X
PREPARATION OF FORMULA I COMPOUNDS

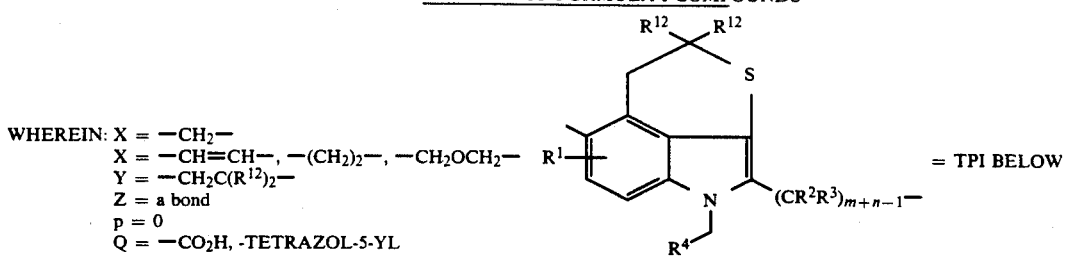

= TPI BELOW

WHEREIN: X = —CH₂—
X = —CH=CH—, —(CH₂)₂—, —CH₂OCH₂—
Y = —CH₂C(R¹²)₂—
Z = a bond
p = 0
Q = —CO₂H, -TETRAZOL-5-YL

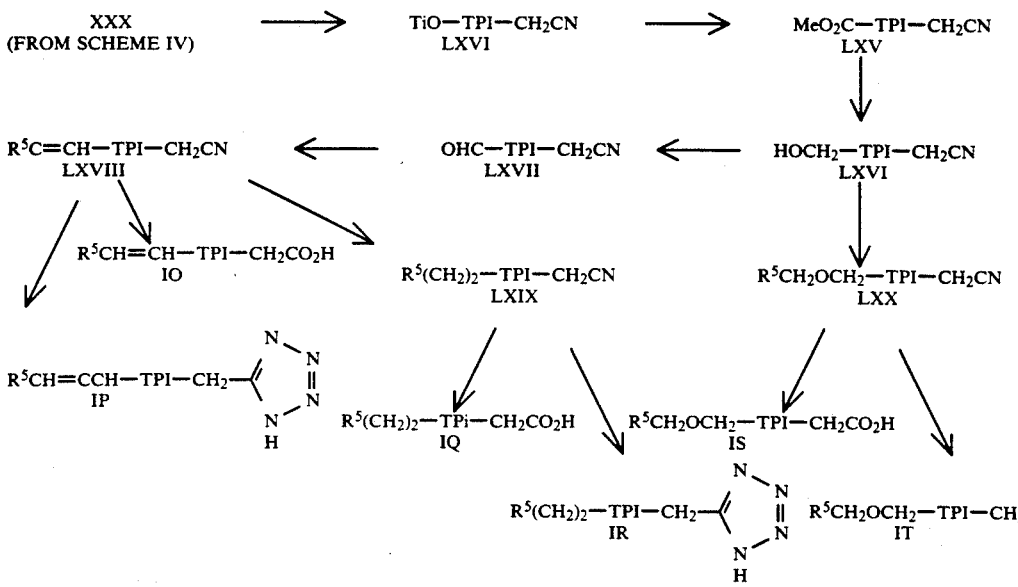

SCHEME XI

As shown in Scheme XI, the indole intermediate XXX (from Scheme IV) on reaction with an inorganic base such as NaH in a solvent such as DMF followed by addition of bromoacetaldehyde diethylacetal yields the intermediate LXXI. Hydrolysis of the diethylacetal of intermediate LXXI using an inorganic acid (e.g., 6N HCl) in an appropriate solvent such as THF provides the aldehyde LXXII. The conversion of the aldehyde LXXII to the alkene intermediate LXXIII followed by hydrogenation to give the nitrile LXXIV and subsequent reactions to provide either the acid IU or the tetrazole IW are accomplished using the procedures described for Scheme X.

SCHEME XI
PREPARATION OF FORMULA I COMPOUNDS

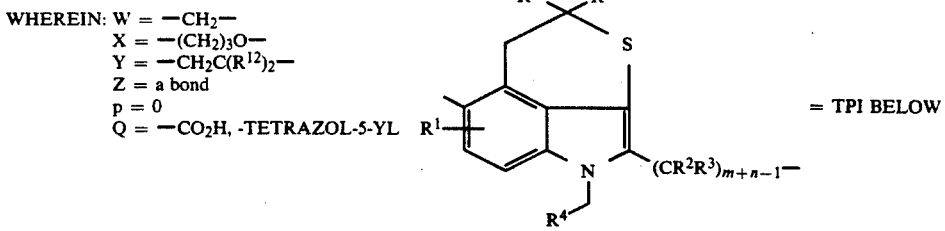

= TPI BELOW

WHEREIN: W = —CH₂—
X = —(CH₂)₃O—
Y = —CH₂C(R¹²)₂—
Z = a bond
p = 0
Q = —CO₂H, -TETRAZOL-5-YL

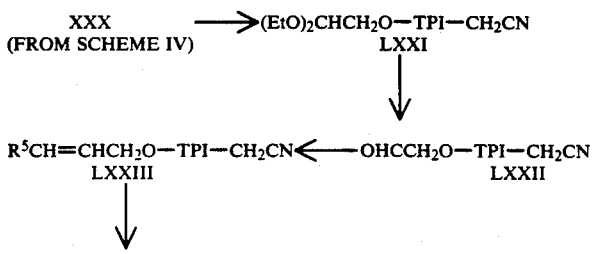

SCHEME XI
PREPARATION OF FORMULA I COMPOUNDS

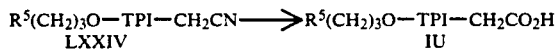

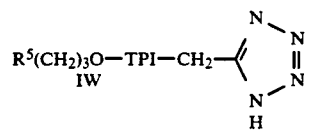

SCHEME XII

The unsaturated derivatives of formula I described in Scheme XII may be prepared by initial condensation of phenol lactam X (Scheme II) with 2,3-dibromopropene using an inorganic base such sodium hydride in an appropriate solvent, for example DMF, to afford allylic ether LXXV which is isomerized by heating in a high boiling solvent such as 1,2-dichlorobenzene in the presence of a mild inorganic base such as sodium acetate to the o-bromoallyl phenol LXXVI. Treatment of this material with a strong inorganic base such as sodium hydride in a polar solvent such as DMF leads to the o-propargyl phenol LXXVII. Heating this product in a high-boiling solvent such as 1,2-dichlorobenzene in the presence of an organic acid such as p-toluenesulfonic acid effects the cyclization to the unsaturated thiopyrano indole LXXVIII. Coupling of this phenol with an alkyl halide is done as described in Scheme I to afford the ether intermediate LXXIX. Opening of the lactam ring followed by N-alkylation as described in Scheme II leads to the acid IY. The homologation strategies described in Scheme II and IV afford the acid IZ and the tetrazole IAA.

SCHEME XII
PREPARATION OF FORMULA I COMPOUNDS

WHEREIN: W—CH$_2$—
X = —CH$_2$O—
Y = —CH=C(Me)—
Z = a bond
p = 0
Q = —CO$_2$H, -TETRAZOL-5-YL

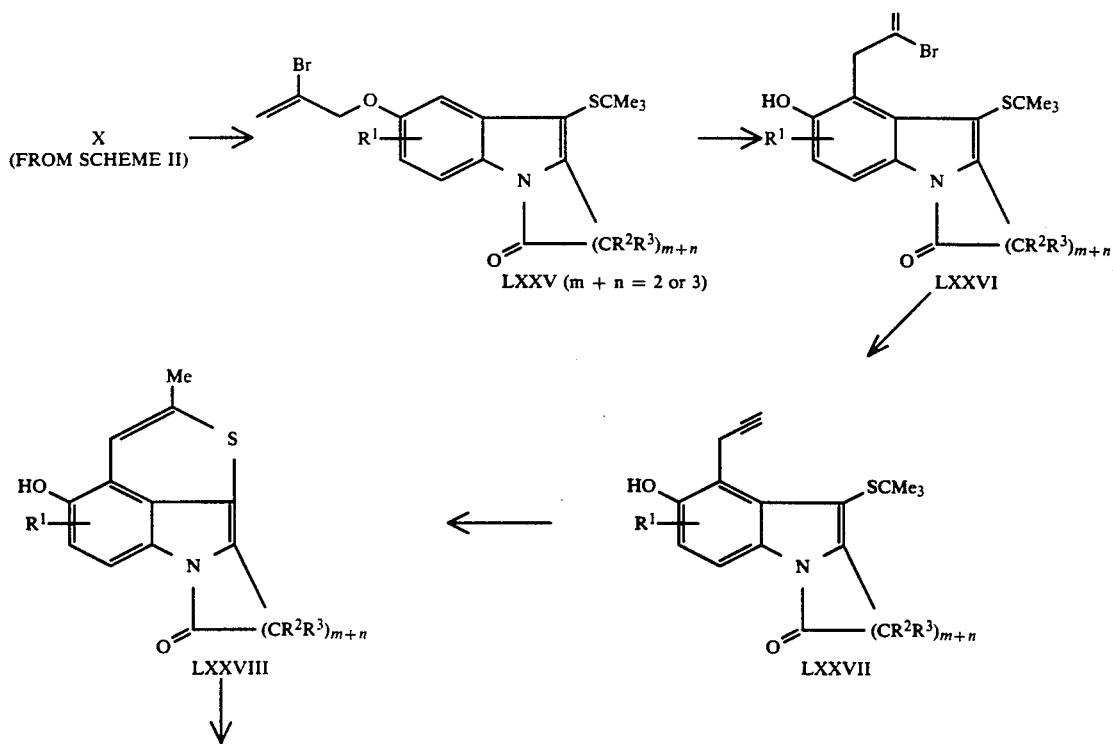

-continued
SCHEME XII
PREPARATION OF FORMULA I COMPOUNDS

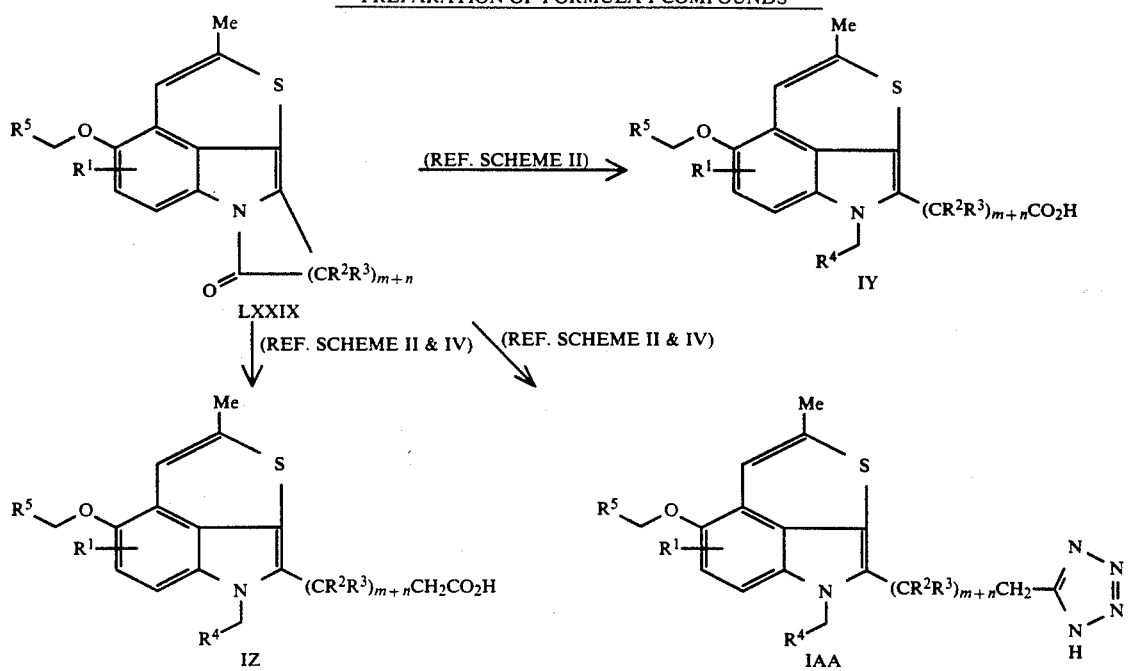

TABLE A

| AGENT | $X^1$ | $R^4/R^5$ | Alkylating Agents $R^4CH_2X^1$ and $R^5CH_2X^1$ NAME |
|---|---|---|---|
| 1 | Cl | 4-ClC$_6$H$_4$ | 4-chlorobenzyl chloride (Aldrich)* |
| 2 | Cl | C$_6$H$_5$ | Benzyl chloride (Aldrich) |
| 3 | Cl | 4-MeOC$_6$H$_4$ | 4-methoxybenzyl chloride (Aldrich) |
| 4 | Cl | 3-MeOC$_6$H$_4$ | 3-methoxybenzyl chloride (Aldrich) |
| 5 | Cl | 4-MeS(O)$_2$C$_6$H$_4$ | 4-methylsulfonylbenzyl chloride (C.A.:78:111325q (1973)) |
| 6 | Cl | 4-MeSC$_6$H$_4$ | 4-methylthiobenzyl chloride (C.A.: 56:4773g (1962)) |
| 7 | Cl | 4-C$_6$H$_5$C$_6$H$_4$ | 4-phenylbenzyl chloride (Aldrich) |
| 8 | Br | 4-NCC$_6$H$_4$ | 4-cyanobenzyl bromide (Aldrich) |
| 9 | Br | 3-C$_6$H$_5$(CH$_2$)$_2$ | 3-phenylpropyl bromide (Aldrich) |
| 10 | Cl | CH$_2$O$_2$C$_6$H$_3$ | 3,4-methylenedioxybenzyl chloride (Tet. Lett. 47, 4789–4792 (1972)) |
| 11 | I | C$_6$H$_5$OCH$_2$ | 2-phenoxyethyl iodide (C.A.: 77:15624v (1972)) |
| 12 | Br | C$_6$H$_5$CH=CH | Cinnamyl bromide (Aldrich) |
| 13 | Br | c-Hex | Cyclohexylmethyl bromide (Aldrich) |
| 14 | I | H | Methyl iodide (Aldrich) |
| 15 | Br | CH$_2$=CH | Allyl bromide (Aldrich) |
| 16 | Br | CH$_3$(CH$_2$)$_2$ | n-butyl bromide (Aldrich) |
| 17 | Br | CH$_3$(CH$_2$)$_8$ | n-decyl bromide (Aldrich) |
| 18 | OS(O)$_2$C$_6$H$_4$Me | C$_6$H$_5$CH$_2$ | 2-phenethyl p-toluenesulfonate (C.A.:72:47966w (1970)) |
| 19 | I | c-Hex(CH$_2$)$_2$ | 3-cyclohexylpropyl iodide** |
| 20 | OS(O)$_2$CH$_3$ | C$_4$H$_3$S | 2-thienylmethyl methanesulfonate** |
| 21 | Cl | 2-C$_5$H$_4$N/HCl | 2-picolyl chloride hydrochloride (Aldrich) |
| 22 | Cl | 2-C$_9$H$_6$N/HCl | 2-chloromethylquinoline hydrochloride (Aldrich) |

TABLE A-continued

Alkylating Agents
$R^4CH_2X^1$ and $R^5CH_2X^1$

| AGENT | $X^1$ | $R^4/R^5$ | NAME |
|---|---|---|---|
| 23 | Cl | 5-$C_6H_5$-2-$C_5H_3N$ | 5-phenyl-2-picolyl chloride** |
| 24 | Br | 1-AdaCH$_2$ | 2-(1-adamantyl)ethyl bromide** |
| 25 | Cl | 4-FC$_6H_4$ | 4-fluorobenzyl chloride (PCR Inc.) |
| 26 | Cl | 3-ClC$_6H_4$ | 3-chlorobenzyl chloride (Aldrich) |
| 27 | Cl | 3-FC$_6H_4$ | 3-Fluorobenzyl chloride (Aldrich) |
| 28 | Cl | 5-$C_6H_5$-2-$C_5H_3$N(O) | 2-chloromethyl-5-phenylpyridine N-oxide** |
| 29 | Cl | 2-$C_9H_6$N(O) | 2-chloromethylquinoline N-oxide (Chem. Pharm. Bull. 28, 2436–2442 (1980)) |
| 30 | Cl | 6-$C_6H_5$-2-$C_5H_3N$ | 6-phenyl-2-picolyl chloride (C.A.:103:215289g (1985)) |
| 31 | Cl | 4-$C_6H_5$-2-$C_5H_3N$ | 4-phenyl-2-picolyl chloride (C.A.:105:42802e (1986)) |
| 32 | Cl | 2-$C_6H_5$-3-$C_5H_3N$ | 2-phenyl-3-picolyl chloride** |
| 33 | Cl | 3-$C_5H_4$N/HCl | 3-picolyl chloride hydrochloride (Aldrich) |
| 34 | Cl | 4-$C_5H_4$N/HCl | 4-picolyl chloride hydrochloride (Aldrich) |
| 35 | Cl | 2-$C_6H_5$-4-$C_5H_3N$ | 2-phenyl-4-picolyl chloride (C.A.:64:690h (1966)) |
| 36 | Cl | 5-NC-2-$C_5H_3N$ | 5-cyano-2-picolyl chloride (Aust. J. Chem. 35, 1451–1468 (1982)) |
| 37 | Cl | 5-n-Bu-2-$C_5H_3N$ | 5-butyl-2-picolyl chloride (C.A.:78:29778f (1973)) |
| 38 | Cl | 6-Cl-2-$C_5H_3N$ | 6-chloro-2-picolyl chloride (Tetrahedron 38, 3277–3280 (1982)) |
| 39 | Cl | 6-Cl-5-$C_6H_5$-2-$C_5H_2N$ | 6-chloro-5-phenyl-2-picolyl chloride** |
| 40 | Cl | 4-Cl-5-$C_6H_5$-2-$C_5H_2N$ | 4-chloro-5-phenyl-2-picolyl chloride** |
| 41 | Cl | t-Bu($C_6H_5$)$_2$SiO-2-$C_5H_3N$ | 5-(t-butyldiphenylsilyloxy)-2-picolyl chloride** |
| 42 | Cl | 5-$C_6H_5CH_2$-2-$C_5H_3N$ | 5-benzyl-2-picolyl chloride** |
| 43 | Cl | 5-(4-ClC$_6H_4$)-2-$C_5H_3N$ | 5-(4-chlorophenyl)-2-picolyl chloride** |
| 44 | Cl | 3-$C_9H_6$N | 3-chloromethylisoquinoline (C.A.:94, 121512t (1981) |
| 45 | Br | 4-$C_9H_6$N | 4-bromomethylquinoline (Indian J. Chem. 11, 1051 (1973)) |
| 46 | Cl | 2-$C_8H_6N_2$ | 2-chloromethyl-1,8-naphthyridine** |
| 47 | Cl | 4-(2-$C_5H_4$N)$C_6H_4$ | 4-(2-pyridinyl)benzyl chloride** |
| 48 | Cl | 3,5-Me$_2$-4-$C_3$NO | 4-chloromethyl-3,5-dimethylisoxazole (Aldrich) |
| 49 | Cl | 2-(4-ClC$_6H_4$)-4-$C_3$HNS | 4-chloromethyl-2-(4-chlorophenyl)thiazole (Maybridge) |
| 50 | Cl | 5-$C_6H_5$-2-$C_3$HNO | 2-chloromethyl-5-phenyloxazole (J.O.C. 45, 3657–3664 (1980)) |
| 51 | Cl | 5-$C_6H_5$-2-$C_4H_2N_2$ | 2-chloromethyl-5-phenylpyrimidine (Chem. Ber. 104, 2975–2983 (1971)) |
| 52 | Cl | 5-$C_6H_5$-2-$C_4H_2N_2$ | 2-chloromethyl-5-phenyl pyrazine (Chem. Pharm. Bull. 27, 2027–2041 (1979)) |
| 53 | Br | 2-$C_{10}H_7$ | 2-bromomethylnaphthalene (Aldrich) |
| 54 | Cl | 5-(1-$C_{10}H_7$)-2-$C_5H_3N$ | 5-(1-naphthyl)-2-picolyl chloride** |
| 55 | Cl | 5-(4-MeOC$_6H_4$)-2-$C_5H_3N$ | 5-(4-methoxyphenyl)-2-picolyl chloride** |
| 56 | Cl | 5-CO$_2$Me-2-$C_5H_3N$ | 5-carbomethoxy-2-picolyl chloride (C.A.:79:105075n (1973)) |
| 57 | Cl | 2-$C_6H_5$-5-$C_7H_3$NO | 5-chloromethyl-2-phenylfuro[3,2-b]pyridine** |
| 58 | Cl | 3-CF$_3C_6H_4$ | 3-trifluoromethylbenzyl chloride (Aldrich) |

*Aldrich Chemical Co., Milwaukee, Wisc.
Maybridge Chemical Co., Cornwall, U.K.
PCR Inc., Gainsville, Fla.
**Preparation described infra.

TABLE 1

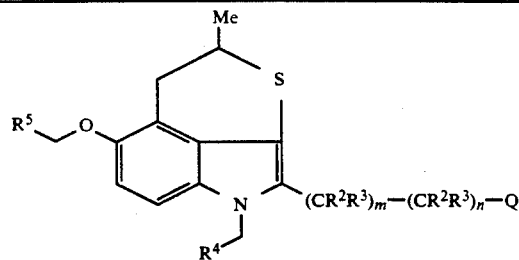

| Ex. No. | R⁴ | R⁵ | $(CR^2R^3)_m-(CR^2R^3)_n$ | Q |
|---|---|---|---|---|
| 1 | 4-ClC₆H₄ | 5-C₆H₅-2-C₅H₃N⁺ | CH₂C(Me)₂ | CO₂H |
| 2 | n-Pr | 5-C₆H₅-2-C₅H₃N | CH₂C(Me)₂ | CO₂H |
| 3 | H | 5-C₆H₅-2-C₅H₃N | CH₂C(Me)₂ | CO₂H |
| 4 | C₆H₅ | 5-C₆H₅-2-C₅H₃N | CH₂C(Me)₂ | CO₂H |
| 5 | 4-MeOC₆H₄ | 5-C₆H₅-2-C₅H₃N | CH₂C(Me)₂ | CO₂H |
| 6 | 3-MeOC₆H₄ | 5-C₆H₅-2-C₅H₃N | CH₂C(Me)₂ | CO₂H |
| 7 | 4-MeS(O)₂C₆H₄ | 5-C₆H₅-2-C₅H₃N | CH₂C(Me)₂ | CO₂H |
| 8 | 4-MeSC₆H₄ | 5-C₆H₅-2-C₅H₃N | CH₂C(Me)₂ | CO₂H |
| 9 | 4-C₆H₅C₆H₄ | 5-C₆H₅-2-C₅H₃N | CH₂C(Me)₂ | CO₂H |
| 10 | 4-NC—C₆N₄ | 5-C₆H₅-2-C₅H₃N | CH₂C(Me)₂ | CO₂H |
| 11 | C₆H₅(CH₂)₂ | 5-C₆H₅-2-C₅H₃N | CH₂C(Me)₂ | CO₂H |
| 12* | 3,4-CH₂O₂C₆H₃ | 5-C₆H₅-2-C₅H₃N | CH₂C(Me)₂ | CO₂H |
| 13 | C₆H₅OCH₂ | 5-C₆H₅-2-C₅H₃N | CH₂C(Me)₂ | CO₂H |
| 14 | C₆H₅CH=CH (E-isomer) | 5-C₆H₅-2-C₅H₃N | CH₂C(Me)₂ | CO₂H |
| 15 | c-Hex | 5-C₆H₅-2-C₅H₃N | CH₂C(Me)₂ | CO₂H |
| 16 | CH₂=CH | 5-C₆H₅-2-C₅H₃N | CH₂C(Me)₂ | CO₂H |
| 17 | Me(CH₂)₈ | 5-C₆H₅-2-C₅H₃N | CH₂C(Me)₂ | CO₂H |
| 18 | C₆H₅CH₂ | 5-C₆H₅-2-C₅H₃N | CH₂C(Me)₂ | CO₂H |
| 19 | c-Hex—(CH₂)₂ | 5-C₆H₅-2-C₅H₃N | CH₂C(Me)₂ | CO₂H |
| 20* | 2-C₄H₃S | 5-C₆H₅-2-C₅H₃N | CH₂C(Me)₂ | CO₂H |
| 21* | 2-C₅H₄N | 5-C₆H₅-2-C₅H₃N | CH₂C(Me)₂ | CO₂H |
| 22* | 2-C₉H₆N | 5-C₆H₅-2-C₅H₃N | CH₂C(Me)₂ | CO₂H |
| 23 | 5-C₆H₅-2-C₅H₃N | 5-C₆H₅-2-C₅H₃N | CH₂C(Me)₂ | CO₂H |
| 24* | 1-Ada—CH₂ | 5-C₆H₅-2-C₅H₃N | CH₂C(Me)₂ | CO₂H |
| 25 | 3-CF₃C₆H₄ | 5-C₆H₅-2-C₅H₃N | CH₂C(Me)₂CH₂ | CO₂H |
| 26 | 3-CF₃C₆H₄ | 5-C₆H₅-2-C₅H₃N | CH₂C(Me)₂CH₂ | CN₄H⁺ |
| 27 | 4-ClC₆H₄ | 5-C₆H₅-2-C₅H₃N | CH₂C(Me)₂CH₂ | CO₂H |
| 28 | 4-ClC₆H₄ | 5-C₆H₅-2-C₅H₃N | CH₂C(Me)₂CH₂ | CN₄H |
| 29 | C₆H₅ | 5-C₆H₅-2-C₅H₃N | CH₂C(Me)₂CH₂ | CO₂H |
| 30 | C₆H₅ | 5-C₆H₅-2-C₅H₃N | CH₂C(Me)₂CH₂ | CN₄H |
| 31 | 3-MeOC₆H₄ | 5-C₆H₅-2-C₅H₃N | CH₂C(Me)₂CH₂ | CO₂H |
| 32 | 3-MeOC₆H₄ | 5-C₆H₅-2-C₅H₃N | CH₂C(Me)₂CH₂ | CN₄H |
| 33 | 4-FC₆H₄ | 5-C₆H₅-2-C₅H₃N | CH₂C(Me)₂CH₂ | CO₂H |
| 34 | 4-FC₆H₄ | 5-C₆H₅-2-C₅H₃N | CH₂C(Me)₂CH₂ | CN₄H |
| 35 | 3-ClC₆H₄ | 5-C₆H₅-2-C₅H₃N | CH₂C(Me)₂CH₂ | CO₂H |
| 36 | 3-ClC₆H₄ | 5-C₆H₅-2-C₅H₃N | CH₂C(Me)₂CH₂ | CN₄H |
| 37 | 3-FC₆H₄ | 5-C₆H₅-2-C₅H₃N | CH₂C(Me)₂CH₂ | CO₂H |
| 38 | 3-FC₆H₄ | 5-C₆H₅-2-C₅H₃N | CH₂C(Me)₂CH₂ | CN₄H |
| 39* | 2-C₅H₄N | 5-C₆H₅-2-C₅H₃N | CH₂C(Me)₂CH₂ | CO₂H |
| 40* | 2-C₅H₄N | 5-C₆H₅-2-C₅H₃N | CH₂C(Me)₂CH₂ | CN₄H |
| 41 | C₆H₅(CH₂)₂ | 5-C₆H₅-2-C₅H₃N | CH₂C(Me)₂CH₂ | CO₂H |
| 42 | C₆H₅(CH₂)₂ | 5-C₆H₅-2-C₅H₃N | CH₂C(Me)₂CH₂ | CN₄H |
| 43 | c-Hex | 5-C₆H₅-2-C₅H₃N | CH₂C(Me)₂CH₂ | CO₂H |
| 44 | c-Hex | 5-C₆H₅-2-C₅H₃N | CH₂C(Me)₂CH₂ | CH₄H |
| 45 | 4-ClC₆H₄ | 5-C₆H₅-2-C₅H₃N | CH₂C(Me)₂CH₂ | CONHS(O)₂Me |
| 46 | 4-ClC₆H₄ | 5-C₆H₅-2-C₅H₃N | CH₂C(Me)₂CH₂ | CONHS(O)₂C₆H₅ |
| 47 | 4-ClC₆H₄ | 5-C₆H₅-2-C₅H₃N | CH₂C(Me)₂CH₂ | CONHS(O)₂CF₃ |
| 48 | 4-ClC₆H₄ | 5-C₆H₅-2-C₅H₃N | CH₂C(Me)₂CH₂ | CO₂H |
| 49 | 4-ClC₆H₄ | 5-C₆H₅-2-C₅H₃N | CH₂C(Me)₂CH₂ | CN₄H |
| 50 | 4-ClC₆H₄ | 5-C₆H₅-2-C₅H₃N | — | CO₂H |
| 51 | 4-ClC₆H₄ | 5-C₆H₅-2-C₅H₃N | CH₂ | CO₂H |
| 52 | 4-ClC₆H₄ | 5-C₆H₅-2-C₅H₃N | (CH₂)₂ | CO₂H |
| 53 | 4-ClC₆H₄ | 5-C₆H₅-2-C₅H₃N | (CH₂)₂ | CN₄H |
| 54 | 4-ClC₆H₄ | 5-C₆H₅-2-C₅H₃N | (CH₂)₂C(Me)₂ | CO₂H |
| 55 | 4-ClC₆H₄ | 5-C₆H₅-2-C₅H₃N | CH₂C(Me)₂ | CON(OH)Me |
| 56 | 4-ClC₆H₄ | 5-C₆H₅-2-C₅H₃N | CH₂C(Me)₂ | CONH₂ |
| 57 | 4-ClC₆H₄ | 5-C₆H₅-2-C₅H₃N | CH₂C(Me)₂ | CONHMe |
| 58 | 4-ClC₆H₄ | 5-C₆H₅-2-C₅H₃N | CH₂C(Me)₂ | CON(Me)₂ |
| 59 | 4-ClC₆H₄ | 5-C₆H₅-2-C₅H₃N | CH₂C(Me)₂ | CONHCH₂CO₂H |
| 60 | 4-ClC₆H₄ | 5-C₆H₅-2-C₅H₃N | CH₂C(Me)₂ | CONH(CH₂)₃NHAc |
| 61 | 4-ClC₆H₄ | 5-C₆H₅-2-C₅H₃N | CH₂C(Me)₂ | CONH(CH₂)₃NH₂ |
| 62 | 4-ClC₆H₄ | 5-C₆H₅-2-C₅H₃N | CH₂C(Me)₂ | CONHn-Bu |
| 63 | 4-ClC₆H₄ | 5-C₆H₅-2-C₅H₃N | CH₂C(Me)₂ | NH₂ |
| 64 | 4-ClC₆H₄ | 5-C₆H₅-2-C₅H₃N | CH₂C(Me)₂ | NHAc |
| 65 | 4-ClC₆H₄ | 5-C₆H₅-2-C₅H₃N | CH₂C(Me)₂ | NHCOCO₂Et |
| 66 | 4-ClC₆H₄ | 5-C₆H₅-2-C₅H₃N | CH₂C(Me)₂ | NHCOCO₂H |

TABLE 1-continued

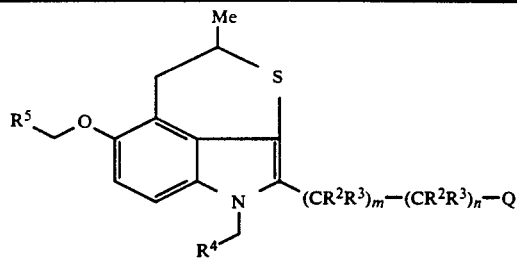

| Ex. No. | R⁴ | R⁵ | $(CR^2R^3)_m$—$(CR^2R^3)_n$ | Q |
|---|---|---|---|---|
| 67 | 4-ClC₆H₄ | 5-C₆H₅-2-C₅H₃N | CH₂C(Me)₂ | NHS(O)₂C₆H₅ |
| 89 (+)-isomer | 4-ClC₆H₄ | 5-C₆H₅-2-C₅H₃N | CH₂C(Me)₂ | CO₂H |
| 90 (−)-isomer | 4-ClC₆H₄ | 5-C₆H₅-2-C₅H₃N | CH₂C(Me)₂ | CO₂H |
| 94* | 4-ClC₆H₄ | 5-C₆H₅-2-C₅H₃N(O) | CH₂C(Me)₂ | CO₂H |
| 95* | 4-ClC₆H₄ | 5-C₆H₅-2-C₅H₃N(O) | CH₂C(Me)₂CH₂ | CN₄H |
| 96* | 4-ClC₆H₄ | 2-C₉H₆N | CH₂C(Me)₂ | CO₂H |
| 97* | 4-ClC₆H₄ | 2-C₉H₆N(O) | CH₂C(Me)₂ | CO₂H |
| 98 | 4-ClC₆H₄ | 4-C₆H₅C₆H₄ | CH₂C(Me)₂ | CO₂H |
| 99 | 4-ClC₆H₄ | 6-C₆H₅-2-C₅H₃N | CH₂C(Me)₂ | CO₂H |
| 100 | 4-ClC₆H₄ | 4-C₆H₅-2-C₅H₃N | CH₂C(Me)₂ | CO₂H |
| 101 | 4-ClC₆H₄ | 2-C₆H₅-3-C₅H₃N | CH₂C(Me)₂ | CO₂H |
| 102 | 4-ClC₆H₄ | 2-C₅H₄N⁺ | CH₂C(Me)₂ | CO₂H |
| 103 | 4-ClC₆H₄ | 3-C₅H₄N | CH₂C(Me)₂ | CO₂H |
| 104 | 4-ClC₆H₄ | 4-C₅H₄N | CH₂C(Me)₂ | CO₂H |
| 105 | 4-ClC₆H₄ | 2-C₆H₅-4-C₅H₃N | CH₂C(Me)₂ | CO₂H |
| 106 | 4-ClC₆H₄ | 5-MeO-2-C₅H₃N | CH₂C(Me)₂ | CO₂H |
| 107 | 4-ClC₆H₄ | 5-H₂NCO-2-C₅H₃N | CH₂C(Me)₂ | CO₂H |
| 108 | 4-ClC₆H₄ | 5-(Me)₂NCO-2-C₅H₃N | CH₂C(Me₂ | CO₂H |
| 109 | 4-ClC₆H₄ | 5-C₆H₅CH₂O-2-C₅H₃N | CH₂C(Me)₂ | CO₂H |
| 110 | 4-ClC₆H₄ | 5-NC-2-C₅H₃N | CH₂C(Me)₂ | CO₂H |
| 111 | 4-ClC₆H₄ | 5-n-Bu-2-C₅H₃N | CH₂C(Me)₂ | CO₂H |
| 112 | 4-ClC₆H₄ | 6-Cl-2-C₅H₃N | CH₂C(Me)₂ | CO₂H |
| 113 | 4-ClC₆H₄ | 6-Cl-5-C₆H₅-2-C₅H₂N | CH₂C(Me)₂ | CO₂H |
| 114 | 4-ClC₆H₄ | 4-Cl-5-C₆H₅-2-C₅H₂N | CH₂C(Me)₂ | CO₂H |
| 115 | 4-ClC₆H₄ | 4-MeO-5-C₆H₅-2-C₅H₂N | CH₂C(Me)₂ | CO₂H |
| 116 | 4-ClC₆H₄ | 5-C₆H₅CH₂-2-C₅H₃N | CH₂C(Me)₂ | CO₂H |
| 117 | 4-ClC₆H₄ | 5-C₆H₅-2-C₅H₃N(CH₂)₂ | CH₂C(Me)₂CH₂ | CN₄H |
| 118* | 4-ClC₆H₄ | 3-C₉H₆N | CH₂C(Me)₂ | CO₂H |
| 119* | 4-ClC₆H₄ | 4-C₉H₆N | CH₂C(Me)₂ | CO₂H |
| 120* | 4-ClC₆H₄ | 2-C₈H₅N₂ | CH₂C(Me)₂ | CO₂H |
| 121 | 4-ClC₆H₄ | 5-(4-ClC₆H₄)-2-C₅H₃N | CH₂C(Me)₂ | CN₄H |
| 122 | 4-ClC₆H₄ | 4-(2-C₅H₄N)C₆H₄ | CH₂C(Me)₂ | CO₂H |
| 123* | 4-ClC₆H₄ | 2-C₄H₃S | CH₂C(Me)₂ | CO₂H |
| 124 | 4-ClC₆H₄ | C₆H₅ | CH₂C(Me)₂ | CO₂H |
| 125 | 4-ClC₆H₄ | C₆H₅(CH₂)₂ | CH₂C(Me)₂ | CO₂H |
| 126* | 4-ClC₆H₄ | 3,5-Me₂-4-C₃NO | CH₂C(Me)₂ | CO₂H |
| 127* | 4-ClC₆H₄ | 2-(4-ClC₆H₄)-4-C₃NS | CH₂C(Me)₂ | CO₂H |
| 128* | 4-ClC₆H₄ | 1-Me-5-C₆H₅-2-C₅H₆N | CH₂C(Me)₂ | CO₂H |
| 129 | 4-ClC₆H₄ | c-Hex | CH₂C(Me)₂ | CO₂H |
| 130 | 4-ClC₆H₄ | C₆H₅(CH₂)₂N(Me)CO | CH₂C(Me)₂ | CO₂H |
| 131* | 4-ClC₆H₄ | 2-C₁₀H₇ | CH₂C(Me)₂ | CO₂H |
| 132* | 4-ClC₆H₄ | 2-C₁₀H₇ | CH₂C(Me)₂CH₂ | CN₄H |
| 133* | 4-ClC₆H₄ | 5-C₆H₅-2-C₃HNO | CH₂C(Me)₂CH₂ | CN₄H |
| 134 | 4-ClC₆H₄ | 5-(4-MeOC₆H₄)-2-C₅H₃N | CH₂C(Me)₂CH₂ | CN₄H |
| 135* | 4-ClC₆H₄ | 5-(1-C₁₀H₇)-2-C₅H₃N | CH₂C(Me)₂CH₂ | CN₄H |
| 136* | 4-ClC₆H₄ | 5-C₆H₅-2-C₄H₂N₂ | CH₂C(Me)₂CH₂ | CN₄H |
| 137* | 4-ClC₆H₄ | 5-C₆H₅-2-C₄H₂N₂ | CH₂C(Me)₂CH₂ | CN₄H |
| 138* | 4-ClC₆H₄ | 2-C₆H₅-5-C₇H₃NO | CH₂C(Me)₂CH₂ | CN₄H |
| 150* | 4-ClC₆H₄ | 3-[C₃H₃NS—C₃H₅(MeO)]—C₆H₄ | CH₂C(Me₂ | CO₂H |
| 151* | 4-ClC₆H₄ | 1-CO₂Me-2-C₁₀H₆ | CH₂C(Me)₂ | CO₂H |
| 152 | 4-ClC₆H₄ | 3-MeO—C₆H₄ | CH₂C(Me)₂ | CO₂H |
| 153 | 3-CF₃C₆H₄ | 5-C₆H₅-2-C₅H₃N | CH₂C(Me)₂CH₂ | CO₂H |
| 154 | 3-CF₃C₆H₄ | 5-C₆H₅-2-C₅H₃N | CH₂C(Me)₂CH₂ | CN₄H |
| 155 | 3-ClC₆H₄ | 5-C₆H₅-2-C₅H₃N | CH₂C(Me)₂CH₂ | CONHS(O)₂Me |
| 156 | 4-ClC₆H₄ | 5-C₆H₅-2-C₅H₃N | CH₂C(Me)₂CH₂ | CONH₂ |
| 157 | 2-ClC₆H₄ | 5-C₆H₅-2-C₅H₃N | CH₂C(Me)₂CH₂ | CN₄H |
| 158 | 2-ClC₆H₄ | 5-C₆H₅-2-C₅H₃N | CH₂C(Me)₂CH₂ | CO₂H |
| 159 | 2,4-Cl₂C₆H₃ | 5-C₆H₅-2-C₅H₃N | CH₂C(Me)₂CH₂ | CN₄N |
| 160 | 3,4-Cl₂C₆H₃ | 5-C₆H₅-2-C₅H₃N | CH₂C(Me)₂CH₂ | CO₂H |
| 161 | 4-ClC₆H₄ | 5-C₆H₅-2-C₅H₃N | CH₂C(Me)₂CH₂ | CONHCN₄H |
| 162 | 4-ClC₆H₄ | 5-C₆H₅-2-C₅H₃N | CH₂C(Me)₂CH₂ | CON(OH)Me |
| 163 | 4-ClC₆H₄ | 5-C₆H₅-2-C₅H₃N | CH₂C(Me)₂CH₂ | CONHCN |
| 164* | 2-C₁₀H₇ | 5-C₆H₅-2-C₅H₃N | CH₂C(Me)₂CH₂ | CO₂H |
| 165* | 3-(4-MeO-4-C₅H₈O)—C₆H₄ | 5-C₆H₅-2-C₅H₃N | CH₂C(Me)₂CH₂ | CO₂H |
| 166 | C₆F₅ | 5-C₆H₅-2-C₅H₃N | CH₂C(Me)₂CH₂ | CO₂H |

TABLE 1-continued

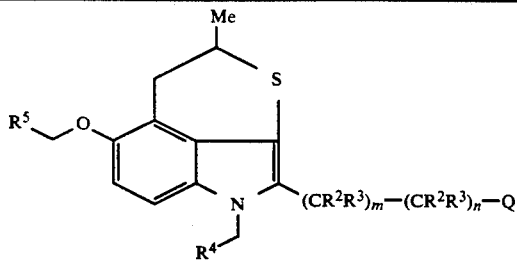

Ib

| Ex. No. | R⁴ | R⁵ | $(CR^2R^3)_m$—$(CR^2R^3)_n$ | Q |
|---|---|---|---|---|
| 167* | 3-C₄H₈NO—C₆H₄ | 5-C₆H₅-2-C₅H₃N | CH₂C(Me)₂CH₂ | CO₂H |
| 168* | 4-(4-HO-4-C₅H₈O)—C₆H₄ | 5-C₆H₅-2-C₅H₃N | CH₂C(Me)₂CH₂ | CO₂H |
| 169* | 4-MeO-3-(4-HO-4-C₅H₈O)—C₆H₄ | 5-C₆H₅-2-C₅H₃N | CH₂C(Me)₂CH₂ | CO₂H |
| 170* | 4-(4-EtO-4-C₅H₈O)—C₆H₄ | 5-C₆H₅-2-C₅H₃N | CH₂C(Me)₂CH₂ | CO₂H |
| 171* | 4-(4-MeO-4-C₅H₈O)—C₆H₄ | 5-C₆H₅-2-C₅H₃N | CH₂C(Me)₂CH₂ | CO₂H |
| 172 | 4-ClC₆H₄ | 5-C₆H₅-2-C₅H₃N | (CH₂)₂CHMe | CO₂H |

TABLE 2

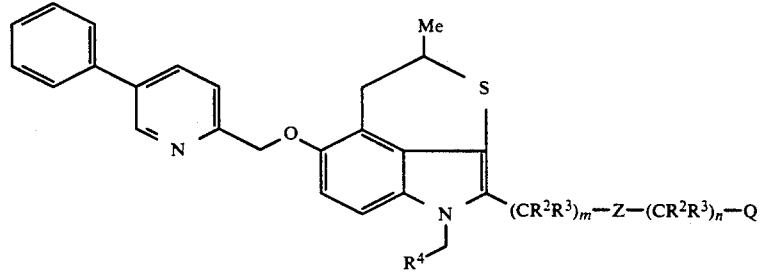

Ic

| Ex. No. | R⁴ | $(CR^2R^3)_m$ | Z | $(CR^2R^3)_n$ | Q |
|---|---|---|---|---|---|
| 68 | 4-ClC₆H₄ | CH₂ | O | CH₂ | CO₂H |
| 69 | 4-ClC₆H₄ | CH₂ | O | CH(Me) | CO₂H |
| 70 | 4-ClC₆H₄ | CH₂ | S | CH₂ | CO₂H |
| 71 | 4-ClC₆H₄ | CH₂ | S | (CH₂)₂ | CO₂H |
| 72 | 4-ClC₆H₄ | CH₂ | S | CH₂CH(Et) | CO₂H |
| 73 | 4-ClC₆H₄ | CH₂ | S | CH₂CH(Et) (S) isomer | CO₂H |
| 74 | 4-ClC₆H₄ | CH₂ | S | CH₂CH(Et) (R) isomer | CO₂H |
| 75 | 4-ClC₆H₄ | CH₂ | S | CH₂CH(Me) | CO₂H |
| 76 | 4-ClC₆H₄ | CH₂ | S | CH₂CH(OMe) | CO₂H |
| 77 | 4-ClC₆H₄ | CH₂ | S | C(Me)₂CH₂ | CO₂H |
| 78 | 4-ClC₆H₄ | CH₂ | S | CH₂C(Me)₂ | CO₂H |
| 79 | 4-ClC₆H₄ | CH₂ | O | (CH₂)₂ | CN₄H |
| 80 | 4-ClC₆H₄ | (CH₂)₂ | O | CH₂ | CO₂H |
| 81 | 4-ClC₆H₄ | (CH₂)₂ | O | CH₂ | CN₄H |
| 82 | 4-ClC₆H₄ | (CH₂)₂ | O | CH(Me) | CO₂H |
| 83 | 4-ClC₆H₄ | (CH₂)₂ | O | CH(Me) | CN₄H |
| 84 | 4-ClC₆H₄ | (CH₂)₂ | S | CH(Me) | CO₂H |
| 85 | 4-ClC₆H₄ | (CH₂)₂ | O | (CH₂)₂ | CO₂H |
| 86 | 4-ClC₆H₄ | (CH₂)₂ | O | (CH₂)₂ | CN₄H |
| 87 | C₆H₅ | (CH₂)₂ | O | CH(Me) | CO₂H |
| 173 | 3-ClC₆H₄ | (CH₂)₂ | O | CH(Me) | CO₂H |
| 174 | 3-ClC₆H₄ | (CH₂)₂ | O | CH(Et) | CO₂H |
| 175 (racemic) | 4-ClC₆H₄ | (CH₂)₂ | O | CH(Et) | CO₂H |
| 176 (isomer 1) | 4-ClC₆H₄ | (CH₂)₂ | O | CH(Et) | CO₂H |
| 177 (isomer 2) | 4-ClC₆H₄ | (CH₂)₂ | O | CH(Et) | CO₂H |
| 178 (isomer 3) | 4-ClC₆H₄ | (CH₂)₂ | O | CH(Et) | CO₂H |
| 179 (isomer 4) | 4-ClC₆H₄ | (CH₂)₂ | O | CH(Et) | CO₂H |
| 180 | 4-ClC₆H₄ | (CH₂)₂ | O | C(Me)₂ | CO₂H |
| 181 | 4-ClC₆H₄ | (CH₂)₂ | O | CH(Me) | CONHS(O)₂Me |
| 182 (racemic) | 4-ClC₆H₄ | (CH₂)₂ | O | CH(Et) | CONHS(O)₂Me |
| 183 (isomer 1) | 4-ClC₆H₄ | (CH₂)₂ | O | CH(Et) | CONHS(O)₂Me |
| 184 | 4-ClC₆H₄ | (CH₂)₂ | O | CH(Et) | CONHS(O)₂Me |

TABLE 2-continued

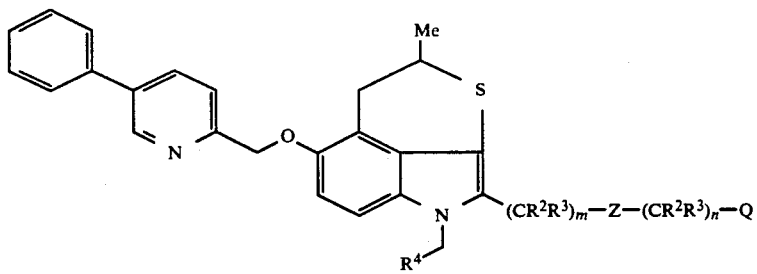

Ic

| Ex. No. | R⁴ | (CR²R³)ₘ | Z | (CR²R³)ₙ | Q |
|---|---|---|---|---|---|
| (isomoer 2) | | | | | |
| 185 | 4-ClC₆H₄ | (CH₂)₂ | O | CH(Et) | CONHS(O)₂Ph |
| 186 | 4-ClC₆H₄ | (CH₂)₂ | S | CH₂CH(Et) | CO₂H |
| 187 | 4-ClC₆H₄ | CH₂ | O | (CH₂)₂ | CO₂H |
| 188 | 4-ClC₆H₄ | CH₂ | O | CH(Me)CH₂ | CO₂H |
| 189 | 4-ClC₆H₄ | CH₂ | O | CH(Et)CH₂ | CO₂H |
| 190 | 4-ClC₆H₄ | (CH₂)₂ | O | CH(Me)CH₂ | CO₂H |
| 191 | 4-ClC₆H₄ | CH₂ | S | CH(Me)CH₂ | CO₂H |
| 192 | 4-ClC₆H₄ | CH₂ | S | CH₂CH(Et) | CONHS(O)₂Me |
| 193 | 4-ClC₆H₄ | CH₂ | NH | (CH₂)₂ | CO₂H |
| 194 | 4-ClC₆H₄ | (CH₂)₂ | NH | CH(Me) | CO₂H |
| 195 | 4-ClC₆H₄ | — | S | CH(Me)CH₂ | CO₂H |
| 196 | 4-ClC₆H₅ | — | CON(Me) | CH₂ | CO₂H |
| 197 | 4-ClC₆H₅ | CH₂ | CON(Me) | CH₂ | CO₂H |
| 198 | 4-ClC₆H₅ | CH₂ | CON(Me) | CH(Me) | CO₂H |
| 199 | 4-ClC₆H₅ | CH₂ | CON(Me) | CH[CH(Me)₂] | CO₂H |
| 200 | 4-ClC₆H₅ | CH₂ | CON(Me) | CH[CH₂CH(Me)₂] | CO₂H |
| 201 | 4-ClC₆H₅ | CH₂ | CON(Me) | CH(CH₂Ph) | CO₂H |
| 220 | 4-ClC₆H₅ | (CH₂)₂ | N(COMe) | CH(Me) | CO₂H |
| 221 | 4-ClC₆H₅ | (CH₂)₂ | N[S(O)₂Me] | CH(Me) | CO₂H |

TABLE 3

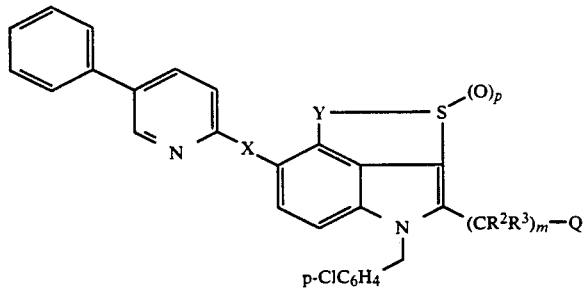

Id

| Ex. No. | p | X | Y | (CR²R³)ₘ | Q |
|---|---|---|---|---|---|
| 88 | 0 | CH₂O | CH₂C(Me)₂ | CH₂C(Me)₂ | CO₂H |
| 91 | 0 | CH₂O | (CH₂)₂ | CH₂C(Me)₂ | CO₂H |
| 92 | 0 | CH₂O | CH₂CH(Et) | CH₂C(Me)₂ | CO₂H |
| 93 | 0 | CH₂O | CH₂CH(n-Pr) | CH₂C(Me)₂ | CO₂H |
| 139 | 2 | CH₂O | CH₂CH(Me) | CH₂C(Me)₂ | CO₂H |
| 140 Mixture | 1 | CH₂O | CH₂CH(Me) | CH₂C(Me)₂ | CO₂H |
| 141 (R*, S*) | 1 | CH₂O | CH₂CH(Me) | CH₂C(Me)₂ | CO₂H |
| 142 (R*, R*) | 1 | CH₂O | CH₂CH(Me) | CH₂C(Me)₂ | CO₂H |
| 143 | 0 | CH₂O | CH=CHCH₂ | CH₂C(Me)₂ | CO₂H |
| 144 | 0 | CH₂O | (CH₂)₃ | CH₂C(Me)₂ | CO₂H |
| 145 | 0 | CH₂S | CH₂CH(Me) | CH₂C(Me)₂ | CO₂H |
| 146 | 0 | CH₂S | CH₂CH(Me) | CH₂C(Me)₂CH₂ | CO₂H |
| 147 | 0 | CH₂S | CH₂CH(Me) | CH₂C(Me)₂CH₂ | CN₄H |
| 148 | 0 | CH₂OCH₂ | CH₂CH(Me) | CH₂C(Me)₂CH₂ | CN₄H |
| 149 | 0 | (CH₂)₂ | CH₂CH(Me) | CH₂C(Me)₂CH₂ | CN₄H |
| 202 | 0 | CHCH (E-isomer) | CH₂CH(Me) | CH₂C(Me)₂CH₂ | CN₄H |
| 203 | 0 | O | CH₂CH(Me) | CH₂C(Me)₂CH₂ | CN₄H |
| 204 | 0 | S | CH₂CH(Me) | CH₂C(Me)₂CH₂ | CN₄H |
| 205 | 0 | CH₂O | CH=C(Me) | CH₂C(Me)₂ | CO₂H |
| 206 | 0 | CH₂O | CH=C(Me) | CH₂C(Me)₂CH₂ | CN₄H |

TABLE 3-continued

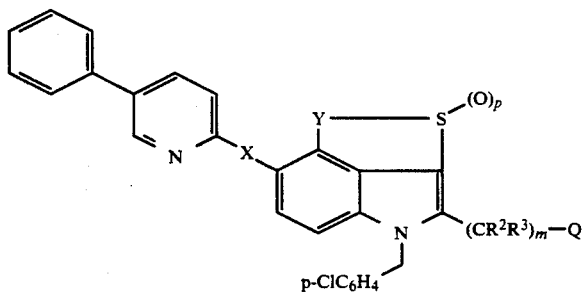

Id

| Ex. No. | p | X | Y | $(CR^2R^3)_m$ | Q |
|---|---|---|---|---|---|
| 207++ | 0 | $CH_2O$ | $CH=C(Me)$ | $CH_2C(Me)_2$ | $CO_2H$ |

++N-substituent on indole ring is $3\text{-}F\text{-}C_6H_4\text{-}CH_2\text{-}$

TABLE 4

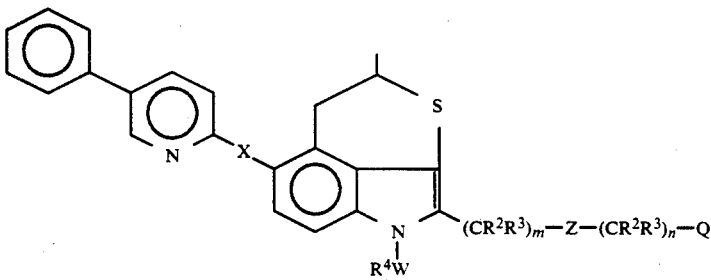

| Ex. No. | X | $R^4W$ | $(CR^2R^3)_m\text{-}Z\text{-}(CR^2R^3)_n$ | Q |
|---|---|---|---|---|
| 208 | $CH_2O$ | $C_6H_5CO$ | $CH_2C(Me)_2$ | $CO_2H$ |
| 209 | $CH_2O$ | $C_6H_5S(O)_2$ | $CH_2C(Me)_2CH_2$ | $CN_4H$ |
| 210 | $(CH_2)_2$ | $C_6H_5CH_2$ | $CH_2C(Me)_2CH_2$ | $CO_2H$ |
| 211 | $(CH_2)_2$ | $3\text{-}FC_6H_4CH_2$ | $CH_2C(Me)_2CH_2$ | $CO_2H$ |
| 212 | $(CH_2)_2$ | $3\text{-}FC_6H_4CH_2$ | $CH_2C(Me)_2CH_2$ | $CN_4H$ |
| 213 | $(CH_2)_2$ | $3\text{-}FC_6H_4CH_2$ | $CH_2C(Me)_2CH_2$ | $CONHS(O)_2Me$ |
| 214 | $(CH_2)_2$ | $4\text{-}ClC_6H_4CH_2$ | $(CH_2)_2OCH(Me)$ | $CO_2H$ |
| 215 | $CH=CH$ (E-isomer) | $4\text{-}ClC_6H_4CH_2$ | $(CH_2)_2OCH(Et)$ | $CO_2H$ |
| 216 | $CH_2O$ | $4\text{-}ClC_6H_4CH_2$ | $COC(Me)_2CH_2$ | $CN_4H$ |
| 217 | $CH_2O$ | $4\text{-}ClC_6H_4CH_2$ | $CH(OMe)C(Me)_2CH_2$ | $CN_4H$ |
| 218 | $CH_2O$ | $4\text{-}ClC_6H_4CH_2$ | $CH=CHCH_2$ (E-isomer) | $CO_2H$ |
| 219 | $CH_2O$ | $4\text{-}ClC_6H_4CH_2$ | $CH=CHCH(Me)$ (E-isomer) | $CO_2H$ |

In Tables 1-4, the substituent formulas correspond to the following chemical names:

| | |
|---|---|
| +2,3,4,5 or $6\text{-}C_6H_5\text{-}2,3$ or $4\text{-}C_5H_3N$ | 2,3,4,5 or 6-phenylpyridin-2,3 or 4-yl |
| 2,3 or $4\text{-}C_5H_4N$ | pyridin-2,3 or 4-yl |
| $CN_4H$ | 1H (or 2H)-tetrazol-5-yl |
| *Ex 12: $3,4\text{-}CH_2O_2C_6H_3$ | 3,4-methylenedioxyphenyl |
| Ex 20: $2\text{-}C_4H_3S$ | thien-2-yl |
| Ex 22: $2\text{-}C_9H_6N$ | quinolin-2-yl |
| Ex 24: $1\text{-}C_{10}H_{15}CH_2$ | 1-adamantylmethyl |
| Exs 94, 95: $5\text{-}C_6H_5\text{-}2\text{-}C_5H_3N(O)$ | 5-phenyl-1-oxopyridin-2-yl |
| Ex 96: See Ex 22 | |
| Ex 97: $2\text{-}C_9H_6N(O)$ | 1-oxoquinolin-2-yl |
| Ex 118: $3\text{-}C_9H_6N$ | isoquinolin-3-yl |
| Ex 119: $4\text{-}C_9H_6N$ | quinolin-4-yl |
| Ex 120: $2\text{-}C_8H_5N_2$ | 1,8-naphthyridin-2-yl |
| Ex 123: See Ex 20 | |
| Ex 126: $3,5\text{-}(Me)_2\text{-}4\text{-}C_3NO$ | 3,5-dimethyloxazol-4-yl |
| Ex 127: $2\text{-}(4\text{-}ClC_6H_4)\text{-}4\text{-}C_3NS$ | 2-(4-chlorophenyl)thiazol-4-yl |
| Ex 128: $1\text{-}Me\text{-}5\text{-}C_6H_5\text{-}2\text{-}C_5H_6N$ | 1-methyl-5-phenyl-1,2,3,4-tetrahydropyridin-2-yl |
| Exs 131, 132: $2\text{-}C_{10}H_7$ | naphth-2-yl |
| Ex 133: $5\text{-}C_6H_5\text{-}2\text{-}C_3HNO$ | 5-phenyloxazol-2-yl |
| Ex 135: $5\text{-}(1\text{-}C_{10}H_7)\text{-}2\text{-}C_5H_3N$ | 5-(1-naphthyl)pyridin-2-yl |
| Ex 136: $5\text{-}C_6H_5\text{-}2\text{-}C_4H_2N_2$ | 5-phenylpyrazin-2-yl |

| -continued | |
|---|---|
| +2,3,4,5 or 6-$C_6H_5$-2,3 or 4-$C_5H_3N$ | 2,3,4,5 or 6-phenylpyridin-2,3 or 4-yl |
| 2,3 or 4-$C_5H_4N$ | pyridin-2,3 or 4-yl |
| $CN_4H$ | 1H (or 2H)-tetrazol-5-yl |
| Ex 137: 5-$C_6H_5$-2-$C_4H_2N_2$ | 5-phenylpyrimidin-2-yl |
| Ex 138: 2-$C_6H_5$-5-$C_7H_3NO$ | 2-phenylfuro[3,2-b]pyridin-5-yl |
| Ex 150: 3-[$C_3H_3NS$-$C_3H_5$(MeO)]-$C_6H_4$ | 3-[1-methoxy-1-(thiazol-2-yl)prop-1-yl]phenyl |
| Ex 151: 1-$CO_2Me$-2-$C_{10}H_6$ | 1-carbomethoxynaphth-2-yl |
| Ex 164: See Ex 131 | |
| Ex 165: 3-(4-MeO-4-$C_5H_8O$)-$C_6H_4$ | 3-(4-methoxytetrahydropyran-4-yl)phenyl |
| Ex 167: 3-$C_4H_8NO$-$C_6H_4$ | 3-(N-morpholino)phenyl |
| Ex 168: 4-(4-HO-4-$C_5H_8O$)-$C_6H_4$ | 4-(4-hydroxytetrahydropyran-4-yl)phenyl |
| Ex 169: 4-MeO-3-(4-HO-4-$C_5H_8O$)-$C_6H_4$ | 4-methoxy-3-(4-hydroxytetrahydropyran-4-yl)phenyl |
| Ex 170: 4-(4-EtO-4-$C_5H_8O$)-$C_6H_4$ | 4-(4-ethoxytetrahydropyran-4-yl)phenyl |
| Ex 171: 4-(4-MeO-4-$C_5H_8O$)-$C_6H_4$ | 4-(4-methoxytetrahydropyran-4-yl)phenyl |

Assays for Determining Biological Activity

Compounds of Formula I can be tested using the following assays to determine their mammalian leukotriene biosynthesis inhibiting activity.

Human 5-Lipoxygenase Inhibitor Screen

Objective of the Assay: The objective of the assay is to select agents which specifically inhibit the activity of human 5-lipoxygenase using a 100,000×g supernatant fraction prepared from insect cells infected with recombinant baculovirus containing the coding sequence for human 5-lipoxygenase. Enzyme activity is measured spectrophotometrically from the optimal rate of conjugated diene formation ($A_{234}$) measured after the incubation of the enzyme with arachidonic acid in the presence of ATP, calcium ions and phosphatidylcholine.

Description of Procedure: The activity of 5-lipoxygenase is measured using a spectrophotometric assay and recombinant human 5-lipoxygenase as a source of enzyme. The 100,000×g fraction from S19 cells infected with the recombinant baculovirus rvH5LO(8-1) containing the coding region sequence for human 5-lipoxygenase is prepared as described below. The enzymatic activity is measured, using a spectrophotometric assay from the optimal rate of conjugated diene formation ($A_{234}$) using the procedure described by Riendeau et al. (Biochem. Pharmacol., 38, 2313-2321, 1989) with minor modifications. The incubation mixture contains 50 mM sodium phosphate pH 7.4, 0.2 mM ATP, 0.2 mM $CaCl_2$, 20 μM arachidonic acid (5 μl from a 100-fold concentrated solution in ethanol), 12 μg/ml phosphatidylcholine, an aliquot of the 100,000×g fraction (2-10 μl) and inhibitor (0.5 ml final volume). Inhibitors are added as 500-fold concentrated solutions in DMSO. Reactions are initiated by the addition of an aliquot of the enzyme preparation and the rate of conjugated diene formation is followed for 2 minutes at room temperature. The reactions are performed in semi-micro cuvettes (0.7 ml capacity, 10 mm path length and 4 mm internal width) and the absorbance changes are recorded with a Hewlett-Packard diode array spectrophotometer (HP 8452A) connected to the ChemStation using UV/VIS Kinetics Software. Enzymatic activity is calculated from the optimal rate of the reaction by a linear fit of the variation of $A_{234}$ during the first twenty seconds using the least square method for the equation $A_{234}=V_ot+A_o$ where $V_o$ is the rate, t is the time, and $A_o$ is the absorbance at zero time. The results are expressed as percentages of inhibition of the reaction rate relative to controls (typically between 0.15-0.21 AU/min) containing the DMSO vehicle.

Preparation of Lysates from Infected Cells: S19 cells are grown at 27° C. in 100 ml spinner flasks to a cell density of 1.5-2×10$^6$ cells/ml and infected for 44-48 hours with rvH5LO(8-1). The cells are then collected by centrifugation (900×g for 10 min, at 20° C.), washed twice with Dulbacco's phosphate-buffered saline (pH 7.4) (25 ml/2×10$^8$ cells) and resuspended at 1.2×10$^7$ cells/ml in a homogenization buffer containing 50 mM potassium phosphate (pH 7.9) 2 mM EDTA, 1 mM dithiothreitol, 0.5 mM phenylmethylsulfonyl fluoride and 60 μg/ml soybean trypsin inhibitor. The cells are then lysed by sonication at 4° C. using a Cole Parmer (4710 Series) Ultrasonic homogeniser (3 to 5 bursts of 10 sec. with 30-sec. lags, pulse mode, 70% duty cycle, and output setting at 3). The preparation are examined under the microscope to achieve efficient cell lysis (>90%) with minimal sonication. The lysate is then centrifuged at 100,000×g for 1 hour (Beckman L5-65, 60 Ti rotor) at 4° C. and the resulting supernatant (S-100 fraction) brought to 24 μg/ml PC by the addition of a 250-fold concentrated solution in ethanol. The S-100 fraction (1-3 mg/ml) is stable for several hours at 4° C. and can be stored for several months at −70° C. in 20% ethylene glycol with about 50% recovery of activity.

Determination of Inhibition of Rat 5-Lipoxygenase

The activity of 5-lipoxygenase was measured from the conversion of [$^{14}$C]-arachidonic acid to 5-HETE and 5,12-diHETEs catalyzed by the 10,000×g supernatant fraction from rat PMN leukocytes, using the procedure of Riendeau and Leblanc (Biochem. Biophys. Res. Commun., 141, 534-540, 1986) with minor modifications. The incubation mixture contained 25 mM Na$^+$/K$^+$ phosphate buffer, pH 7.3, 1 mM ATP, 0.5 mM $CaCl_2$, 0.5 mM mercaptoethanol and an aliquot of the enzyme preparation in a final volume of 0.2 ml. The enzyme was pre-incubated with the inhibitor for 2 min at 37° C. before initiation of the reaction with the addition of 2 ml of [$^{14}$C]-arachidonic acid (25,000 DPM) in ethanol to obtain a final concentration of 10 mM. Inhibitors were added as 500-fold concentrated solutions in DMSO. After incubation for 10 min at 37° C., the reaction was stopped by adding 0.8 mL of diethyl ether/methanol/1M citric acid (30:4:1). The samples were centrifuged at 1,000×g for 5 min and the organic phases analyzed by TLC on Baker Si250F-PA or Whatman silica gel 60A LKGF plates using diethyl ether/petroleum ether/acetic acid (50:50:1) as solvent. The amount of radioactivity migrating at the positions of arachidonic acid, 5-HETE and 5,12-diHETEs was determined using a Berthold TLC analyzer LB 2842. The activity of 5-lipoxygenase was calculated from the percentage of conversion of arachidonic acid to 5-HETE and 5,12-diHETEs after the 10 min. incubation.

Human Polymorphonuclear (PMN) Leukocyte LTB$_4$ Assay

A. Preparation of Human PMN.

Human blood was obtained by antecubital venepuncture from consenting volunteers who had not taken medication within the previous 7 days. The blood was immediately added to 10% (v/v) trisodium citrate (0.13M) or 5% (v/v) sodium heparin (1000 IU/mL). PMNs were isolated from anticoagulated blood by dextran sedimentation of erythrocytes followed by centrifugation through Ficoll-Hypaque (specific gravity 1.077), as described by Boyum, A. *Scand. J. Clin. Lab. Invest.* 1968, 21 (Supp 97), 77. Contaminating erythrocytes were removed by lysis following exposure to ammonium chloride (0.16M) in Tris buffer (pH 7.65), and the PMNS resuspended at $5 \times 10^5$ cells/mL in HEPES (15 mM)-buffered Hanks balanced salt solution containing $Ca^{2+}$ (1.4 mM) and $Mg^{2+}$ (0.7 mM), pH 7.4. Viability was assessed by Trypan blue exclusion and was typically greater than 98%.

B. Generation and Radioimmunoassay of LTB$_4$.

PMNs (0.5 mL; $2.5 \times 10^5$ cells) were placed in plastic tubes and incubated (37° C., 2 min) with test compounds at the desired concentration or vehicle (DMSO, final concentration 0.2%) as control. The synthesis of LTB$_4$ was initiated by the addition of calcium ionophore A23187 (final concentration 10 mM) or vehicle in control samples and allowed to proceed for 5 minutes at 37° C. The reactions were then terminated by the addition of cold methanol (0.25 mL) and samples of the entire PMN reaction mixture were removed for radioimmunoassay of LTB$_4$.

Samples (50 mL) of authentic LTB$_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer were added to reaction tubes. Thereafter [$^3$H]-LTB$_4$ (10 nCi in 100 mL RIA buffer) and LTB$_4$-antiserum (100 mL of a 1:3000 dilution in RIA buffer) were added and the tubes vortexed. Reactants were allowed to equilibrate by incubation overnight at 4° C. To separate antibody-bound from free LTB$_4$, aliquots (50 mL) of activated charcoal (3% activated charcoal in RIA buffer containing 0.25% Dextran T-70) were added, the tubes vortexed, and allowed to stand at room temperature for 10 minutes prior to centrifugation ($1500 \times$ g; 10 min; 4° C.). The supernatants containing antibody-bound LTB$_4$ were decanted into vials and Aquasol 2 (4 mL) was added. Radioactivity was quantified by liquid scintillation spectrometry. Preliminary studies established that the amount of methanol carried into the radioimmunoassay did not influence the results. The specificity of the antiserum and the sensitivity of the procedure have been described by Rokach et al., *Prostaglandins Leukotrienes and Medicine* 1984, 13, 21. The amount of LTB$_4$ produced in test and control (approx. 20 ng/$10^6$ cells) samples were calculated. Inhibitory dose-response curves were constructed using a four-parameter algorithm and from these the IC$_{50}$ values were determined.

Human Whole Blood Assay in Vitro for LTB$_4$ Production

A. Blood

Blood (60 ml) is collected from male volunteers directly into 10 ml heparinized vacutainers for assay; one volunteer per assay.

B. Test Compounds

Stock solution: Most concentrated working solution (final) multiplied by the dilution factor (volume of compound vs blood volume); e.g., 60 μM dose $\times$ 500 (DMSO 1/500)=30 mM stock solution. To calculate the amount of compound needed to make stock solution: mol. wt. of drug $\times$ 1/1000 $\times$ stock concentration; e.g., $618 \times 1/1000 \times 30$ mM=18.54 mg for 1 ml vehicle either DMSO or methanol.

Working Solutions: Serial dilutions of stock with appropriate vehicle. If methanol is used to dissolve compound, then use methanol/BSA solution to dilute the stock. Methanol/BSA = 1 ml 100% methanol = 9 ml BSA 1 mg/ml saline.

Effective conc. in the assay depends upon the test compound (may be 60 uM to 0.1 uM). 1/500 dilution for DMSO vehicle = 1 μl for 500 μl blood. 1/50 dilution for MeOH/BSA = 10 μl for 500 μl blood.

C. A23187

50 mM stock solution: 50 mg A23187 for 1.9 ml DMSO in 50 μl aliquots (stored at −20° C.).

Working Solution: 40 μl of 50 mM stock + 760 μl homologous plasma = 2.5 mM solution vehicle = plasma.

Effective conc. in assay should be 25 μM (1/100 dilution).

D. Assay

Add 1 μl (DMSO) of 10 μl (MeOH/BSA) of either test compound or vehicle (use 10 μl hamilton syringe to deliver 1–10 μl) to properly labelled 1.5 ml Eppendorf tubes. 500 μl of blood is dispensed into each tube, which is then vortexed, transfered to a plastic box with lid, washed outside with methanol and incubated 15 min. at 37° C. Meanwhile, centrifuge ~2 ml blood in microfuge at 12,000 $\times$ g for 5 minutes to obtain plasma for the A23187 solution. At the end of the 15 minutes incubations, add 5 μl of the 2.5 mM A23187 working solution or 5 μl of plasma (blanks) into each tube. Vortex well and incubate for 30 minutes at 37° C. At the end of the last incubation, the plasma is obtained by centrifugation as described above, and a 100 μl aliquot is placed into 400 μl of 100% methanol. Meanwhile, transfer the remaining 150 μl of plasma into a clean Eppendorf tube and the store at −70° C. The samples are vortexed and centrifuged as before. The supernatant (methanol extract) is stored at −70° C. until RIA for LTB$_4$ (20 μl aliquot) as in the above human PMN assay.

| SAMPLES | | |
|---|---|---|
| 2 blanks | = 500 μl blood + 1 or 10 μl vehicle | + 5 μl plasma |
| 4 controls | = 500 μl blood + 1 or 10 μl vehicle | + 5 μl A23187 |
| 2 drug blanks | = 500 μl blood + 1 or 10 μl highest conc. of drug | + 5 μl plasma |
| X drugs | = 500 μl blood + 1 or 10 μl drug | + 5 μl A23187 |

Asthmatic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate was supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mg/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65 HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or Ascaris antigen.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., Prostaglandins, 28:173-182, 1984, and McFarlane, C. S. et al., Agents Actions 22:63-68, 1987.)

Prevention of Induced Bronchoconstriction in Allergic Sheep

A. Rationale.

Certain allergic sheep with known sensitivity to a specific antigen (Ascaris suum) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods.

Animal Preparation:

Adult sheep with a mean weight of 35 kg (range, 18 to 50 kg) are used. All animals used meet two criteria: a) they have a natural cutaneous reaction to 1:1,000 or 1:10,000 dilutions of Ascaris suum extract (Greer Diagnostics, Lenois, N.C.) and b) they have previously responded to inhalation challenge with Ascaris suum with both an acute bronchoconstriction and a late bronchial obstruction (Abraham, W. M. Delehunt, J. C., Yerger, L. and Merchette, B., Am. Rev. Resp. Dis., 1983, 128, 839-44).

Measurement of Airway Mechanics:

The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one ml of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). Testing of the pressure transcuder catheter system reveals no phase shift between pressure and flow to a frequency of 9 Hz. For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10-15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems:

Aerosols of Ascaris suum extract (1:20) are generated using a disposable medicalnebulizer (Raindrop ®, Puritan Bennett), which produces an aerosol with a mass median aerodynamic diameter of 6.2 µM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is connected to the inspiratory part of a Harvard respirator. The aerosol is delivered at a tidal volume of 500 ml of a rate of 20 per minute. Thus, each sheep receives an equivalent dose of antigen in both placebo and drug trials.

Experimental Protocol:

Prior to antigen challenge baseline measurements of $SR_L$ are obtained, infusion of the test compound is started 1 hr prior to challenge, the measurement of $SR_L$ repeated and then the sheep undergoes inhalation challenge with Ascaris suum antigen. Measurements of $SR_L$ are obtained immediately after antigen challenge and at 1, 2, 3, 4, 5, 6, 6.5, 7, 7.5, and 8 hrs after antigen challange. Placebo and drug tests are separated by at least 14 days. In a further study, sheep are given a bolus dose of the test compound followed by an infusion of the test compound for 0.5-1 hr prior to Ascaris challenge and for 8 hrs after Ascaris as described above.

Statistical Analysis:

A Kruskal-Wallis one way ANOVA test is used to compare the acute immediate responses to antigen and the peak late response in the controls and the drug treated animals.

PREPARATION OF HYDRAZINES

Hydrazine 1: 1-(4-Chlorobenzyl)-1-(4-allyloxyphenyl)hydrazine

Step 1: 4-Allyloxyphenylhydrazine Hydrochloride

To a suspension of 4-allyloxyaniline hydrochloride (100 g) (Bull. Soc. Chim, France 2154-2157 (1962) in H2O (1.4L), cooled to 0° C., was added dropwise a solution of NaNO2 in H2O (40 g/100 mL) and stirred for 15 minutes. The resulting cold diazonium salt was then cannulated into a stirred cold solution of Na2S2O4 in H2O (516 g/3L) and Et2O (3L). The addition completed, the reaction mixture was stirred for 30 minutes and basified with 10N NaOH (540 mL). The Et2O layer was decanted, washed with brine, dried over Na2SO4 and HCl gas was passed through the ether solution to form the hydrochloride salt which precipitated out. After filtration, the pure final product was obtained.

Step 2: 1-(4-Chlorobenzyl)-1-(4-allyloxyphenyl)hydrazine

To a suspension of the hydrazine of Step 1 (70 g) in toluene (1.2L) was added Et3N (107 mL) followed by 4-chlorobenzyl chloride (61 g). The resulting mixture was heated at reflux for 2 hours. The reaction mixture was cooled and Et2O (1.2L) was added. The triethylammonium hydrochloride salt was filtered off, and the filtrate concentrated under vacuum. The crude residue was purified by chromatography on a bed of silica gel eluting with hexane-EtOAc (6:4) to afford the pure title product as an oil.

Hydrazine 2: 1-Benzyl-1-(4-allyloxyphenyl)hydrazine

Following the procedure described for hydrazine 1, Step 2, but substituting benzyl chloride for 4-chlorobenzyl chloride as starting material, the title compound was obtained as an oil.

PREPARATION OF KETONES III

Ketone 1: Methyl 6-t-butylthio-2,2-dimethyl-5-oxohexanoate

Step 1: Dimethyl 2,2-dimethylglutarate 2,2-Dimethylglutaric anhydride (10 g) was dissolved in MeOH (200 mL) with 5 drops of conc. H2SO4 and heated to 50° C. under nitrogen for 24 hours. The mixture was cooled, the solvent removed and the residue taken up in Et2O. Filtration of the ethereal solution through a pad of silica gel followed by evaporation of the solvent gave the title compound as an oil.

Step 2: Methyl 4-carboxy-2,2-dimethylbutyrate

The diester from Step 1 (13.0 g), K2CO3 (19.1 g), MeOH (120 mL), THF (80 mL) and H2O (80 mL) were stirred at room temperature for 2 days. The organic solvent was removed in vacuo, the residue poured onto H2O and extracted twice with EtOAc. The aqueous layer was acidified with 3N HCl and extracted with EtOAc (3×). This organic phase was then washed with brine, dried and evaporated to yield the title compound.

Step 3: Methyl 4-(chloroformyl)-2,2-dimethylbutyrate

The acid from Step 2 (7.8 g) was stirred in thionyl chloride (6.5 mL) under a stream of nitrogen for 16 hours. The mixture was azeotroped twice with toluene (2×150 mL) to yield the acid chloride which was used as such for the next step.

Step 4: Methyl 6-diazo-2,2-dimethyl-5-oxohexanoate

The crude acid chloride from Step 3 was dissolved in Et2O (100 mL) and treated with excess ethereal diazomethane. After 3 hours, the Et2O was removed and the residual oil chromatographed (silica gel; hexane/EtOAc 4:1) to give the title compound contaminated with the ester from Step 2.

Step 5: Methyl 6-chloro-2,2-dimethyl-5-oxohexanoate

The diazoketone from Step 4 was dissolved in Et2O and dry HCl gas bubbled into the solution until the diazoketone had completely reacted (as monitored by tlc). The reaction mixture was partitioned between H2O and Et2O and the Et2O layer was then washed with brine, dried and evaporated to provide the title compound which was used without purification for the next step.

Step 6: Methyl 6-t-butylthio-2,2-dimethyl-5-oxohexanoate

A solution of the α-chloroketone (1 eq) from Step 5, 2-methyl-2-propanethiol (1.2 eq), Et3N (1.5 eq) and n-Bu4NBr (catalytic amount) in THF at room temperature under nitrogen was stirred for 24 hours. The mixture was filtered and the solvent removed in vacuo. Chromatography of the oily residue on silica gel (hexane/EtOAc 10:1) provide the title compound as an oil.

Ketone 2: Ethyl t-butylthiopyruvate

Following the procedure described for ketone 1, Step 6, but substituting ethyl bromopyruvate for methyl 6-chloro-2,2-dimethyl-5-oxohexanoate as starting material the title compound was obtained as an oil.

Ketone 3: Ethyl 4-t-butylthioacetoacetate

Following the procedure described for ketone 1, Step 6, but substituting ethyl 4-chloroacetoacetate for methyl 6-chloro-2,2-dimethyl-5-oxohexanoate as starting material the title compound was obtained as an oil.

Ketone 4: Methyl 5-t-butylthio-2,2-dimethyl-4-oxopentanoate

This compound was prepared as described in European Patent Application 275,667 (Jul. 27, 1988).

PREPARATION OF ALKYLATING AGENTS
(Table A)

Halide 19: 3-Cyclohexylpropyl iodide

Using the procedure described in J. Am. Chem. Soc., 90, 6225 (1968), this halide was obtained from 3-cyclohexylpropyl chloride (Aldrich) by displacement of the chloride by NaI.

Halide 20: 2-Thienylmethyl methanesulfonate

Using the procedure described in J. Org. Chem., 35, 3195, (1970), this sulfonate was obtained from 2-thiophene methanol (Aldrich) by mesylation with methanesulfonyl chloride.

Halide 23: 5-Phenyl-2-picolyl chloride

Step 1: 5-Phenyl-2-picoline

A suspension of 100 g of wet Raney Nickel in 1.5L of dodecanol in a three neck round bottom flask equipped with a Dean Stark apparatus was heated until the temperature reached 130° C., then 3-phenylpyridine (Aldrich) was added and the reaction was heated at 190°–200° C. for 6 hours. During the reaction, water was constantly eliminated. When the reaction was over, half of the dodecanol was removed by distillation. After cooling the reaction mixture to room temperature, 200 mL of $H_2O$ and 400 mL of hexane were added, the mixture was shaken and the hexane layer decanted. This process was repeated several times. The combined hexane fractions were washed with 1N HCl until the disappearance of 5-phenyl-2-picoline from the organic phase. The combined aqueous layers were filtered, washed with hexane, basified with 10N NaOH, and extracted with $CH_2Cl_2$. The organic layer was washed with $NH_4OAc$ (25%), dried over $MgSO_4$ and evaporated to dryness. The crude residue was then distilled under vacuum (100° C. at 0.1 mm of Hg) to afford the pure title product.

Step 2: 5-Phenyl-2-picolyl chloride
Method A

To a solution of 6.2 g 5-phenyl-2-picoline in 250 mL of $CCl_4$ were added 5.85 g of N-chlorosuccinimide and 100 mg of benzoylperoxide. The reaction was then heated to reflux and irradiated with a 225 watt lamp for 5 hours. After cooling, $Et_2O$ was added, the solid filtered and the filtrate was evaporated to dryness. The crude residue was chromatographed on silica gel (hexane/EtOAc 9:1) to give the pure title product.

Method B

Step 1: 5-Phenyl-2-picoline N-oxide

To a solution of 100 g 5-phenyl-2-picoline in 170 mL of glacial HOAc was added 30% $H_2O_2$ and the resulting solution was heated at 70° C. overnight. After the reaction mixture was cooled to room temperature, 1 g of 10% Pd/C was added to destroy excess of $H_2O_2$. The reaction mixture was then filtered on celite, washed with toluene and the filtrate was evaporated to dryness affording a yellow solid residue. The crude material was swished with a mixture of $Et_2O/EtOAc$ (10:1) and filtered to afford the pure title product as a white solid, m.p.: 91° C.

Step 2: 5-Phenyl-2-picolyl chloride

To a solution of 75 g 5-phenyl-2-picoline N-oxide from Step 1 in 375 mL of $CH_2Cl_2$ were added simultaneously a solution of 41.5 mL phosphoryl chloride in 150 mL of $CH_2Cl_2$ and a solution of 62 mL $Et_3N$ in 150 mL of $CH_2Cl_2$. The rate of addition was adjusted so that the reaction reached reflux temperature. The addition completed, the reaction was poured into a solution of $NH_4OAc$ (25%), stirred 30 minutes and extracted with EtOAc. The organic layer was dried over $MgSO_4$, filtered on a silica gel bed and evaporated to dryness. The resulting solid was recrystallised from petroleum ether (30°–60° C.) to afford pure title product, m.p.: 73° C. The filtrate was chromatographed on silica gel (hexane/EtOAc 9:1) to give the title product along with 4-chloro-5-phenyl-2-picoline and 6-chloro-5-phenyl-2-picoline.

Halide 24: 2-(1-Adamantyl)ethyl bromide

Using the procedure described in Can. J. Chem., 46, 86, (1968), this bromide was obtained from 2-(1-adamantyl)ethanol (Aldrich) by the conversion of the hydroxyl group to the bromide by carbon tetrabromide with the presence of triphenylphosphine.

Halide 28: 2-Chloromethyl-5-phenylpyridine N-oxide

Following the procedure described in Halide 23, Step 2, Method B, Step 1, but substituting 5-phenyl-2-picolyl chloride (Halide 23) for 5-phenyl-2-picoline as starting material the title compound was obtained as a solid.

Halide 32: 2-Phenyl-3-picolyl chloride

Following the procedure described in Halide 23, Step 2, Method A, but substituting 2-phenyl-3-picoline (Aldrich) for 5-phenyl-2-picoline as starting material the title compound was obtained as a solid.

Halide 39: 6-Chloro-5-phenyl-2-picolyl chloride

Following the procedure described in Halide 23, Step 2, Method B but substituting 6-chloro-5-phenyl-2-picoline (from Halide 23, Step 2, Method B, Step 2) for 5-phenyl-2-picoline as starting material the title compound was obtained as a solid.

Halide 40: 4-Chloro-5-phenyl-2-picolyl chloride

Following the procedure described in Halide 23, Step 2, Method B, but substituting 4-chloro-5-phenyl-2-picoline (from Halide 23, Step 2, Method B, Step 2) for 5-phenyl-2-picoline as starting material the title compound was obtained as a solid.

Halide 41: 5-(t-Butyldiphenylsilyloxy)-2-picolyl chloride

Step 1: 5-(t-Butyldiphenylsilyloxy)-2-picoline

A solution of 10.9 g 5-hydroxypicoline, 8.85 g imidazole and 29.9 mL of t-butyldiphenylsilylchloride in 500 mL of $CH_2Cl_2$ was stirred for 4 days at 25° C. The mixture was washed with $H_2O$, brine, dried over $MgSO_4$ and concentrated under vacuum. The crude product was purified by silica gel chromatography (EtOAc/Hexane 10:90) to afford the pure title compound as an oil.

Step 2: 5-(t-Butyldiphenylsilyloxy)-2-picolyl chloride

Following the procedure described in Halide 23, Step 2, Method A, but substituting 5-(t-butyldiphenylsilyloxy)-2-picoline (from Step 1) for 5-phenyl-2-picoline as starting material the title compound was obtained.

Halide 42: 5-Benzyl-2-picolyl chloride

Following the procedure described in Halide 23, Steps 1 and 2, Method B, but substituting 3-benzylpyridine (Aldrich) for 3-phenylpyridine as starting material the title compound was obtained.

Halide 43: 5-(4-Chlorophenyl)-2-picolyl chloride

Step 1: 5-Trifluoromethanesulfonyloxy-2-picoline

To a solution of 5 g of 3-hydroxy-6-methylpyridine in 100 mL of $CH_2Cl_2$ at 0° C. was added successively 7.7 mL of $Et_3N$ and 8.1 mL of trifluoromethanesulfonic anhydride. The reaction was stirred at room temperature for 30 minutes, then diluted with more $CH_2Cl_2$ (200 mL). The organic phase was washed successively with 1N HCl, brine, dried over MgSO$_4$, filtered and concentrated to give after purification using flash chromatography on silica gel (hexane:EtOAc 65:35) of the title compound.

Step 2: 5-(4-Chlorophenyl)-2-picoline

The trifluoromethane sulfonate from Step 1 (500 mg) was dissolved in 10 mL of toluene, 5 mL of EtOH, and 1.6 mL of 2M aqueous Na$_2$CO$_3$. Then 203 mg LiCl, 411 mg of 4-chlorobenzeneboronic acid (Lancaster) and 832 mg of tetrakis (triphenylphosphine) palladium were added successively. The resulting reaction mixture was heated up to 90°-95° C. for 1 hour. The reaction mixture was cooled down to room temperature, EtOAc was added and the organic phase was washed with 1N NaOH, brine, dried over MgSO$_4$, filtered and concentrated. Purification by flash chromatography using hexane:EtOAc 3:2 gave the title compound.

Step 3: 5-(4-Chlorophenyl)-2-picolyl chloride

Following the procedure described in Halide 23, Step 2, Method B, but substituting 5-(4-chlorophenyl)-2-picoline (from Step 2) for 5-phenyl-2-picoline as starting material the title compound was obtained.

Halide 46 2-Chloromethyl-1,8-naphthyridine

Following the procedure described in Halide 23, Step 2, Method A, but substituting 2-methyl-1,8-naphthyridine (Chem. Pharm. Bull., 19, 1857 (1971)) for 5-phenyl-2-picoline as starting material the title compound was obtained.

Halide 47: 4-(2-Pyridyl)benzyl chloride

Following the procedure described in Halide 23, Step 2, Method A, but substituting 2-(4-tolyl)pyridine (Aldrich) for 5-phenyl-2-picoline as starting material the title compound was obtained as a solid.

Halide 54: 5-(1-Naphthyl)-2-picolyl chloride

Step 1: 5-(1-Naphthyl)-2-picoline

Following the procedure described in Halide 43, Step 2, but substituting 1-naphthaleneboronic acid (Lancaster) for 4-chlorobenzeneboronic acid as starting material the title compound was obtained.

Step 2: 5-(1-Naphthyl)-2-picolyl chloride

Following the procedure described in Halide 23, Step 2, Method B, but substituting 5-(1-naphthyl)-2-picoline (from Step 1) for 5-phenyl-2-picoline as starting material the title compound was obtained.

Halide 55: 5-(4-Methoxyphenyl)-2-picolyl chloride

Step 1: 5-(4-Methoxyphenyl)-2-picoline

Following the procedure described in Halide 43, Step 2 but substituting 4-methoxybenzene boronic acid (Lancaster) for 4-chlorobenzeneboronic acid as starting material the title compound was obtained.

Step 2: 5-(4-Methoxyphenyl)-2-picolyl chloride

Following the procedure described in Halide 23, Step 2, Method B, but substituting 5-(4-methoxyphenyl)-2-picoline (from Step 1) for 5-phenyl-2-picoline as starting material the title compound was obtained.

Halide 57: 5-Chloromethyl-2-phenylfuro[3,2-b] pyridine

Following the procedure described in Halide 23, Step 2, Method B, but substituting 5-methyl-2-phenylfuro[3,2-b]pyridine (Synthesis, 749-751 (1986)) for 5-phenyl-2-picoline as starting material the title compound was obtained.

SOURCE/PREPARATION OF THIOLS

Thiol 1: Mercaptoacetic Acid (Aldrich)
Thiol 2: 3-Mercaptopropionic Acid (Aldrich)
Thiol 3: 2-(Mercaptomethyl)butanoic Acid Step 1: Ethyl 2-(acetylthiomethyl)butanoate Ethyl 2-ethyl-2-propenoate (Arch. Pharm., 313, 846 (1980)) (5 g, 39 mmol) was diluted with 5.6 mL (78 mmol) of thiolacetic acid and stirred at 65° C. for 36 hours. The mixture was then diluted with Et$_2$O, washed with H$_2$O and the organic phase was dried with Na$_2$SO$_4$. Evaporation to dryness yielded the title material as an orange oil which was used as such for the next step.

$^1$H NMR (CDCl$_3$): δ0.96 (3H, t), 1.28 (3H, t), 1.70 (3H, m), 2.35 (3H, s), 3.10 (2H, m), 4.18 (2H, q).

Step 2: Ethyl 2-(mercaptomethyl)butanoate

To a solution of the thioester of Step 1 (5 g, 24.5 mmol) in MeOH (15 mL) at 0° C., under nitrogen, was added K$_2$CO$_3$ (9.67 g, 73.5 mmol). The resulting mixture was stirred at 0° C. for a half hour and then HOAc (8.82 g, 147 mmol) and 25% aq NH$_4$OAc were added. The title thiol was extracted with EtOAc, dried over Na$_2$SO$_4$ and purified by distillation on a Kugelrohr apparatus (200° C./760 mm Hg).

$^1$H NMR (CD$_3$COCD$_3$): δ0.86 (3H, t), 1.25 (3H, t), 1.65 (2H, quintet), 1.78 (1H, t), 2.45 (1H, quintet), 2.68 (2H, m), 4.15 (2H, q).

Step 3: 2-(Mercaptomethyl)butanoic Acid

To a solution of the eter of Step 2 (1 g, 6.2 mmol) in THF (10 mL) and MeOH (10 mL) was added 1N LiOH (10 mL). The resulting solution was stirred 3 days at room temperature, partitioned between Et$_2$O and H$_2$O and the aqueous layer decanted. The aqueous player was acidified with concentrated HCl acid and the product was extracted with Et$_2$O. The organic extracts were dried over Na$_2$SO$_4$ and concentrated in vacuo to afford the crude product which was distilled under reduced pressure (short Vigreux column) to give the title compound as a colorless liquid which had solidified upon cooling. bp 110°-115° C./approx. 2 mmHg.

Thiol 4: 2-(S)-(Mercaptomethyl)butanoic Acid

Step 1: 4-(S)-(1-Methylethyl)-2-oxazolidinone

The title compound was prepared according to Evans, Mathre and Scott (J. Org. Chem., 50, 1830 (1985)) from (S)-(+)-2-amino-3-methyl-1-butanol and diethyl carbonate in the presence of K$_2$CO$_3$.

Step 2: 3-(1-Oxobutyl-4-(S)-(1-methylethyl)-2-oxazolidinone

A mechanically stirred, cooled (−78° C.) solution of the oxazolidinone of Step 1 (32.3 g, 250 mmol) in anhydrous THF (830 mL) was metalated with 163 mL (1.6M in hexane, 261 mmol) of n-BuLi and treated with freshly distilled butanoyl chloride (28.1 mL, 271 mmol). The reaction mixture was warmed to 0° C. and stirred for 0.5 hour. Excess acid chloride was hydrolyzed by the addition of 1M aqueous K$_2$CO$_3$ (165 mL) followed by stirring the resultant two-phase mixture for 1 hour at r.t. Volatiles were removed in vacuo and the product was extracted into CH$_2$Cl$_2$ (3×). The combined organic extracts were successively washed with H$_2$O and brine, dried over MgSO$_4$ and concentrated to give a pale yellow oil. A portion of this crude product was purified by flash chromatography on silica with EtOAc:hexane 1:4 to give a colorless liquid.

$^1$H NMR (CDCl$_3$): δ0.88 (3H, d), 0.92 (3H, d), 0.99 (3H, t), 1.70 (2H, m), 2.38 (1H, m), 2.77-3.04 (2H, m), 4.18-4.31 (2H, m), 4.44 (1H, m).

Step 3: 3-[1-Oxo-2-(S)-(phenylmethylthiomethyl)-butyl]-4-(S)-(1-methylethyl)-2-oxazolidinone A solution of the N-acylated product of Step 2(36.9 g, 185 mmol) in anhydrous THF (70 mL) was added to a magnetically stirred, cooled (−78° C.) solution of LDA (prepared from 28.6 mL (20.6 g, 204 mmol) of diisopropylamine and 127.5 mL (1.6M in hexane, 204 mmol) of n-BuLi) in anhydrous THF (240 mL). After stirring for 0.5 hour at −78° C. the resultant lithium enolate was treated with benzyl bromomethyl sulfide (52.3 g, 241 mmol) for 2 hours at −20° C. The reaction was quenched by the addition of half-saturated aqueous $NH_4Cl$ (200 mL). Volatiles were removed in vacuo and the product was extracted in $CH_2Cl_2$ (3×). The combined organic extracts were successively washed with 1M aqueous $NaHSO_3$ (2×), 1M aqueous $KHCO_3$ (2×) and brine, dried over $MgSO_4$ and concentrated in vacuo to give a yellow liquid. This crude material was purified by flash chromatography on silica with EtOAc:hexane 1:99, 2:98, 5:95, 10:90 and 15:85 to give the title compound as a colorless liquid containing a small amount of the starting material, which was used as such for the next step.

Step 4: Benzyl 2-(S)-(Phenylmethylthiomethyl)-butanoate

To a magnetically stirred, cooled (−10° C.) solution of lithium benzyloxide in anhydrous THF (400 mL), prepared from freshly distilled benzyl alcohol (28.7 mL, 30.0 g, 277 mmol) and 127.5 mL (1.6M in hexane, 204 mmol) of n-BuLi, was added a solution of the product of Step 3 (48.9 g, approx. 146 mmol) in anhydrous THF (170 mL) over a 0.5 hour period. After 15 minutes at −10° C., the reaction mixture was warmed to 0° C., stirred for 2 hours and then quenched by the addition of half-saturated aqueous $NH_4Cl$ (300 mL). Volatiles were removed in vacuo and the product was extracted into $CH_2Cl_2$ (3×). The combined organic extracts were successively washed with $H_2O$ (2×) and brine, dried over $MgSO_4$ and concentrated in vacuo to give 74 g of a pale yellow oil. This crude material was purified by flash chromatography on silica with toluene giving the title compound as a colorless liquid containing a small amount of butanoic acid benzylester and an unidentified impurity. This product was used as such for the next step.

$^1H$ NMR (CDCl$_3$): δ0.87 (3H, t), 1.63 (2H, m), 2.48–2.61 (2H, m), 2.64–2.76 (1H, m), 3.68 (2H, s), 5.16 (2H, s), 7.28 (5H, br s), 7.37 (5H, br s).

Step 5: 2-(S)-(Phenylmethylthiomethyl)butanoic Acid

Glacial HOAc (120 mL) was added to a suspension of the product of Step 4 (32.4 g, approx. 103 mmol) in 210 mL of 30-32% anhydrous HBr in glacial HOAc (approx. 1.03 mol) to complete the dissolution. The resulting solution was stirred at 70° C. for 6 hours and at 50° overnight. The reaction mixture was then cooled to room temperature, diluted with $H_2O$ (750 mL) and extracted with $CH_2Cl_2$ (7×). The combined organic extracts were concentrated in vacuo. The residue was diluted with toluene (500 mL) and concentrated in vacuo 5 times to remove HOAc. The residue was dissolved in 1M aqueous KOH (750 mL), washed with $CH_2Cl_2$ (4×), acidified to pH 1 with concentrated HCl and extracted with $CH_2Cl_2$ (6×). The combined organic extracts were dried over $Na_2SO_4$ and concentrated in vacuo to afford a pale yellow liquid which was used as such for the next step. $^1H$ NMR (CDCl$_3$): δ0.91 (3H, t), 1.66 (2H, m), 2.44–2.56 (2H, m), 2.65–2.75 (1H, m), 3.73 (2H, s), 7.31 (5H, br s).

Step 6: 2-(S)-(Mercaptomethyl)butanoic Acid

A solution of the carboxylic acid of Step 5 (17.4 g, 77.6 mmol) in dry THF (30 mL) was added to approx. 200 mL of ammonia (condensed in the flask from the cylinder) at −78° C. The solution was warmed to −50° C. and Na (5.2 g, 226 mmol) was added in small portions over a 0.5 hour period. After the reaction mixture had remained dark-blue for 0.5 hour, the reaction was quenched by the addition of $NH_4Cl$ (10 g). Ammonia was evaporated under a stream of nitrogen and the THF was removed in vacuo. The residue was dissolved in 1M aqueous KOH (400 mL), and washed with $Et_2O$ (3×). The aqueous solution was cooled to 0° C. and acidified to pH 1 with concentrated HCl acid, and the product was extracted into $Et_2O$ (4×). The organic extracts were dried over $Na_2SO_4$ and concentrated in vacuo to afford the crude product which was distilled under reduced pressure (short Vigreux column) to give the title compound as a colorless liquid which solidified upon cooling; bp 102°–104° C./approx. 2 mmHg.

$[\alpha]_D = -21.7°$ (c=1.4 CHCl$_3$).

$^1H$ NMR (CDCl$_3$): α0.98 (3H, t), 1.54 (1H, t), 1.64–1.82 (2H, m), 2.50–2.87 (3H, m).

Thiol 5: 2-(R)-(Mercaptomethyl)butanoic Acid

Following the procedure described for Thiol 4, Steps 1–6 but substituting (1S,2R)-(+)-norephedrine for (S)-(+)-2-amino-3-methyl-1-butanol the title compound was obtained.

$[\alpha]_D = +20.0°$ (c=2.5 CHCl$_3$).

Thiol 6: 3-Mercapto-2-methylpropanoic Acid

Following the procedure described for Thiol 3, Steps 1–3 but substituting ethyl 2-methyl-2-propenoate for ethyl 2-ethyl-2-propenoate the title compound was obtained.

Thiol 7: 3-Mercapto-2-methoxypropanoic Acid

Step 1: Methyl 2-methoxy-2-propenoate

The dimethyl acetal of methyl pyruvate was prepared using methyl pyruvate, trimethyl orthoformate, MeOH and p-toluenesulfonic acid according to the method of Wermuth (Bull. Soc. Chim. France, 732 (1964)). Methyl pyruvate dimethylacetal (50 g) p-toluenesulfonic acid (1.34 g) and hydroquinone (1.90 g) were heated in an oil bath (approx. 150° C.) and MeOH was allowed to distill off slowly (approx. 10 mL). The residue was then distilled to afford the title ester, bp approx. 50° C./20 mmHg.

$^1H$ NMR (CDCl$_3$): δ3.67 (3H, s), 3.82 (3H, s), 4.65 (1H, d, J=2 Hz), 5.48 (1H, d, J=2 Hz).

Step 2: Methyl 3-(benzylthio)-2-methoxypropanoate

To a solution of the propenoate of Step 1 (26.93 g, 0.23 mmol) in THF (20 mL) at 0° C. was added benzyl mercaptan (23.0 mL, 0.23 mol) followed by 1M THF solution of Bu$_4$NF (20 mL). The mixture was stirred at room temperature for 1 hour. The reaction was poured into $H_2O$ and extracted with EtOAc, washed with brine, dried and concentrated to yield the title compound. Although the material is essentially pure it can be distilled under vacuum, b.p. 115°–130° C./1 mmHg.

$^1H$ NMR (CDCl$_3$): δ2.76 (2H, m), 3.43 (3H, s), 3.78 (3H, s), 3.82 (2H, s), 3.96 (1H, dd), 7.34 (5H, m).

Step 3: 3-(Benzylthio)-2-methoxypropanoic Acid

To a solution of the ester (210 mg, 0.875 mmol) of Step 2 in MeOH:$H_2O$ 5:1 (6 mL) was added $K_2CO_3$ (210 mg). After 18 hours, the reaction was quenched by the addition of 25% aq $NH_4OAc$. After acidification to pH 4 with 10% HCl, the product was extracted with EtOAc. The organic phase was dried over $Na_2SO_4$ and evaporated to provide the title compound.

$^1H$ NMR (CD$_3$COCD$_3$): δ2.73 (2H, m), 3.36 (3H, s), 3.80 (2H, s), 3.95 (1H, q), 7.16–7.36 (5H, m).

Step 4: 3-Mercapto-2-methoxypropanoic Acid

The acid of Step 3 (1.3 g, 5.7 mmol) was dissolved in liquid ammonia at −30° C. and small pieces of Na (469 mg, 20.4 mmol) were added until obtention of a persistant blue coloration. After 20 minutes, the ammonia was removed by a flow of $N_2$ and $H_2O$ (20 mL) and 10% HCl were added until obtention of pH approx. 3.5. The thiol was then extracted with EtOAc, dried over $Na_2SO_4$ and evaporated to provide the title material.

$^1$H NMR (CD$_3$COCD$_3$): δ1.88 (1H, t), 2.80 (2H, m), 3.36 (3H, s), 3.86 (1H, t).

Thiol 8: 3-Mercapto-3-methylbutanoic Acid (J. Med. Chem. 14, 868–872 (1981))

Thiol 9: 2,2-Dimethyl-3-mercaptopropanoic Acid

Using the procedure described in Chem. Abstr., 58, 11490b,c (1963), this thiol was obtained from 3-bromo-2,2-dimethylpropanoic acid (J. Am. Chem. Soc. 3016 (1955)) by substitution of the bromide by KSH.

The invention is further defined by reference to the following examples, which are intended to be illustrative and not limiting. All temperatures are in degrees Celsius.

EXAMPLE 1

3-[1-(4-Chlorobenzyl)-4-methyl-6-(5-phenylpyridin-2-ylmethoxy)4,5-dihydro-1H-thiopyrano[2,3,4-c,d]indol-2-yl]-2,2-dimethylpropanoic acid Method A:

Step 1: Methyl 3-[1-(4-chlorobenzyl)-3-t-butylthio-5-methoxyindol-2-yl]-2,2-dimethylpropanoate To a solution of 39 g methyl 5-t-butylthio-2,2-dimethyl-4-oxopentanoate in a mixture of 300 mL toluene and 150 mL glacial HOAc acid was added 15 g NaOAc and 50 g 1-(4-methoxyphenyl)-1-(4-chlorobenzyl)hydrazine hydrochloride. The reaction was stirred at room temperature for 3 days under argon in the dark. The mixture was poured onto $H_2O$ (1L) and extracted with 3×500 mL EtOAc. The EtOAc was washed with 3×500 mL $H_2O$ then once with NaHCO$_3$ solution. The organic phase was dried (MgSO$_4$), evaporated to dryness and the residue crystallised from Et$_2$O/hexane 2:1 to afford the title compound, m.p. 102°–103° C.

Step 2: 3-[1-(4-Chlorobenzyl)-3-t-butylthio-5-methoxyindol-2-yl]-2,2-dimethylpropanoic acid The ester from Step 1 (51.3 g) was hydrolysed using 325 mL THF, 600 mL MeOH and 325 mL of 1N LiOH solution. The mixture was heated to 80° C. for 3 hours, then cooled, acidified with 1N HCl and extracted with 3×200 mL EtOAc. The organic phase was washed with $H_2O$ (2×150 mL) and dried (MgSO$_4$). After removal of the solvent the title compound was obtained as a white solid, m.p. 190°–191° C.

Step 3: Methyl 3-[1-(4-chlorobenzyl)-5-hydroxy-3-t-butylthioindol-2-yl]-2,2-dimethyl propanoate A solution of 61 mL t-butylthiol in 650 mL of dry HMPA at 0° C. was treated portionwise with 26 g of 50% NaH in mineral oil after removal of the oil with hexane. The reaction was stirred at room temperature for 30 minutes and the acid from Step 2 was added and the mixture heated under $N_2$ at 175° C. for 5 hours. The reaction mixture was cooled, poured onto crushed ice, a 2N HCl solution was added until pH 5 and the mixture extracted 3×500 mL with EtOAc. After washing the organic phase with $H_2O$ (3×200 mL) it was dried (MgSO$_4$) and evaporated. The resulting residue was dissolved in 300 mL Et$_2$O and treated with ethereal diazomethane until all the acid was consumed. Excess solvent was removed and the oily residue triturated with hexane to leave a crystalline mass which was recrystallised from EtOAc/hexane to give the title compound, m.p. 170°–171° C.

Step 4: Methyl 3-[1-(4-chlorobenzyl)-3-t-butylthio-5-allyloxyindol-2-yl]-2,2-dimethyl propanoate The phenol from Step 3 (1.72 g) in 20 mL of DMF at room temperature under argon was treated sequentially with 135 mg NaH and 0.4 mL allyl bromide. After 1 hour the solution was poured onto $H_2O$ (20 mL) and extracted with 3×20 mL EtOAc. The organic layers were washed twice with water dried (MgSO$_4$) and evaporated. Chromatography of the residue on silica gel (hexane/EtOAc 10:1) gave the title compound.

This compound can also be prepared by stirring 85 g 1-(4-chlorobenzyl)-1-(4-allyloxy phenyl)hydrazine hydrochloride, 68 g methyl 5-t-butylthio-2,2-dimethyl-4-oxopentanoate, 24 g NaOAc in a mixture of 500 mL toluene and 225 mL glacial HOAc according to the procedure described in Step 1. Column chromatography of the crude product (hexane/EtOAc 9:1) gave the title compound.

Step 5: Methyl 3-[1-(4-chlorobenzyl)-4-methyl-6-hydroxy-4,5-dihydro-1H-thiopyrano[2,3,4-c,d]indol-2-yl]-2,2-dimethylpropanoate The allyl ether (1.6 g) from Step 4 was dissolved in 10 mL 1,2-dichlorobenzene and heated to reflux under $N_2$ for 16 hours. The solution was cooled to 150° C. and 1 mg p-toluene sulfonic acid added. After 45 min, the solvent was removed in vacuo and the residue purified by chromatography (silica gel; hexane/EtOAc 4:1) to give the title compound.

Step 6: Methyl 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate A solution of the phenol (7.5 g) from Step 5 in 50 mL DMF at 5° C. was treated with 651 mg NaH (50% dispersion in mineral oil) for 30 minutes and then 2.3 g 5-phenyl-2-picolyl chloride added. After 1 hour, the mixture was poured onto brine/20% citric acid solution and extracted with 3×30 mL EtOAc. The organic layers were washed with brine, dried over MgSO$_4$, filtered and concentrated. Chromatography of the residue on silica gel (hexane/EtOAc 4:1) followed by crystallisation from EtOAc/hexane gave the title compound, m.p. 135°–136° C.

Step 7: 3-[1-(4-Chlorobenzyl)-4-methyl-6-(5-phenyl-pyridin-2-yl methoxy)-4,5-dihydro-1H-thiopyrano[2,3,4-c,d]indol-2-yl]-2,2-dimethylpropanoic acid The ester (346 mg) from Step 6 was dissolved in 10 mL MeOH, 5 mL THF and 2.8 mL 1N LiOH and the solution heated to reflux for 5 hours. The organic solvents were removed in vacuo, the resulting solution poured onto 10 mL 1N HCl and this was extracted 3×10 mL EtOAc. After washing the organic layer twice with brine, the solution was dried (MgSO$_4$), concentrated and the residue recrystallised from EtOAc/hexane 1:1 to afford the title compound, m.p. 214°–215° C.

Method B:

Step 1: Methyl 3-(3-t-butylthio-5-methoxyindol-2-yl)-2,2-dimethylpropanoate

A solution of 22.7 g 1-(4-methoxyphenyl)hydrazine hydrochloride and 24.6 g methyl 5-t-butylthio-2,2-dimethyl-4-oxopentanoate in 500 mL of t-BuOH was heated at reflux under nitrogen for 24 hours. The solvent was removed under reduced pressure and the residue stirred in 900 mL ether. Filtration and evaporation of the Et$_2$O provided an oil which was chromatographed (silica gel; 3% EtOAc in toluene) to provide the title compound as an oil.

Step 2: 3-(3-t-Butylthio-5-hydroxyindol-2-yl)-2,2-dimethylpropanoic acid, lactam The ester (2.0 g) from Step 1 was added to 20 mL of pyridine hydrochloride at 175° C. under nitrogen. After 2 hours, the mixture was cooled and partitioned between EtOAc and 0.1M HCl. The EtOAc layer was washed with $H_2O$, brine, dried ($MgSO_4$) and concentrated to yield a brown foam. Purification on silica gel (hexane/EtOAc 3:1) gave the title compound.

Step 3: 3-(3-t-Butylthio-5-allyloxyindol-2-yl)-2,2-dimethylpropanoic acid, lactam Following the procedure described in Method A, Step 4 but substituting the phenol from Method B, Step 2 for methyl 3-[1-(4-chlorobenzyl)-3-t-butylthio-5-hydroxyindol-2-yl]-2,2-dimethylpropanoate the title compound was obtained as an oil.

Step 4: 3-(4-Methyl-6-hydroxy-4,5-dihydro-1H-thiopyrano[2,3,4-c,d]indol-2-yl)-2,2-dimethylpropanoic acid, lactam Following the procedure of Method A, Step 5 but substituting the allyl ether from Method B, Step 3 for methyl 3-[1-(4-chlorobenzyl)-3-t-butylthio-5-allyloxyindol-2-yl]-2,2-dimethylpropanoate with gave the title compound.

Step 5: 3-[4-Methyl-6-(5-phenylpyridin-2-ylmethoxy)-4,5-dihydro-1H-thiopyrano[2,3,4-c,d]indol-2-yl]-2,2-dimethylpropanoic acid, lactam Following the procedure used in Method A, Step 6, but substituting the phenol from Method B, Step 4 for methyl 3-[1-(4-chlorobenzyl)-4-methyl-6-(5-phenylpyridin-2-ylmethoxy)-4,5-dihydro-1H-thiopyrano [2,3,4-c,d]indol-2-yl]-2,2-dimethyl propanoate afforded the title compound, m.p. 150° C.

Step 6: 3-[4-Methyl-6-(5-phenylpyridin-2-ylmethoxy)-4,5-dihydro-1H-thiopyrano[2,3,4-c,d]indol-2-yl]-2,2-dimethylpropanoic acid A solution of the thiopyrano-indole (7.0 g) from Method B, Step 5 in 300 mL THF and 60 mL in LiOH was heated at reflux 2 hours. After cooling the mixture was diluted with 500 mL $H_2O$ and acidified with 100 mL 1M HCl solution. The precipitate was collected by filtration, washed with water and dried under vacuum to provide the title compound, m.p. 257°–259° C. (dec).

Step 7: 3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoic acid The acid (170 mg) from Method B, Step 6 in 3 mL DMF at room temperature under nitrogen was treated with 22 mg NaH and the solution stirred for 20 minutes. The mixture was cooled to 0° C., 145 mg 4-chlorobenzyl chloride added and 15 minutes later the temperature allowed to rise to room temperature. After 2 hours, the reaction was quenched with 1N HCl, extracted (×3) with EtOAc, washed with brine, dried ($MgSO_4$) and the solvent removed. The residue was chromatographed (hexane/EtOAc/HOAc 15:4:1) to give the title compound.

EXAMPLE 2

3-[1-(n-Butyl)-4-methyl-6-(5-phenylpyridin-2-ylmethoxy)-4,5-dihydro-1H-thiopyrano[2,3,4-c,d]indol-2-yl]-2,2-dimethylpropanoic acid Step 1: n-Butyl 3-[1-(n-butyl)-4-methyl-6-(5-phenylpyridin-2-ylmethoxy)-4,5-dihydro-1H-thiopyrano[2,3,4-c,d]indol-2-yl]-2,2-dimethylpropanoate The acid (300 mg) from Example 1, Method B, Step 6 in 10 mL DMF at room temperature was treated with 38 mg NaH and the solution stirred for 30 minutes. The mixture was cooled to 0° C., n-butyl bromide (171 μL) was added and 40 minutes later the temperature allowed to rise to room temperature. After 16 hour, the reaction was quenched with 1N HCl, extracted with EtOAc (2×), washed with $H_2O$, washed with brine, dried ($MgSO_4$) and the solvent removed. Column chromatography of the crude product (hexane/EtOAc 4:1) gave the title compound.

Step 2: 3-[1-(n-Butyl)-4-methyl-6-(5-phenylpyridin-2-ylmethoxy)-4,5-dihydro-1H-thiopyrano[2,3,4-c,d]indol-2-yl]-2,2-dimethylpropanoic acid The ester from Step 1 (196 mg) was dissolved in 4 mL MeOH, 10 mL THF and 2 mL 1N LiOH and the solution was heated to reflux for 5 hours. The resulting solution was poured into 10 mL 1N HCl and this was extracted with 3×10 mL EtOAc. The organic layer was washed with water, brine, dried ($MgSO_4$) and the solvent removed. Column chromatography of the crude product (hexane/EtOAc 2:1) on Bio-Sil A followed by crystallisation from $Et_2O$ gave the title compound, m.p. 203° C.

EXAMPLE 3

3-[1,4-Dimethyl-6-(5-phenylpyridin-2-ylmethoxy)-4,5-dihydro-1H-thiopyrano[2,3,4-c,d]indol-2-yl]-2,2-dimethylpropanoic acid Step 1: Methyl 3-[1,4-dimethyl-6-(5-phenylpyridin-2-ylmethoxy)-4,5-dihydro-1H-thiopyrano[2,3,4-c,d]indol-2-yl]-2,2-dimethylpropanoate The acid (200 mg) from Example 1, Method B, Step 6 in 4 mL DMF at room temperature was treated with 25 mg NaH and the solution stirred for 30 minutes. The mixture was cooled to 0° C., 66 μL methyl iodide was added and 40 minutes later the temperature allowed to rise to room temperature. After 16 hours, the reaction was quenched with 1N HCl, extracted with EtOAc (2×), washed with $H_2O$, washed with brine, dried ($MgSO_4$) and the solvent removed. The crude ester was used as such for the next step.

Step 2: 3-[1,4-Dimethyl-6-(5-phenylpyridin-2-ylmethoxy)-4,5-dihydro-1H-thiopyrano [2,3,4-c,d]indol-2-yl]-2,2-dimethylpropanoic acid The crude ester of Step 1 was dissolved in 4 mL MeOH, 10 mL THF and 2 mL 1N LiOH and the solution heated to reflux for 5 hours. The resulting solution was poured into 10 mL 1N HCl and this was extracted with 3×10 mL EtOAc. The organic layer was washed with $H_2O$, brine, dried ($MgSO_4$) and the solvent removed. Column chromatography of the crude product (hexane/EtOAc 2:1 on Bio-Sil A followed by crystallisation from $Et_2O$ gave the title compound, m.p. 204°–205° C.

EXAMPLE 4

3-[1-Benzyl-4-methyl-6-(5-phenylpyridin-2-ylmethoxy)-4,5-dihydro-1H-thiopyrano[2,3,4-c,d]indol-2-yl]-2,2-dimethylpropanoic acid Step 1: Benzyl 3-[1-benzyl-4-methyl-6-(5-phenylpyridin-2-ylmethoxy)-4,5-dihydro-1H-thiopyrano[2,3,4-c,d]indol-2-yl]2,2-dimethylpropanoate The acid (126 mg) from Example 1, Method B, Step 6 in 4 mL DMF and 4 mL THF at −78° C. under nitrogen was treated with KHMDS (0.80 mL, 0.75M in toluene). Stirring was continued for 10 minutes at −78° C. followed by 10 minutes at 0° C. after which benzyl bromide (64 μL) was added. After 6 hours, the reaction was quenched with 1N HCl, extracted with EtOAc (2×), washed with H₂O, washed with brine, dried (MgSO₄) and the solvent removed. Column chromatography of the crude product (EtOAc/hexane 1:4) gave the title compound.

Step 2: 3-[1-Benzyl-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure used in Example 2, Step 2, but substituting the ester from Step 1 for n-butyl 3-[1-(n-butyl)-4-methyl-6-(5-phenylpyridin-2-ylmethoxy)-4,5-dihydro-1H-thiopyrano[2,3,4-c,d]indol-2-yl]-2,2-dimethylpropanoate as starting material, the title compound was obtained as a solid, m.p.: 215°–216° C.

EXAMPLE 5

3-[1-(4-Methoxybenzyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 2 but substituting 4-methoxybenzyl chloride for n-butyl bromide as starting material, the title compound was obtained as a solid, m.p.: 198° C. From the alkylation step, a side-product was isolated by chromatography and led after the hydrolysis step, to the isomeric 2a-alkylated product (acid of XVI, Scheme II), m.p.: 153°–155° C.

EXAMPLE 6

3-[1-(3-Methoxybenzyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 2 but substituting 3-methoxybenzyl chloride for n-butyl bromide as starting material, the title compound was obtained as a solid, m.p.: 201° C. From the alkylation step, a side-product was isolated by chromatography and led after the hydrolysis step to the isomeric 2a-alkylated product (acid of XVI, Scheme II), m.p.: 177°–180° C.

EXAMPLE 7

3-[1-(4-Methylsulfonylbenzyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting 4-methylsulfonylbenzyl chloride for methyl iodide as starting material, the title compound was obtained as a solid, m.p.: 190°–194° C.

EXAMPLE 8

3-[1-(4-Methylthiobenzyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting 4-methylthiobenzyl chloride for methyl iodide as starting material, the title compound was obtained as a solid, m.p.: 175°–176° C.

EXAMPLE 9

3-[1-(4-Phenylbenzyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting 4-phenylbenzyl chloride for methyl iodide as starting material, the title compound was obtained as a solid, m.p.: 236°–239° C.

EXAMPLE 10

3-[1-(4-Cyanobenzyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 1, Method B, Step 7 but substituting 4-cyanobenzyl bromide for 4-chlorobenzyl chloride as starting material, the title compound being the minor product was obtained as a solid, m.p.: 180°–200° C.

The major component isolated by chromatography was the 2a-alkylated product (acid of XVI, Scheme II) (foam).

EXAMPLE 11

3-[1-(3-Phenylpropyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 2 but substituting 3-phenylpropyl bromide for n-butyl bromide as starting material, the title compound was obtained as a solid, m.p.: 180°–181° C.

EXAMPLE 12

3-[1-(3,4-Methylenedioxybenzyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting 3,4-methylenedioxybenzyl chloride for methyl iodide as starting material, the title compound was obtained as a solid, m.p.: 183°–184° C.

EXAMPLE 13

3-[1-(2-Phenoxyethyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting 2-phenoxyethyl iodide for methyl iodide as starting material, the title compound was obtained as a solid, m.p.: 165°–166° C.

EXAMPLE 14

3-[1-(Cinnamyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting cinnamyl bromide for methyl iodide as starting material, the title compound was obtained as a solid, m.p.: 190°–191° C. A side-product was isolated by chromatography which was the isomeric 2a-alkylated product (acid of XVI, Scheme II), m.p. 168°–172° C.

EXAMPLE 15

3-[1-Cyclohexylmethyl-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting cyclohexylmethyl bromide for methyl iodide as starting material, the title compound was obtained as a solid, m.p.: 229°–231° C.

EXAMPLE 16

3-[1-Allyl-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting allyl bromide for n-butyl bromide as starting material, the title compound was obtained as a solid, m.p.: 155°–156° C. From the alkylation step, a side-product was isolated by chromatography and led after the hydrolysis step to the isomeric 2a-alkylated product (acid of XVI, Scheme II), m.p.: 195°–205° C.

EXAMPLE 17

3-[1-(n-Decyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting n-decyl bromide for methyl iodide as starting material, the title compound was obtained as a solid, m.p.: 149°–150° C.

EXAMPLE 18

3-[1-(2-Phenethyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting 2-phenethyl p-toluene sulfonate for methyl iodide as starting material, the title compound was obtained (the minor product) as a solid, m.p.: 170° C.

The major product obtained was recovered starting material.

EXAMPLE 19

3-[1-(3-Cyclohexylpropyl)-4-methyl-6-(5-phenylpyridin-2-ylmethoxy)-4,5-dihydro-1H-thiopyrano[2,3,4-c,d]-indol-2-yl]-2,2-dimethylpropanoic acid Following the procedure described in Example 3 but substituting 3-cyclohexylpropyl iodide for methyl iodide as starting material, the title compound was obtained as a solid, m.p.: 147°–148° C.

EXAMPLE 20

3-[1-(Thien-2-ylmethyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting thien-2-ylmethyl methanesulfonate for methyl iodide as starting material, the title compound was obtained (the minor product) as a solid, m.p.: 218°–220° C.

The major products obtained were recovered starting material and the isomeric 2a-alkylated product (acid of XVI, Scheme II), m.p.: 175°–177° C.

EXAMPLE 21

3-[1-(Pyridin-2-ylmethyl)-4-methyl-6-(5-phenylpyridin-2-ylmethoxy)-4,5-dihydro-1H-thiopyrano-[2,3,4-c,d]indol-2-yl]-2,2-dimethylpropanoic acid Following the procedure described in Example 3 but substituting 2-picolyl chloride for methyl iodide as starting material, the title compound was obtained as a solid, m.p.: 208°–209° C.

EXAMPLE 22

3-[1-Quinolin-2-ylmethyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting 2-bromomethyl quinoline for methyl iodide as starting material, the title compound was obtained as a solid, m.p.: 212°–213° C.

EXAMPLE 23

3-[1-(5-Phenylpyridin-2-ylmethyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting 5-phenyl-2-picolyl chloride for methyl iodide as starting material, the title compound was obtained as a solid, m.p.: 159°–161° C.

EXAMPLE 24

3-[1-(2-(1-Adamantyl)ethyl)-4-methyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 3 but substituting 2-(1-adamantyl)ethyl bromide for methyl iodide as starting material, the title compound was obtained as a solid, m.p.: 160°–170° C.

EXAMPLE 25

4-[1-(3-Trifluoromethylbenzyl)-4-methyl-6-(5-phenylpyridin-2-ylmethoxy)-4,5-dihydro-1H-thiopyrano[2,3,4-c,d]indol-2-yl]-3,3-dimethylbutanoic acid Following the procedure described in Example 3, Step 1, but substituting 3-trifluoromethylbenzyl chloride for methyl iodide then following the procedure described in Example 27 but substituting the crude 3-[1-(3-trifluoromethylbenzyl)-4-methyl-6-(5-phenylpyridin-2-ylmethoxy)-4,5-dihydro-1H-thiopyrano[2,3,4-c,d]indol-2,2-dimethylpropanoate from Step 1 for methyl 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate as starting material, the title compound was obtained as a solid, m.p.: 155°–158° C.

EXAMPLE 26

5-[3-[1-(3-Trifluoromethylbenzyl)-4-methyl-6-(5-phenylpyridin-2-yl methxoy)-4,5-dihydro-1H-thiopyrano[2,3,4-c,d]indol-2-yl]-2,2-dimethylpropyl]-1H-tetrazole Following the procedure described in Example 28 but substituting 4-[1-(3-trifluoromethylbenzyl)-4-methyl-6-(5-phenylpyridin-2-ylmethoxy)-4,5-dihydro-1H-thiopyrano[2,3,4-c,d]indol-2-yl]-3,3-dimethylbutyronitrile from Example 25 for 4-[1-(4-chlorobenzyl)-4-methyl-6-(5-phenylpyridin-2-ylmethoxy)-4,5-dihydro-1H-thiopyrano[2,3,4-c,d]indol-2-yl]-3,3-dimethylbutyronitrile as starting material the title product was obtained as a solid, m.p.: 195°–199° C.

EXAMPLE 27

4-[1-(4-Chlorobenzyl)-4-methyl-6-(5-phenylpyridin-2-ylmethoxy)-4,5-dihydro-1H-thiopyrano[2,3,4-c,d]indol-2-yl]-3,3-dimethylbutanoic acid Step 1: 3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropan-1-ol The ester from Example 1, Method A, Step 6 (11.7 g) was added in portions to a suspension of LiAlH$_4$ (2.2 g) in THF (250 mL) at r.t. under nitrogen. After 30 minutes, the mixture was poured onto ice/1N HCl and extracted (3×) with Et$_2$O. The organic layers were dried (MgSO$_4$), filtered and concentrated. The residue was swished using 5% EtOAc/hexane for 1½ hours to yield the title compound, m.p. 165°–166° C.

Step 2: 3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropan-1-ol methanesulfonate Methane sulfonyl chloride (2.17 mL) was added dropwise to a solution of the alcohol from Step 1 (10.4 g) and Et$_3$N (10 mL) in 170 mL of THF at room temperature under nitrogen. The mixture was stirred for 1 hour then partitioned between 1N HCl and EtOAc. The organic layer was separated, washed with H$_2$O, dried (MgSO$_4$) and evaporated to give the title compound, m.p. 133°–134° C.

Step 3: 4-[1-(4-Chlorobenzyl)-4-methyl-6-(5-phenylpyridin-2-ylmethoxy)-4,5-dihydro-1H-thiopyrano[2,3,4-c,d]indol-2-yl]-3,3-dimethylbutyronitrile A solution of the mesylate from Step 2 (13 g) and 10 g NaCN in 25 mL DMSO and 25 mL DMF was heated to 125° C. under a nitrogen atmosphere for 8 hour. The solution was cooled, poured onto brine and extracted (3×) with EtOAc. The organic layers were washed twice with brine, dried (MgSO$_4$) and the solvent removed in vacuo. Crystallisation of the residue from ether provided the title compound, m.p. 145°–146° C.

Step 4: 4-[4-(4-Chlorobenzyl)-4-methyl-6-(5-phenylpyridin-2-ylmethoxy)-4,5-dihydro-1H-thiopyrano[2,3,4-c,d]indol-2-yl]-3,3-dimethylbutanoic acid The nitrile from Step 3 (1.2 g) was heated at reflux under nitrogen in a solution of 18 mL ethyleneglycol, 3 mL 2-methoxyethanol and 3 mL 8N KOH. After 24 hours, the reaction mixture was cooled, acidified with 3N HCl and extracted (3×) with EtOAc. The organic layers were washed twice with brine, dried (MgSO$_4$), evaporated and the residue swished with Et$_2$O to afford the title compound, m.p. 186°–190° C.

EXAMPLE 28

5-[3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropyl]-1H-tetrazole A mixture of the nitrile from Example 27, Step 3 (1.06 g), n-Bu$_3$SnN$_3$ (1.68 g) and 1,2-dichlorobenzene (5.0 mL) were heated at reflux under nitrogen for 3 hr. The solution was cooled, 1 mL HOAc added and 30 minutes later the mixture applied directly to a silica gel column (eluent: 50% EtOAc/Hexane+5% HOAc). Trituration of the product with Et$_2$O provided the title compound, m.p. 204°–205° C. (dec.).

Analysis: Calc'd for $C_{36}H_{35}ClN_6OS$: C, 68.07; H, 5.55; N, 13.23; S, 5.05; Cl, 5.58; Found: C, 67.80; H, 5.60; N, 13.01; S, 4.99; Cl, 5.60.

EXAMPLE 29

4-[1-Benzyl-4-methyl-6-(5-phenylpyridin-2-ylmethoxy)-4,5-dihydro-1H-thiopyrano[2,3,4-c,d]indol-3,3-dimethylbutanoic acid Following the procedure described in Example 27 but substituting 3-[1-benzyl-4-methyl-6-(5-phenylpyridin-2-ylmethoxy)-4,5-dihydro-1H-thiopyrano [2,3,4-c,d]indol-2-yl]-2,2-dimethylpropanoic acid from Example 4 for methyl 3-[1-(4-chlorobenzyl)-4-methyl-6-(5-phenylpyridin-2-ylmethoxy)-4,5-dihydro-1H-thiopyrano[2,3,4-c,d]indol-2,2-dimethylpropanoate as starting material the title compound was obtained as a solid, m.p.: 191°–192° C.

EXAMPLE 30

5-[3-[1-Benzyl-4-methyl-6-(5-phenylpyridin-2-ylmethoxy)-4,5-dihydro-1H-thiopyrano[2,3,4-c,d]indol-2-yl]-2,2-dimethylpropyl]-1H-tetrazole Following the procedure described in Example 28 but substituting 4-[1-benzyl-4-methyl-6-(5-phenylpyridin-2-ylmethoxy)-4,5-dihydro-1H-thiopyrano [2,3,4-c,d]indol-2-yl]-3,3-dimethylbutyronitrile from Example 29 for 4-[1-(4-chlorobenzyl)-4-methyl-6-(5-phenylpyridin-2-ylmethoxy)-4,5-dihdyro-1H-thiopyrano [2,3,4-c,d]indol-2-yl]-3,3-dimethylbutyronitrile as starting material the title product was obtained as a solid, m.p.: 206°–207° C.

EXAMPLE 31

4-[1-(3-Methoxybenzyl)-4-methyl-6-(5-phenylpyridin-2-ylmethoxy)-4,5-dihydro-1H-thiopyrano[2,3,4-c,d]indol-3,3-dimethylbutanoic acid Following the procedure described in Example 3, Step 1 but substituting 3-methoxybenzyl chloride for methyl iodide then following the procedure described in Example 27 but substituting the crude 3-methoxybenzyl 3-[1-(3-methoxybenzyl)-4-methyl-6-(5-phenylpyridin-2-ylmethoxy)-4,5-dihydro-1H-thiopyrano [2,3,4-c,d]indol-2-yl]-2,2-dimethylpropanoate for methyl 3-[1-(4-chlorobenzyl)-4-methyl-6-(5-phenylpyridin-2-ylmethoxy)-4,5-dihydro-1H-thiopyrano [2,3,4-c,d]indol-2,2-dimethylpropanoate as starting material the title compound was obtained as a solid, m.p.: 161°–163° C.

EXAMPLE 32

5-[1-(3-Methoxybenzyl)-4-methyl-6-(5-phenylpyridin-2-ylmethoxy)-4,5-dihydro-1H-thiopyrano[2,3,4-c,d]indol-2-yl]-2,2-dimethylpropyl]-1H-tetrazole Following the procedure described in Example 28 but substituting 4-[1-(3-methoxybenzyl)-4-methyl-6-(5-phenylpyridin-2-ylmethoxy)-4,5-dihydro-1H-thiopyrano[2,3,4-c,d]indol-2-yl]-3,3-dimethylbutyronitrile from Example 31 for 4-[1-(4-chlorobenzyl)-4-methyl-6-(5-phenylpyridin-2-ylmethoxy)-4,5-dihydro-1H-thiopyrano[2,3,4-c,d]indol-2-yl]-3,3-dimethylbutyronitrile as starting material the title product was obtained as a solid, m.p.: 181°–183° C.

EXAMPLE 33

4-[1-(4-Fluorobenzyl)-4-methyl-6-(5-phenylpyridin-2-ylmethoxy)-4,5-dihydro-1H-thiopyrano[2,3,4-c,d]indol-3,3-dimethylbutanoic acid Following the procedure described in Example 3, Step 1 but substituting 4-fluorobenzyl chloride for methyl iodide then following the procedure described in Example 27 but substituting the crude 4-fluorobenzyl 3-[1-(4-fluorobenzyl)-4-methyl-6-(5-phenylpyridin-2-ylmethoxy)-4,5-dihydro-1H-thiopyrano [2,3,4-c,d]indol-2-yl]-2,2-dimethylpropanoate for methyl 3-[1-(4-chlorobenzyl)-4-methyl-6-(5-phenylpyridin-2-ylmethoxy)-4,5-dihydro-1H-thiopyrano [2,3,4-c,d]indol-2,2-dimethylpropanoate as starting material the title compound was obtained as a solid, m.p.: 176°–178° C.

EXAMPLE 34

5-[3-[1-(4-Fluorobenzyl)-4-methyl-6-(5-phenylpyridin-2-ylmethoxy)-4,5-dihydro-1H-thiopyrano[2,3,4-c,d]indol-2-yl]-2,2-dimethylpropyl]-1H-tetrazole Following the procedure described in Example 28 but substituting 4-[1-(4-fluorobenzyl)-4-methyl-6-(5-phenylpyridin-2-ylmethoxy)-4,5-dihydro-1H-thiopyrano[2,3,4-c,d]indol-2-yl]-3,3-dimethylbutyronitrile from Example 33 for 4-[1-(4-chlorobenzyl)-4-methyl-6-(5-phenylpyridin-2-ylmethoxy)-4,5-dihydro-1H-thiopyrano[2,3,4-c,d]indol-2-yl]-3,3-dimethylbutyronitrile as starting material the title product was obtained as a solid, m.p.: 208°–210° C.

EXAMPLE 35

4-[1-(3-Chlorobenzyl)-4-methyl-6-(5-phenylpyridin-2-ylmethoxy)-4,5-dihydro-1H-thiopyrano[2,3,4-c,d]indol-3,3-dimethylbutanoic acid Following the procedure described in Example 3, Step 1, but substituting 3-chlorobenzyl chloride for methyl iodide then following the procedure described in Example 27 but substituting the crude 3-chlorobenzyl 3-[1-(3-chlorobenzyl)-4-methyl-6-(5-phenylpyridin-2-ylmethoxy)-4,5-dihydro-1H-thiopyrano [2,3,4-c,d]indol-2-yl]-2,2-dimethylpropanoate for methyl 3-[1-(4-chlorobenzyl)-4-methyl-6-(5-phenylpyridin-2-ylmethoxy)-4,5-dihydro-1H-thiopyrano [2,3,4-c,d]indol-2,2-dimethylpropanoate as starting material the title compound was obtained as a solid, m.p.: 185°–186° C.

EXAMPLE 36

5-[3-[1-(3-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropyl]-1H-tetrazole Following the procedure described in Example 28 but substituting 4-[1-(3-chlorobenzyl)-4-methyl-6-(5-phenylpyridin-2-ylmethoxy)-4,5-dihydro-1H-thiopyrano[2,3,4-c,d]indol-2-yl]-3,3-dimethylbutyronitrile from Example 35 for 4-[1-(4-chlorobenzyl)-4-methyl-6-(5-phenylpyridin-2-ylmethoxy)-4,5-dihydro-1H-thiopyrano[2,3,4-c,d]indol-2-yl]-3,3-dimethylbutyronitrile as starting material the title product was obtained as a solid, m.p.: 230°–231° C.

EXAMPLE 37

4-[1-(3-Fluorobenzyl)-4-methyl-6-(5-phenylpyridin-2-ylmethoxy)-4,5-dihydro-1H-thiopyrano[2,3,4-c,d]indol-3,3-dimethylbutanoic acid Following the procedure described in Example 3, Step 1, but substituting 3-fluorobenzyl chloride for methyl iodide then following the procedure described in Example 27 but substituting the crude 3-fluorobenzyl 3-[1-(3-fluorobenzyl)-4-methyl-6-(5-phenylpyridin-2-ylmethoxy)-4,5-dihydro-1H-thiopyrano [2,3,4-c,d]indol-2-yl]-2,2-dimethylpropanoate for methyl 3-[1-(4-chlorobenzyl)-4-methyl-6-(5-phenylpyridin-2-ylmethoxy)-4,5-dihydro-1H-thiopyrano [2,3,4-c,d]indol-2,2-dimethylpropanoate as starting material the title compound was obtained as a solid, m.p.: 180°–182° C.

EXAMPLE 38

5-[3-[1-(3-Fluorobenzyl)-4-methyl-6-(5-phenylpyridin-2-ylmethoxy)-4,5-dihydro-1H-thiopyrano[2,3,4-c,d]indol-2-yl]-2,2-dimethylpropyl]-1H-tetrazole Following the procedure described in Example 28 but substituting 4-[1-(4-fluorobenzyl)-4-methyl-6-(5-phenylpyridin-2-ylmethoxy)-4,5-dihydro-1H-thiopyrano-[2,3,4-c,d]indol-2-yl]-3,3-dimethylbutyronitrile from Example 37 for 4-[1-(4-chlorobenzyl)-4-methyl-6-(5-phenylpyridin-2-ylmethoxy)-4,5-dihydro-1H-thiopyrano[2,3,4-c,d]indol-2-yl]-3,3-dimethylbutyronitrile as starting material the title product was obtained as a solid, m.p.: 214°–215° C.

EXAMPLE 39

4-[1-(Pyridin-2-ylmethyl)-4-methyl-6-(5-phenylpyridin-2-ylmethoxy)-4,5-dihydro-1H-thiopyrano[2,3,4-c,d]indol-3,3-dimethylbutanoic acid Following the procedure described in Example 3, Step 1, but substituting 2-picolyl chloride for methyl iodide then following the procedure described in Example 27 but substituting the crude pyridin-2-ylmethyl-3-[1-(pyridin-2-ylmethyl)-4-methyl-6-(5-phenylpyridin-2-ylmethoxy)-4,5-dihydro-1H-thiopyrano [2,3,4-c,d]indol-2-yl]-2,2-dimethylpropanoate for methyl 3-[1-(4-chlorobenzyl)-4-methyl-6-(5-phenylpyridin-2-ylmethoxy)-4,5-dihydro-1H-thiopyrano [2,3,4-c,d]indol-2,2-dimethylpropanoate as starting material the title compound was obtained as a solid, m.p.: 174°–175° C.

EXAMPLE 40

5-[3-[1-(Pyridin-2-ylmethyl)-4-methyl-6-(5-phenylpyridin-2-ylmethoxy)-4,5-dihydro-1H-thiopyrano[2,3,4-c,d]indol-2-yl]-2,2-dimethylpropyl]-1H-tetrazole Following the procedure described in Example 28 but substituting 4-[1-(pyridin-2-ylmethyl)-4-methyl-6-(5-phenylpyridin-2-ylmethoxy)-4,5-dihydro-1H-thiopyrano[2,3,4-c,d]indol-2-yl]-3,3-dimethylbutyronitrile from Example 39 for 4-[1-(4-chlorobenzyl)-4-methyl-6-(5-phenylpyridin-2-ylmethoxy)-4,5-dihydro-1H-thiopyrano[ 2,3,4-c,d]indol-2-yl]-3,3-dimethylbutyronitrile as starting material the title product was obtained as a solid, m.p.: 243°–245° C.

EXAMPLE 41

4-[1-(3-Phenylpropyl)-4-methyl-6-(5-phenylpyridin-2-ylmethoxy)-4,5-dihydro-1H-thiopyrano[2,3,4-c,d]indol-3,3-dimethylbutanoic acid Following the procedure described in Example 27 but substituting 3-[1-(3-phenylpropyl)-4-methyl-6-(5-phenylpyridin-2-ylmethoxy)-4,5-dihydro-1H-thiopyrano[2,3,4-c,d]indol-2-yl]-2,2-dimethylpropanoic acid from Example 11 for methyl 3-[1-(4-chlorobenzyl)-4-methyl-6-(5-phenylpyridin-2-ylmethoxy)-4,5-dihydro-1H-thiopyrano[2,3,4-c,d]indol-2,2-dimethylpropanoate as starting material the title compound was obtained as a solid, m.p.: 134°–135° C.

EXAMPLE 42

5-[3-[1-(3-Phenylpropyl)-4-methyl-6-(5-phenylpyridin-2-ylmethoxy)-4,5-dihydro-1H-thiopyrano[2,3,4-c,d]indol-2-yl]-2,2-dimethylpropyl]-1H-tetrazole Following the procedure described in Example 28 but substituting 4-[1-(3-phenylpropyl)-4-methyl-6-(5-phenylpyridin-2-ylmethoxy)-4,5-dihydro-1H-thiopyrano[2,3,4-c,d]indol-2-yl]-3,3-dimethylbutyronitrile from Example 41 for 4-[1-(4-chlorobenzyl)-4-methyl-6-(5-phenylpyridin-2-ylmethoxy)-4,5-dihydro-1H-thiopyrano[2,3,4-c,d]indol-2-yl]-3,3-dimethylbutyronitrile as starting material the title product was obtained as a solid, m.p.: 139°–140° C.

EXAMPLE 43

4-[1-Cyclohexylmethyl-4-methyl-6-(5-phenylpyridin-2-ylmethoxy)-4,5-dihydro-1H-thiopyrano[2,3,4-c,d]indol-2-yl]-3,3-dimethylbutanoic acid Following the procedure described in Example 27 but substituting the acid from Example 15 for methyl 3-[1-(4-chlorobenzyl)-4-methyl-6-(5-phenylpyridin-2-ylmethoxy)-4,5-dihydro-1H-thiopyrano [2,3,4-c,d]indol-2-yl]-2,2-dimethylpropanoate the title compound was obtained as a solid, m.p.: 175°–176° C.

EXAMPLE 44

5-[3-[1-Cyclohexylmethyl-4-methyl-6-(5-phenylpyridin-2-ylmethoxy)-4,5-dihydro-1H-thiopyrano[2,3,4-c,d]indol-2-yl]-2,2-dimethylpropyl]-1H-tetrazole Following the procedure described in Example 28, but substituting 4-[1-cyclohexylmethyl-4-methyl-6-(5-phenylpyridin-2-ylmethoxy)-4,5-dihydro-1H-thiopyrano[2,3,4-c,d]indol-2-yl]-3,3-dimethylbutyronitrile from Example 43 for 4-[1-(4-chlorobenzyl)-4-methyl-6-(5-phenylpyridin-2-ylmethoxy)-4,5-dihydro-1H-thiopyrano[2,3,4-c,d]indol-2-yl]-3,3-dimethylbutyronitrile as starting material the title compound was obtained as a solid, m.p.: 137°–142° C.

Analysis: Calc'd for $C_{36}H_{42}N_6OS \cdot \frac{1}{2}H_2O$: C, 70.21; H, 7.03; N, 13.64; Found: C, 70.09; H, 6.97; N, 13.06.

EXAMPLE 45

4-[1-(4-Chlorobenzyl)-4-methyl-6-(5-phenylpyridin-2-ylmethoxy)-4,5-dihydro-1H-thiopyrano[2,3,4-c,d]indol-2-yl]-3,3-dimethyl-N-methylsulfonyl butyramide A mixture of the acid (200 mg) from Example 27, Step 4, methanesulfonamide (40 mg), 4-dimethylaminopyridine (40 mg), and 1-cyclohexyl-3-(2-morpholinoethyl)carbodiimide metho-p-toluenesulfonate (172 mg) in $CH_2Cl_2$ (5 mL) was stirred at r.t. for 18 hours. The mixture was acidified with 3N HCl. The organic layer was separated, dried ($MgSO_4$), filtered and concentrated in vacuo. The residue was chromatographed on silica gel using 3% MeOH in $CHCl_3$ to obtain the title compound, m.p.: 101°–105° C.

EXAMPLE 46

4-[1-(4-Chlorobenzyl)-4-methyl-6-(5-phenylpyridin-2-ylmethoxy)-4,5-dihydro-1H-thiopyrano[2,3,4-c,d]indol-2-yl]-3,3-dimethyl-N-phenylsulfonyl butyramide Following the procedure described in Example 45 but replacing methanesulfonamide with phenylsulfonamide, the acid from Example 27, Step 4 was converted to the title compound, m.p.: 115°–120° C.

EXAMPLE 47

4-[1-(4-Chlorobenzyl)-4-methyl-6-(5-phenylpyridin-2-ylmethoxy)-4,5-dihydro-1H-thiopyrano[2,3,4-c,d]indol-2-yl]-3,3-dimethyl-N-trifluoromethylsulfonyl butyramide Following the procedure described in Example 45 but replacing methanesulfonamide with trifluoromethyl sulfonamide, the acid from Example 27, Step 4 was converted to the title compound, m.p.: 168°–173° C.

EXAMPLE 48

5-[1-(4-Chlorobenzyl)-4-methyl-6-(5-phenylpyridin-2-ylmethoxy)-4,5-dihydro-1H-thiopyrano[2,3,4-c,d]indol-2-yl]-4,4-dimethylpentanoic acid Following the procedure described in Example 27, Steps 1–4, but substituting 4-[1-(4-chlorobenzyl)-4-methyl-6-(5-phenylpyridin-2-ylmethoxy)-4,5-dihydro-1H-thiopyrano[2,3,4-c,d]indol-2-yl]-3,3-dimethylbutanoic acid (from Example 27, Step 4) for methyl 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate as starting material, the title compound was obtained as a solid, m.p.: 151°–153° C.

EXAMPLE 49

5-[4-[1-(4-Chlorobenzyl)-4-methyl-6-(5-phenylpyridin-2-ylmethoxy)-4,5-dihydro-1H-thiopyrano[2,3,4-c,d]indol-2-yl]-3,3-dimethylbutyl]-1H-tetrazole Following the procedure described in Example 28, but substituting 5-[1-(4-chlorobenzyl)-4-methyl-6-(5-phenylpyridin-2-ylmethoxy)-4,5-dihydro-1H-thiopyrano[2,3,4-c,d]indol-2-yl]-4,4-dimethylvaleronitrile (from Example 48) for 4-[1-(4-chlorobenzyl)-4-methyl-6-(5-phenylpyridin-2-ylmethoxy)-4,5-dihydro-1H-thiopyrano[2,3,4-c,d]indol-2-yl]-3,3-dimethylbutyronitrile as starting material, the title compound was obtained as a solid, m.p.: 177° C. (dec).

EXAMPLE 50

[1-(4-Chlorobenzyl)-4-methyl-6-(5-phenylpyridin-2-ylmethoxy)-4,5-dihydro-1H-thiopyrano[2,3,4-c,d]indol-2-yl]carboxylic acid Step 1: Ethyl [1-(4-chlorobenzyl)-3-t-butylthio-5-allyloxyindol-2-yl]carboxylate A solution of 18.6 g ethyl 3-t-butylthio-2-oxopropanoate, 26.3 g 1-(4-chlorobenzyl)-1-(4-allyloxyphenyl)hydrazine hydrochloride and 15 g NaOAc in 300 mL toluene and 150 mL HOAc was stirred at room temperature under nitrogen for 16 hours then at 70° C. for 2 hour. The mixture was cooled, poured onto $H_2O$, extracted (3×) EtOAc and the organic layers then washed successively with sat. $NaHCO_3$ and brine. After drying over $MgSO_4$ the solution was filtered, evaporated and the residue chromatographed (silica gel; hexane/EtOAc 4:1) to afford the title compound.

Step 2: [1-(4-Chlorobenzyl)-4-methyl-6-(5-phenylpyridin-2-ylmethoxy)-4,5-dihydro-1H-thiopyrano[2,3,4-c,d]indol-2-yl]carboxylic acid Following the procedure described in Example 1, Method A, Steps 5 to 7 but substituting the ester from Step 1 for methyl 3-[1-(4-chlorobenzyl)-3-t-butylthio-5-allyloxyindol-2-yl]-2,2-dimethylpropanoate the title product was obtained as a solid, m.p.: 255°–256.5° C.

EXAMPLE 51

[1-(4-Chlorobenzyl)-4-methyl-6-(5-phenylpyridin-2-ylmethoxy)-4,5-dihydro-1H-thiopyrano[2,3,4-c,d]indol-2-yl]acetic acid Following the procedure described in Example 50 but substituting ethyl 4-t-butylthio-3-oxobutanoate for ethyl 3-t-butylthio-2-oxopropanoate as starting material in Step 1 the title compound was obtained as a solid, m.p.: 148°–150° C.

EXAMPLE 52

3-[1-(4-Chlorobenzyl)-4-methyl-6-(5-phenylpyridin-2-ylmethoxy)-4,5-dihydro-1H-thiopyrano[2,3,4-c,d]indol-2-yl]propanoic acid Following the procedure described in Example 27, Steps 1–4 but substituting ethyl [1-(4-chlorobenzyl)-4-methyl-6-(5-phenylpyridin-2-ylmethoxy)-4,5-dihydro-1H-thiopyrano[2,3,4-c,d]indol-2-yl]acetate from Example 51 for methyl 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate as starting material, the title compound was obtained as a solid, m.p.: 188°–190° C. (dec).

EXAMPLE 53

5-[2-[1-(4-Chlorobenzyl)-4-methyl-6-(5-phenylpyridin-2-ylmethoxy)-4,5-dihydro-1H-thiopyrano[2,3,4-c,d]indol-2-yl]-1H-tetrazole Following the procedure described in Example 28 but substituting 3-[1-(4-chlorobenzyl)-4-methyl-6-(5-phenylpyridin-2-ylmethoxy)-4,5-dihydro-1H-thiopyrano[2,3,4-c,d]indol-2-yl]propionitrile from Example 52 for 4-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylbutyronitrile as starting material, the title compound was obtained as a solid, m.p.: 244°–247° C. (dec).

EXAMPLE 54

4-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylbutanoic acid Following the procedure described in Example 50 but substituting methyl 6-t-butylthio-2,2-dimethyl-5-oxohexanoate for ethyl 3-t-butylthio-2-oxopropanoate as starting material in Step 1 the title compound was obtained as a solid, m.p.: 220°–221° C.

Analysis: Calc'd for $C_{36}H_{35}ClN_2O_3S$: C, 70.75; H, 5.77; N, 4.58; Found: C, 70.75; H, 5.78; N, 4.61.

EXAMPLE 55

3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethyl-N-hydroxy-N-methylpropionamide To a suspension of 119.7 mg of the acid from Example 1, Step 7 in 4 mL of $CH_2Cl_2$ at room temperature was added 37 μL of oxalyl chloride and one drop of DMF. After 15 minutes the resulting solution was added slowly to a cooled (0° C.) mixture of N-methyl hydroxylamine. HCl (668 mg) and $Et_3N$ (1.6 mL) in 1 mL of $H_2O$ and 1 mL of THF. After 15 minutes the reaction was diluted with $H_2O$, extracted with EtOAc and acidified to pH approx. 1 with 1N HCl. The organic phase was then washed with $NH_4OAc$ (25%) and dried over $MgSO_4$ to give, after filtration and evaporation, the title compound, m.p.: 175° C.

EXAMPLE 56

3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropionamide To a solution of the acid (500 mg) from Example 1, Step 7 in THF (15 mL) at −5° C. and under nitrogen atmosphere was added i-butyl chloroformate (125 mg) followed by $Et_3N$ (420 mg). The mixture was stirred for 30 minutes in the cold after which ammonia gas was bubbled into the mixture for 5 minutes. The mixture was acidified with 1N HCl then the organic layer was separated, dried ($MgSO_4$), filtered and concentrated in vacuo. The residue was chromatographed on silica gel using 80:15:5 hexane:EtOAc:HOAc as eluent to obtain the title compound, m.p.: 223°–225° C.

EXAMPLE 57

3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethyl-N-dimethylpropionamide Following the procedure of Example 56 but substituting methylamine gas for ammonia gas, the acid (500 mg) from Example 1, Step 7 was converted to the title compound, m.p.: 163°–165° C.

EXAMPLE 58

3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethyl-N,N-dimethylpropionamide To a solution of the acid (500 mg) from Example 1, Step 7 in THF (7 mL) and toluene (5 mL) at 5° C. and under a nitrogen atmosphere was added DMF (180 mg) followed by oxalyl chloride (115 mg) dropwise. After stirring for 30 minutes a solution of 3N dimethylamine in toluene (2.5 mL) was added dropwise. The mixture was stirred for another 30 minutes and then poured into excess 1N HCl. EtOAc and brine were added. The organic layer was separated, dried (MgSO₄), filtered and concentrated in vacuo. The residue was chromatographed on silica gel using 65:30:5 hexane:EtOAc:HOAc as eluent to obtain the title compound, m.p.: 168°–170° C.

EXAMPLE 59

3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethyl-N-carboxymethylpropionamide Step 1: 3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethyl-N-methoxycarbonylmethyl propionamide To a solution of the acid (400 mg) from Example 1, Step 7 in THF (10 mL) at −5° C. and under nitrogen atmosphere was added DMF (180 mg) followed by oxalyl chloride (115 mg) dropwise. After stirring for 30 minutes, a premixed mixture of glycine methyl ester hydrochloride (518 mg), Et₃N (0.1 mL) in THF (5 mL) was added in 5 portions. The reaction mixture was permitted to gradually rise to room temperature and dilute brine was then added. The organic layer was separated, dried (MgSO₄), filtered and concentrated in vacuo. The residue was chromatographed on silica gel using 10% MeOH in CHCl₃ as eluent to obtain the title compound as an oil.

Step 2: 3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethyl-N-carboxymethylpropionamide The ester (187 mg) from Step 1 was hydrolysed by refluxing for 30 minutes with 2N LiOH (1.0 mL) in THF (5 mL) and MeOH (5 mL). After cooling, the mixture was added to 3N HCl containing brine. The mixture was extracted with EtOAc and the organic layer separated, dried (MgSO₄), filtered and concentrated in vacuo. The residue was slurried with a solvent mixture of 1:1:1 CH₂Cl₂:HOAc:Et₂O, filtered and washed with Et₂O to give the title compound, m.p.: 196°–200° C.

EXAMPLE 60

3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethyl-N-(3-acetamidopropyl)propionamide To a mixture of the amine (146 mg) from Example 61 and Et₃N (0.5 mL) in THF (5 mL) was added dropwise and at room temperature acetyl chloride (35 mg). After stirring for 30 minutes the mixture was diluted with brine and more tetrahydrofuran. The organic layer was separated, dried (MgSO₄), filtered and concentrated in vacuo. The residue was chromatographed on silica gel using 1:10:75 NH₄OH:MeOH:CHCl₃ to obtain the title compound as a foam type solid, mass spectrum m/e: 695 (M+).

EXAMPLE 61

3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethyl-N-(3-aminopropyl) propionamide A mixture of the acid (438 mg) from Example 1, Step 7 and 1,1-carbonyldiimidazole (162 mg) in THF (15 mL) was stirred at room temperature for 18 hours. To this mixture was then added in one portion a solution of 1,3-diaminopropane (1.0 g) in THF (5 mL). The resultant mixture was stirred for 1 hour and diluted with brine. The organic layer was separated, dried (MgSO₄), filtered and concentrated in vacuo. The residue was chromatographed on silica gel using 1:10:75 NH₄OH:MeOH:CHCl₃ to obtain the title compound as an oil, mass spectrum m/e: 695 (M+).

EXAMPLE 62

3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethyl-N-butylpropionamide To a solution of the acid (500 mg) from Example 1, Step 7 in THF (10 mL) at −5° C. and under nitrogen atmosphere was added DMF (180 μL) followed by oxalyl chloride (123 mg). After stirring for 130 minutes n-butylamine (365 mg) was added dropwise. The mixture was stirred for another 30 minutes and then excess 1N HCl acid was added. EtOAc and brine was added, the organic layer separated, dried (MgSO₄), filtered and concentrated in vacuo. The residue was chromatographed on silica gel using 3% MeOH in CH₂Cl₂ to obtain the title compound as an oil which crystallized from Et₂O, m.p.: 158°–160° C.

Analysis: Calc'd for C₃₉H₄₂ClN₃O₂S: c, 71.81; H, 6.49; N, 6.44; Found: C, 72.35; H, 6.21; N, 6.53.

EXAMPLE 63

1-[1-(4-Chlorobenzyl)-4-methyl-6-(5-phenylpyridin-2-ylmethoxy)-4,5-dihydro-1H-thiopyrano[2,3,4-c,d]indol-2-yl]-2-methyl-2-propanamine Step 1: 3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropionylazide To a solution of the acid (1.2 g) from Example 1, Step 7 in THF (50 mL) at −5° C. and under nitrogen atmosphere was added i-butyl chloroformate (344 mg) followed by Et₃N (1.1 g). After stirring for 30 minutes in the cold, a solution of n-Bu₄NBr (70 mg) and NaN₃ (215 mg) in H₂O (6 mL) was added in one portion. The mixture was stirred for one hour as the temperature gradually rose to 10° C. Brine and EtOAc were added. The organic layer was separated, dried (MgSO₄), filtered and concentrated in vacuo to obtain the title compound, m.p.: 135° C.

Step 2: 1-[1-(4-Chlorobenzyl)-4-methyl-6-(5-phenylpyridin-2-ylmethoxy)-4,5-dihydro-1H-thiopyrano[2,3,4-c,d]indol-2-yl]-2-methyl-2-propylisocyanate A solution of the azide (1.5 g) from Step 1 in CHCl₃ (25 mL) was refluxed under a nitrogen atmosphere for 1.5 hours. The solution was concentrated in vacuo to obtain the title compound.

Step 3: 1-[1-(4-Chlorobenzyl)-4-methyl-6-(5-phenylpyridin-2-ylmethoxy)-4,5-dihydro-1H-thiopyrano[2,3,4-c,d]indol-2-yl]-2-methyl-2-propanamine A solution of the isocyanate (1.5 g) from Step 2 in HOAc (25 mL) and 6N HCl (5 mL) was heated for 15 minutes in an oil bath at 100° C. The mixture was evaporated to remove most of the HOAc. The residue was partitioned between excess 3N NaOH and THF. The organic layer was separated, dried (MgSO₄), filtered and concentrated in vacuo. The residue was chromatographed on silica gel using 2% Et₃N in EtOAc as eluent to obtain the title compound, m.p.: 145°–148° C.

EXAMPLE 64

N-[1-[1-(4-chlorobenzyl)-4-methyl-6-(5-phenylpyridin-2-ylmethoxy)-4,5-dihydro-1H-thiopyrano[2,3,4-c,d]indol-2-yl]-2-methyl-2-propyl]acetamide Acetyl chloride (42 mg) was added dropwise to a mixture of the amine (150 mg) from Example 63, Step 3 and Et₃N (0.5 mL) in THF (5 mL). After stirring for 30 minutes the mixture was diluted with brine and Et₂O. The organic layer was separated, dried (MgSO₄), filtered and concentrated in vacuo. The residue was chromatographed on silica gel using 50% EtOAc in hexane to give the title compound, m.p.: 170°–171° C.

Analysis: Calc'd for $C_{36}H_{36}ClN_3O_2S$: C, 70.79; H, 5.94; N, 6.88; S, 5.25; Cl, 5.80; Found: C, 70.93; H, 6.28; N, 6.59; S, 4.91; Cl, 5.47.

EXAMPLE 65

Ethyl 2-[1-[1-(4-Chlorobenzyl)-4-methyl-6-(5-phenylpyridin-2-ylmethoxy)-4,5-dihydro-1H-thiopyrano[2,3,4-c,d]indol-2-yl]-2-methyl-2-propylamino]-2-oxoacetate Following the procedure of Example 64, but substituting ethyloxalyl chloride for acetyl chloride, the amine (350 mg) from Example 63, Step 3 was converted to the title compound, m.p.: 168°–169° C.

EXAMPLE 66

2-[1-[1-(4-Chlorobenzyl)-4-methyl-6-(5-phenylpyridin-2-ylmethoxy)-4,5-dihydro-1H-thiopyrano[2,3,4-c,d]indol-2-yl]-2-methyl-2-propylamino]-2-oxoacetic acid Following the procedure of Example 59, Step 2 but substituting the ester from Example 65 (300 mg) for 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethyl-N-methoxycarbonylmethyl propionamide, the title compound was obtained as a solid, m.p.: 165° C. (dec).

EXAMPLE 67

N-[1-[1-(4-chlorobenzyl)-4-methyl-6-(5-phenylpyridin-2-ylmethoxy)-4,5-dihydro-1H-thiopyrano[2,3,4-c,d]indol-2-yl]-2-methyl-2-propyl]benzenesulfonamide A solution of the amine from Example 63, Step 3 (139 mg) Et₃N (1 mL) in 5 mL of THF at r.t. under nitrogen was treated with benzenesulfonylchloride (120 μL) for 24 hours. The mixture was poured onto brine, extracted with Et₂N (2×) and the organic layers washed with 1N NaOH solution. After drying over MgSO₄, the solution was filtered, concentrated and the product chromatographed (using 30% EtOAc/hexane as eluent) to give the title compound as a solid, m.p.: 140°–148° C.

EXAMPLE 68

[1-(4-Chlorobenzyl)-4-methyl-6-(5-phenylpyridin-2-ylmethoxy)-4,5-dihydro-1H-thiopyrano[2,3,4-c,d]indol-2ylmethoxy]acetic acid Step 1: [1-(4-Chlorobenzyl)-4-methyl-6-(5-phenyl-pyridin-2-ylmethoxy)-4,5-dihydro-1H-thiopyrano[2,3,4-c,d]indol-2-yl]methanol Ethyl [1-(4-chlorobenzyl)-4-methyl-6-(5-phenylpyridin-2-ylmethoxy)-4,5-dihydro-1H-thiopyrano [2,3,4-c,d]indol-2-yl] carboxylate (13 g) from Example 50, Step 2 was dissolved in 400 mL THF at 0° C. under nitrogen and 1.3 g LiAlH₄ was added in portions. After 30 minutes the reaction was warmed to room temperature and stirred for a further 1 hour. The solution was poured onto ice, acidified with 1N HCl, and the precipitate collected by filtration. The precipitate was dissolved in THF/EtOAc and washed twice with brine, dried (MgSO₄) and evaporated to give the title compound as a solid.

Step 2: Ethyl [1-(4-chlorobenzyl)-4-methyl-6-(5-phenylpyridin-2-ylmethoxy)-4,5-dihydro-1H-thiopyrano[2,3,4-c,d]indol-2-ylmethoxy]acetate The alcohol from Step 1 (500 mg) in 15 mL DMSO was treated with NaH (10 mg) then ethyl bromoacetate (0.1 mL) and the reaction stirred for 30 minutes. This sequence was repeated until 110 mg NaH and 1.1 mL ethyl bromoacetate had been added. After 6 hours, the solution was poured onto 1N HCl and extracted (3×) EtOAc. The organic layers were combined, washed with brine, dried (MgSO₄) and the solvent removed. Purification of the residue by chromatography (hexane/EtOAc 3:1) yielded the title compound.

Step 3: [1-(4-Chlorobenzyl)-4-methyl-6-(5-phenyl-pyridin-2-ylmethoxy)-4,5-dihydro-1H-thiopyrano[2,3,4-c,d]indol-2-ylmethoxy]acetic acid The ester from Step 2 (200 mg), 1N LiOH (1.6 mL), THF (3 mL) and MeOH (4 mL) were stirred at room temperature overnight. The solution was acidified with 1N HCl, then filtered, washed with ether and dried in vacuo to give the title compound as a solid, m.p. 158°–159° C.

EXAMPLE 69

2-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]propanoic acid Following the procedure described in Example 68, Steps 1 to 3 but substituting ethyl 2-bromopropionate for ethyl bromoacetate in Step 2, the title compound was obtained as a solid, m.p. 191°–192° C.

Analysis: Calc'd for $C_{34}H_{31}ClN_2O_4S$: C, 68.16; H, 5.22; N, 4.68; Found: C, 67.86; H, 5.22; N, 4.74.

EXAMPLE 70

[1-(4-Chlorobenzyl)-4-methyl-6-(5-phenylpyridin-2-ylmethoxy)-4,5-dihydro-1H-thiopyrano[2,3,4-c,d]indol-2-ylmethylthio]acetic acid Step 1: Methyl [1-(4-chlorobenzyl)-4-methyl-6-(5-phenylpyridin-2-ylmethoxy)-4,5-dihydro-1H-thiopyrano[2,3,4-c,d]indol-2-ylmethylthio]acetate

[1-(4-Chlorobenzyl)-4-methyl-6-(5-phenylpyridin-2-ylmethoxy)-4,5-dihydro-1H-thiopyrano [2,3,4-c,d]indol-2-yl]methanol from Example 68, Step 1 (514 mg) was suspended in 20 mL 1,2-dichloroethane at room temperature under nitrogen. To the suspension was added 91 μl methyl thioglycolate followed by 0.18 mL boron trifluoride etherate and the reaction mixture stirred for 3 minutes. The solution was poured onto 1N HCl, extracted (2×) with EtOAc and the organic layers washed with brine. Removal of the dried solvent followed by chromatography (hexane/EtOAc 3:1) provided the title compound.

Step 2: [1-(4-Chlorobenzyl)-4-methyl-6-(5-phenyl-pyridin-2-ylmethoxy)-4,5-dihydro-1H-thiopyrano[2,3,4-c,d]indol-2-ylmethylthio]acetic acid The ester from Step 1 (467 mg), 1N LiOH (3.8 mL), THF (10 mL) and MeOH (15 mL) were stirred at room temperature for 1 hr and the solution then poured onto 1N HCl. After extraction with EtOAc/THF 1:1 (3×) the organic layers were washed with brine, dried (MgSO$_4$) and evaporated. Trituration of the residue with acetone/Et$_2$O 1:1 provided the title compound, m.p. 170°–172° C.

Analysis: Calc'd for C$_{33}$H$_{29}$ClN$_2$O$_3$S$_2$: C, 65.93; H, 4.86; N, 4.66; S, 10.67; Found: C, 65.48; H, 4.90; N, 4.66; S, 10.54.

EXAMPLE 71

3-[1-(4-Chlorobenzyl)-4-methyl-6-(5-phenylpyridin-2-ylmethoxy)-4,5-dihydro-1H-thiopyrano[2,3,4-c,d]indol-2-ylmethylthio]propanoic acid Following the procedure described in Example 70, Step 1 but substituting methyl thioglycolate with 3-mercaptopropanoic acid the title compound was obtained as a solid, m.p.: 182°–183° C.

Analysis: Calc'd for C$_{34}$H$_{31}$ClN$_2$O$_3$S$_2$: C, 66.38; H, 5.08; N, 4.55; Found: C, 66.36; H, 5.22; N, 4.60.

EXAMPLE 72

3-[1-(4-Chlorobenzyl)-4-methyl-6-(5-phenylpyridin-2-ylmethoxy)-4,5-dihydro-1H-thiopyrano[2,3,4-c,d]indol-2-ylmethylthio]-2-ethylpropanoic acid Following the procedure described in Example 70, Step 1 but substituting methyl thioglycolate with 3-mercapto-2-ethylpropanoic acid the title compound was obtained as a solid, m.p.: 135°–137° C.

Analysis: Calc'd for C$_{36}$H$_{35}$ClN$_2$O$_3$S$_2$: C, 67.22; H, 5.48; N, 4.35; Found: C, 67.08; H, 5.56; N, 4.28.

EXAMPLE 73

3-[1-(4-Chlorobenzyl)-4-methyl-6-(5-phenylpyridin-2-ylmethoxy)-4,5-dihydro-1H-thiopyrano[2,3,4-c,d]indol-2-ylmethylthio]-2(S)-ethylpropanoic acid Following the procedure described in Example 70, Step 1 but substituting methyl thioglycolate with 3-mercapto-2(S)-ethylpropanoic acid the title compound was obtained as a solid, m.p.: 161°–162° C.

Analysis Calc'd for C$_{36}$H$_{35}$ClN$_2$O$_3$S$_2$: C, 67.22; H, 5.48; N, 4.35; S, 9.97; Found: C, 67.51; H, 5.62; N, 4.31; S, 9.77.

EXAMPLE 74

3-[1-(4-Chlorobenzyl)-4-methyl-6-(5-phenylpyridin-2-ylmethoxy)-4,5-dihydro-1H-thiopyrano[2,3,4-c,d]indol-2-ylmethylthio]-2(R)-ethylpropanoic acid Following the procedure described in Example 70, Step 1 but substituting methyl thioglycolate with 3-mercapto-2(R)-ethylpropanoic acid the title compound was obtained as a solid, m.p.: 163°–165° C.

Analysis: Calc'd for C$_{36}$H$_{35}$ClN$_2$O$_3$S$_2$: C, 67.22; H, 5.48; N, 4.35; S, 9.97; Found: C, 67.02; H, 5.62; N, 4.19; S, 9.58.

EXAMPLE 75

3-[1-(4-Chlorobenzyl)-4-methyl-6-(5-phenylpyridin-2-ylmethoxy)-4,5-dihydro-1H-thiopyrano[2,3,4-c,d]indol-2-ylmethylthio]-2-methylpropanoic acid Following the procedure described in Example 70, Step 1 but substituting methyl thioglycolate with 3-mercapto-2-methylpropanoic acid the title compound was obtained as a solid, m.p.: 151°–154° C.

Analysis: Calc'd for C$_{35}$H$_{33}$ClN$_2$O$_3$S$_2$: C, 66.81; H, 5.29; N, 4.45; S, 10.19; Found: C, 67.10; H, 5.17; N, 4.46; S, 10.22.

EXAMPLE 76

3-[1-(4-Chlorobenzyl)-4-methyl-6-(5-phenylpyridin-2-ylmethoxy)-4,5-dihydro-1H-thiopyrano[2,3,4-c,d]indol-2-ylmethylthio]-2-methoxypropanoic acid Following the procedure described in Example 70, Step 1 but substituting methyl thioglycolate with 3-mercapto-2-methoxypropanoic acid the title compound was obtained as a solid, m.p.: 139°–140° C.

Analysis: Calc'd for C$_{35}$H$_{33}$ClN$_2$O$_4$S$_2$: C, 65.15; H, 5.16; N, 4.34; S, 9.94; Found: C, 64.99; H, 5.33; N, 4.22; S, 9.80.

EXAMPLE 77

3-[1-(4-Chlorobenzyl)-4-methyl-6-(5-phenylpyridin-2-ylmethoxy)-4,5-dihydro-1H-thiopyrano[2,3,4-c,d]indol-2-ylmethylthio]-3-methylbutanoic acid Following the procedure described in Example 70, Step 1 but substituting methyl thioglycolate with 3-mercapto-3-methylbutanoic acid the title compound was obtained as a solid, m.p.: 178°–179° C.

Analysis: Calc'd for C$_{36}$H$_{35}$ClN$_2$O$_3$S$_2$: C, 67.22; H, 5.48; N, 4.35; S, 9.97; Found: C, 66.71; H, 5.43; N, 4.46; S, 10.02.

EXAMPLE 78

3-[1-(4-Chlorobenzyl)-4methyl-6-(5-phenylpyridin-2-ylmethoxy)-4,5-dihydro-1H-thiopyrano[2,3,4-c,d]indol-2-ylmethylthio]-2,2-dimethylpropanoic acid Following the procedure described in Example 70, Step 1 but substituting methyl thioglycolate with 3-mercapto-2,2-dimethylpropanoic acid the title compound was obtained as a solid, m.p.: 120°–123° C.

EXAMPLE 79

5-[2-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]ethyl]-1H-tetrazole Step 1: 3-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]propionitrile

[1-(4-Chlorobenzyl)-4-methyl-6-(5-phenylpyridin-2-ylmethoxy)-4,5-dihydro-1H-thiopyrano [2,3,4-c,d]indol-2-yl] methanol from Example 68, Step 1 (148 mg), acrylonitrile (0.1 mL), Triton B (50 μL) in THF (4 mL) were stirred at room temperature under nitrogen for 30 minutes. The solution was diluted with THF and 1N HCl and extracted twice with EtOAc/THF 1:1. The organic layers were washed with brine, dried (MgSO$_4$), concentrated and the residue passed through a silica gel plug to afford (after removal of the solvent) the title compound as a solid.

Step 2: 5-[2-[1-(4-Chlorobenzyl)-4-methyl-6-(5-phenylpyridin-2-ylmethoxy)-4,5-dihydro-1H-thiopyrano[2,3,4-c,d]indol-2-ylmethoxy]ethyl]-1H-tetrazole The nitrile from Step 1 (112 mg) and 0.32 mL nBu$_3$SnN$_3$ in 5 mL 1,2-dichlorobenzene were heated to 130° C. for 3 hr under a nitrogen atmosphere. The solution was cooled and chromatographed (hexane/EtOAc 1:1 then EtOAc/HOAc 95:5) to provide the title compound as a solid, m.p. 183°–184° C.

Analysis: Calc'd for C$_{34}$H$_{31}$ClN$_6$O$_2$S: C, 65.53; H, 5.01; N, 13.49; Found: C, 65.26; H, 5.08; N, 13.31.

EXAMPLE 80

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]acetic acid Step 1: t-Butyl 2-[-2-[1-(4-chlorobenzyl)-4-methyl-6-(5-phenylpyridin-2-ylmethoxy)-4,5-dihydro-1H-thiopyrano[2,3,4-c,d]indol-2-yl]ethoxy]acetate A solution of 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol (1 g), from Example 52, in DMF (20 mL) was cooled to 0° C. and NaH (216 mg) added. After stirring for 20 minutes, n—Bu$_4$NI (666 mg) was added, immediately followed by t-butyl bromoacetate (1.7 mL). The mixture was stirred for 18 hrs at 0° C., then poured into a saturated solution of NH$_4$Cl (50 mL) and extracted with Et$_2$O (2×50 mL). The organic layer was washed with brine (2×30 mL), dried and evaporated to give the title compound as an oil.

Step 2: 2-[-2-[1-(4-Chlorobenzyl-4-methyl-6-(5-phenylpyridin-2-ylmethoxy)-4,5-dihydro-1H-thiopyrano[2,3,4-c,d]indol-2-yl]ethoxy]acetic acid Following the procedure described in Example 1, Method A, Step 7 but substituting t-butyl 2-[2-[1-(4-chlorobenzyl)-4-methyl-6-(5-phenylpyridin-2-ylmethoxy)-4,5-dihydro-1H-thiopyrano[2,3,4-c,d]indol-2-yl]ethoxy]acetate, from Step 1, for methyl 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate as starting material, the title compound was obtained as a solid, m.p.: 104° C. (dec).

EXAMPLE 81

5-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxymethyl]-1H-tetrazole Step 1: 2-[-2-[1-(4-chlorobenzyl)-4-methyl-6-(5-phenylpyridin-2-ylmethoxy)-4,5-dihydro-1H-thiopyrano[2,3,4-c,d]indol-2-yl]ethoxy]acetamide To a solution of 2-[-2-[1-(4-chlorobenzyl)-4-methyl-6-(5-phenylpyridin-2-ylmethoxy)-4,5-dihydro-1H-thiopyrano[2,3,4-c,d]indol-2-yl]ethoxy]acetic acid (200 mg), from Example 80, Step 2, in 5 mL of Et$_2$O was added an ethereal solution of diazomethane until the esterification was complete. The excess solvent was evaporated and the oily residue dissolved in m-xylene (5 mL). To this solution was added 0.66 mL of dimethylaluminium amide and the mixture heated at 85/C. for 2.5 hours. After cooling to 25° C. the mixture was poured over a mixture of ice and 10 mL 1N HCl, extracted with 50 mL EtOAc washed with 2×30 mL brine and dried (MgSO$_4$). Evaporation of the solvent and chromatography on silica gel (EtOAc) afforded the title compound as an oil.

Step 2: 2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]acetonitrile The amide from Step 1 (90 mg) was dissolved in 1 mL THF and to this solution was added 0.1 mL pyridine and 0.1 mL trifluoroacetic anhydride. After 20 min. 5 mL of a saturated solution of NH$_4$Cl chloride was added and the mixture was extracted with 2×15 mL EtOAc. The organic layer was washed with 2×10 mL brine, dried (MgSO$_4$) and the solvent evaporated giving the title compound as an oil.

Step 3: 5-([2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxymethyl)-1H-tetrazole Following the procedure in Example 28 but substituting the nitrile from Step 2 for 4-[1-(4-chlorobenzyl)-4-methyl-6-(5-phenylpyridin-2-ylmethoxy)-4,5-dihydro-1H-thiopyrano[2,3,4-c,d]indol-2-yl]-3,3-dimethyl-butyronitrile as starting material, the title compound was obtained as a solid, m.p.: 143° C. (dec).

EXAMPLE 82

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]propanoic acid Step 1: Ethyl 2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]propanoate To a solution of 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol (150 mg) from Example 52, in 2.8 mL DMF was added 33 mg NaH and after 10 min, 0.22 mL ethyl 2-bromopropionate. The mixture was then stirred for 30 minutes. Brine (5 mL) was added and the mixture was extracted with 2×20 mL Et$_2$O. The organic layer was washed with 2×20 mL brine, dried (MgSO$_4$) and concentrated. The residue was chromatographed on silica gel (EtOAc:Hexane 30:70) affording the title compound as an oil.

Step 2: 2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]propanoic acid A solution of the ester (91 mg) from Step 1 in 1 mL THF, 0.6 mL MeOH and 0.7 mL 1N LiOH was heated at 50° C. for 1 hr. After cooling the mixture to 25° C., 3 mL 1N HCl was added. The mixture was extracted with 2×15 mL EtOAc, dried (MgSO$_4$) and concentrated. Chromatography on silica gel (EtOAc:Hexane 1:1, followed by addition of 5% AcOH) gave the title compound as a solid, m.p.: 156°–158° C.

EXAMPLE 83

5-(1-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]ethyl)-1H-tetrazole Step 1: 2-[-2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]propionamide To the ester from Example 82, Step 1 (500 mg) in m-xylene (12.5 mL) was added 1.56 mL of 1M dimethylaluminium amide. The solution was heated at 75° C. for 2 hours, then cooled to 25° C. and poured over ice and 10 mL 1N HCl. The mixture was extracted with EtOAc (2×30 mL), the organic layer washed with brine (2×20 mL), dried and evaporated giving the title compound as an oil.

Step 2: 2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]propionitrile The amide from Step 1 was dissolved in 20 mL THF and to this solution was added pyridine (1 mL) and trifluoroacetic anhydride (1 mL). After 20 minutes a solution of saturated NH$_4$Cl was added. The mixture was extracted with EtOAc (2×30 mL), washed with brine (2×20 mL), dried (MgSO$_4$) and concentrated. Trituration with ether:hexane, afforded the title compound.

Step 3: 5-(1-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]ethyl)-1H-tetrazole The nitrile (400 mg) from Step 2 was dissolved in 1,2-dichlorobenzene (5 mL) and n-Bu$_3$SnN$_3$ (1.12 g) was added. The mixture was heated at 125° C. for 1 hour then cooled to room temperature. HOAc (1 mL) was added, the mixture stirred for 20 minutes then chromatographed on silica gel (EtOAc:hexane 1:1, followed by addition of HOAc) to afford the title compound as a solid, m.p.: 220° C. (dec).

EXAMPLE 84

2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethylthio]propanoic acid Step 1: [2-[1-(4-Chlorobenzyl)-4-methyl-6-(5-phenylpyridin-2-ylmethoxy)-4,5-dihydro-1H-thiopyrano[2,3,4-c,d]indol-2-yl]ethyl]-4-toluenesulfonate To a solution of 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol (1 g) from Example 52 in pyridine (20 mL) was added 4-(N,N-dimethylamino)pyridine (1 crystal) and 4-toluenesulfonylchloride (485 mg). After 18 hours the mixture was poured onto H$_2$O (40 mL) and extracted with EtOAc (2×50 mL). The organic layer was washed with H$_2$O (2×30 mL), 20% citric acid (3×30 mL), dried (MgSO$_4$) and concentrated. Chromatography on silica gel (EtOAc:hexane, 40:60) afforded the title compound.

Step 2: 2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethylthio]propanoic acid To a solution of thiolactic acid (48 μL) in DMF (5 mL) at 0° C. was added NaH (26 mg) and after 15 min the sulfonate ester (250 mg) from Step 1. After 18 hours the mixture was heated at 50° C. for 1 hour. The solution was cooled, 1N HCl (4 mL) added and the mixture was extracted with EtOAc (2×30 mL). The organic layer was washed with brine (2×20 mL), dried (MgSO$_4$) and concentrated. Chromatography of the residue on silica gel (EtOAc:hexane, 1:1 followed by addition of 5% HOAc) afforded the title compound as a solid, m.p.: 159°-160° C.

EXAMPLE 85

3-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]propanoic acid Step 1: Methyl 3-[2-[1-(4-chlorobenzyl)-4-methyl-6-(5-phenylpyridin-2-ylmethoxy)-4,5-dihydro-1H-thiopyrano[2,3,4-c,d]indol-2-yl]ethoxy]propanoate To a solution of 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol (300 mg) from Example 52 in THF (8 mL) was added Triton B (2 drops) followed by methyl acrylate (0.2 mL). After 24 hours, 10 mL of saturated NH$_4$Cl was added and the mixture was extracted with EtOAc (2×30 mL). The organic layer was washed with brine (2×20 mL), dried (MgSO$_4$) and concentrated. Chromatography on silica gel (EtOAc:hexane 30:70) afforded the title compound.

Step 2: 3-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]propanoic acid Following the same procedure as in Example 82, Step 2 but substituting methyl 3-[2-[1-(4-chlorobenzyl)-4-methyl-6-(5-phenylpyridin-2-ylmethoxy)-4,5-dihydro-1H-thiopyrano[2,3,4-c,d]indol-2-yl]ethoxy]propanoate from Step 1 for ethyl 2-[2-[1-(4-chlorobenzyl)-4-methyl-6-(5-phenylpyridin-2-ylmethoxy)-4,5-dihydro-1H-thiopyrano[2,3,4-c,d]indol-2-yl]ethoxy]propanoate as starting material, the title compound was obtained as a solid, m.p.: 151°-152° C.

EXAMPLE 86

5-(2-[2-[1-(4-Chlorobenzyl)-4-methyl-6-(5-phenylpyridin-2-ylmethoxy)-4,5-dihydro-1H-thiopyrano[2,3,4-c,d]indol-2-yl]ethoxy]ethyl)-1H-tetrazole Following the same procedure as in Example 79, Steps 1 and 2 but substituting 2-[1-(4-chlorobenzyl)-4-methyl-6-(5-phenylpyridin-2-ylmethoxy)-4,5-dihydro-1H-thiopyrano[2,3,4-c,d]indol-2-yl]ethanol from Example 52 for [1-(4-chlorobenzyl)-4-methyl-6-(5-phenylpyridin-2-ylmethoxy)-4,5-dihydro-1H-thiopyrano[2,3,4-c,d]indol-2-yl]methanol as starting material afforded the title compound as a solid, m.p.: 150°-152° C.

EXAMPLE 87

2-[1-Benzyl-4-methyl-6-(5-phenylpyridin-2-ylmethoxy)-4,5-dihydro-1H-thiopyrano[2,3,4-c,d]indol-2-ylethoxy]propanoic acid Step 1: Ethyl [1-benzyl-4-methyl-6-(5-phenylpyridin-2-ylmethoxy)-4,5-dihydro-1H-thiopyrano[2,3,4-c,d]indol-2-yl]acetate Following the procedure described in Example 50 but using ethyl 4-t-butylthio-3-oxobutanoate and 1-benzyl-1-(4-allyloxyphenyl)hydrazine as starting materials the title compound was obtained.

Step 2: 2-[1-Benzyl-4-methyl-6-(5-phenylpyridin-2-ylmethoxy)-4,5-dihydro-1H-thiopyrano-[2,3,4-c,d]indol-2-ylethoxy]propanoic acid Following the procedures outlined in Example 27, Step 1 and Example 82 but substituting the ester from Step 1 for methyl 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate as starting material the title compound was obtained as a solid, m.p.: 165°-168° C.

Analysis: Calc'd for C$_{35}$H$_{34}$N$_2$O$_4$S.½H$_2$O: C, 71.52; H, 6.00; N, 4.76; Found: C, 71.27; H, 5.71; N, 4.77.

EXAMPLE 88

3-[1-(4-Chlorobenzyl)-4,4-dimethyl-6-(5-phenylpyridin-2-ylmethoxy)-4,5-dihydro-1H-thiopyrano[2,3,4-c,d]indol-2-yl]-2,2-dimethylpropanoic acid Following the procedure described in Example 1, Method A but substituting 3-chloro-2-methylpropene for allyl bromide in Step 4, the title compound was obtained as a solid, m.p. 216°-217° C.

EXAMPLE 89

(+)-3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoic acid The title compound was obtained by following the procedure described in Example 1, Method B, Steps 5 to 7 but substituting the racemic material in Step 5 for (+)-3-(4-methyl-6-hydroxy-4,5-dihydro-1H-thiopyrano[2,3,4-c,d]indol-2-yl)-2,2-dimethylpropanoic acid, lactam. Resolution of the racemate (from Example 1, Method B, Step 4) was achieved by preparative HPLC using a Chiracel OD column (50×2 cm I.D.) eluting with hexane/i-PrOH 9:1 at 8 mL/minute. The enantiomer with the shorter retention time was collected to provide (after removal of the solvent) (+)-3-(4-methyl-6-hydroxy-4,5-dihydro-1H-thiopyrano[2,3,4-c,d]indol-2-yl)-2,2-dimethylpropanoic acid, lactam. The title compound had m.p. 196°–197° C. and $[\alpha]_D + 52.7°$ (c=1.5, acetone).

Analysis: Calc'd for $C_{35}H_{33}ClN_2O_3S$: C, 70.40; H, 5.57; N, 4.69; Found: C, 70.30; H, 5.64; N, 4.69.

EXAMPLE 90

(−)-3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoic acid The title compound was obtained by following the procedure described in Example 1, Method B, Steps 5 to 7 but substituting the racemic material in Step 5 for (−)-3-(4-methyl-6-hydroxy-4,5-dihydro-1H-thiopyrano[2,3,4-c,d]indol-2-yl)-2,2-dimethylpropanoic acid, lactam. Resolution of the racemate (from Example 1, Method B, Step 4) was achieved by preparative HPLC using a Chiracel OD column (50×2 cm I.D.) eluting with hexane/i-PrOH 9:1 at 8 mL/minute. The enantiomer with the longer retention time was collected to provide (after removal of the solvent) (−)-3-(4-methyl-6-hydroxy-4,5-dihydro-1H-thiopyrano[2,3,4-c,d]indol-2-yl)-2,2-dimethylpropanoic acid, lactam. The title compound had m.p. 194°–195° C. and $[\alpha]_D - 55.7°$ (c=2.8, acetone).

Analysis: Calc'd for $C_{35}H_{33}ClN_2O_3S$: C, 70.40; H, 5.57; N, 4.69; Found: C, 69.97; H, 5.64; N, 4.59.

EXAMPLE 91

3-[1-(4-Chlorobenzyl)-6-(5-phenylpyridin-2-ylmethoxy)-4,5-dihydro-1H-thiopyrano[2,3,4-c,d]indol-2-yl]-2,2-dimethylpropanoic acid Step 1: 3-[1-(4-Chlorobenzyl)-5-hydroxyindol-2-yl]-2,2-dimethylpropanoic acid A mixture of the ester from Example 1, Method A, Step 1 (1.0 g), ethane thiol (1.3 mL) and $AlCl_3$ (3.47 g) in $CH_2Cl_2$ (50 mL) was stirred at room temperature under a nitrogen atmosphere for 40 minutes. The solution was poured onto 1N HCl, extracted with EtOAc (3×) and the combined organic layers washed twice with brine. Removal of the dried ($MgSO_4$) solvent provided the title compound.

Step 2: Methyl 3-[1-(4-chlorobenzyl)-5-hydroxyindol-2-yl]-2,2-dimethylpropanoate The acid from Step 1 (0.84 g) was dissolved in 10 mL of $Et_2O$ and a solution of diazomethane in $Et_2O$ was added portionwise until all the acid had been consumed. Excess diazomethane was removed by addition of 1 mL HOAc, the solvent was then removed and the residue chromatographed (hexane/EtOAc 4:1) to give the title compound.

Step 3: Methyl 3-[3-carbomethoxymethylthio-1-(4-chlorobenzyl)-5-hydroxyindol-2-yl]-2,2-dimethylpropanoate To a solution of dimethyldithiodiacetate (Arch. Pharm., 1961 294, 475) (1.4 g, 6.66 mmol) in 1,2-dichloroethane (18 mL) there was added sulfuryl chloride (850 mg, 6.3 mmol) and the resulting solution was stirred at room temperature for 10 minutes. It was then slowly added to a solution of the ester from Step 2 (3.71 g, 10 mmol) in DMF (25 mL) precooled to 0° C. The mixture was then stirred at 0° C. for one hour and quenched with $H_2O$ (200 mL) then extracted twice with $Et_2O$. These extracts were washed with $H_2O$ 3 times, dried and evaporated to a residue which was chromatographed on silica gel, eluting with a 2:1 mixture of hexane-EtOAc to afford the title compound (3.29 g) as a yellow oil.

Step 4: Methyl 3-[3-carboxymethylthio-1-(4-chlorobenzyl)-5-hydroxyindol-2-yl]-2,2-dimethylpropanoate To a solution of diester from Step 3 (4.5 g, 9.46 mmol) in MeOH (90 mL) there was added 1N LiOH (50 mL) and the mixture was stirred for 1 hour at r.t. It was then diluted with $H_2O$ and extracted twice with $Et_2O$. The aqueous fraction was then acidified with 6N HCl and extracted 4 times with $Et_2O$. These extracts were washed 4 times with $H_2O$, dried and evaporated to yield the title compound as a thick oil.

Step 5: Methyl 3-[1-(4-chlorobenzyl)-5-hydroxy-3-(2-hydroxyethylthio)indol-2-yl]-2,2-dimethylpropanoate To a solution of the acid from Step 4 (3.8 g, 8.23 mmol) in THF (200 mL) there was added 0.9M borane in THF (25 mL) and the mixture was stirred at r.t. for 1.5 hours. Water (25 mL) was added and the THF removed by evaporation. More $H_2O$ was added along with 2N HCl (15 mL) and the mixture was extracted with $Et_2O$ 3 times. These extracts were washed with $H_2O$ 4 times, dried and evaporated to leave a residue which was chromatographed on silica gel, eluting with a 1:1 mixture of hexane and EtOAc. The title compound was obtained as a thick oil.

Step 6: Methyl 3-[1-(4-chlorobenzyl)-3-(formylmethylthio)-5-hydroxyindol-2-yl]-2,2-dimethylpropanoate To a solution of oxalyl chloride (579 mg, 4.56 mmol) in $CH_2Cl_2$ (15 mL) at −70° C. there was slowly added DMSO (711 mg, 9.12 mmol). The mixture was stirred for 3 minutes, then at −70° C. there was slowly added a solution of the alcohol from Step 5 (1.7 g, 3.8 mmol) in $CH_2Cl_2$ (15 mL). The resulting mixture was stirred at −70° C. for 20 minutes, then there was slowly added $Et_3N$ (1.92 g, 19 mmol). The mixture was stirred in the cold for a further 5 minutes, then it was allowed to warm up to room temperature. After dilution with $Et_2O$ (200 mL) the mixture was washed twice with 1N HCl, then with $H_2O$ (3×), dried and evaporated to a residue which was chromatographed on silica gel, eluting with a 1:1 mixture of hexane and EtOAc, to afford the title compound as a thick oil.

Step 7: Methyl 3-[1-(4-chlorobenzyl)-6-hydroxy-4,5-dihydro-1H-thiopyrano[2,3,4-c,d]indol-2-yl]-2,2-dimethylpropanoate A mixture of aldehyde from Step 6 (830 mg, 1.86 mmol), phenylboric acid (367 mg, 3.01 mmol), propionic acid (42 mg, 0.57 mmol) and benzene (15 mL) was refluxed with azeotropic removal of $H_2O$ for 5.5 hours. The cooled mixture was diluted with $Et_2O$ (200 mL), washed twice with 25% aqueous $NH_4OAc$, twice with $H_2O$, dried and evaporated. The residue was chromatographed on silica gel, eluting with a 2:1 mixture of hexane and EtOAc, and the compound corresponding to the least polar streaking material on TLC was collected. This afforded the intermediate 1,3,2-dioxaborin as a solid.

To a solution of the crude dioxaborin (300 mg, 0.57 mmol) in 1,2-dichloroethane (8 mL) there was added triethyl silane (331 mg, 2.85 mmol) and boron trifluoride etherate (243 mg, 1.71 mmol); the mixture was then heated at 60° C. for 6 hours, cooled and quenched with $H_2O$ (25 mL). The organic phase was collected, and the aqueous phase extracted twice with CH$_2$Cl$_2$. The combined organic fractions were washed 3 times with H$_2$O, dried and evaporated down. The residue was chromatographed on silica gel, eluting with a 2:1 mixture of hexane and EtOAc, to afford the title compound as a thick oil.

Step 8: 3-[1-(4-Chlorobenzyl)-6-(5-phenylpyridin-2-ylmethoxy)-4,5-dihydro-1H-thiopyrano[2,3,4-c,d]indol-2-yl]-2,2-dimethylpropanoic acid Following the procedure described in Example 1, Method A, Steps 6 and 7, but substituting the product from Step 7 for methyl 3-[1-(4-chlorobenzyl)-4-methyl-6-hydroxy-4,5-dihydro-1H-thiopyrano [2,3,4-c,d]indol-2-yl]-2,2-dimethylpropanoate as starting material, the title compound was obtained as a white solid, m.p.: 203°–205° C.

EXAMPLE 92

3-[1-(4-Chlorobenzyl)-4-ethyl-6-(5-phenylpyridin-2-ylmethoxy)-4,5-dihydro-1H-thiopyrano[2,3,4-c,d]indol-2-yl]-2,2-dimethylpropanoic acid Step 1: Methyl 3-[3-t-butylthio-1-(4-chlorobenzyl)-4-crotyl-5-hydroxyindol-2-yl]-2,2-dimethylpropanoate To a suspension of KH (35% dispersion in oil, 547 mg, 4.78 mmol) in p-xylene (20 mL) there was added methyl 3-[3-tert-butylthio-1-(4-chlorobenzyl)-5-hydroxyindol-2-yl]-2,2-dimethylpropanoate from Example 1, Method A, Step 3 (2.0 g, 4.35 mmol) and the mixture was refluxed for 20 minutes; after cooling, there was added freshly fused ZnCl$_2$ (68 mg, 0.5 mmol) and the mixture was again refluxed for one hour, then cooled down to r.t. To the solution was added crotyl bromide (882 mg, 6.53 mmol) and stirring was continued at room temperature overnight. The mixture was quenched with saturated aqueous NH$_4$Cl (20 mL) and 2 mL of 1N HCl. The organic phase was collected and the aqueous phase extracted with EtOAc. The combined organic phases were washed with H$_2$O 3 times, dried and evaporated. The residue was chromatographed to afford the title compound as the minor component, as a yellow oil.

Step 2: Methyl 3-[1-(4-chlorobenzyl)-4-ethyl-6-hydroxy-4,5-dihydro-1H-thiopyrano[2,3,4-c,d]-indol-2-yl]-2,2-dimethylpropanoate To a solution of the product from Step 1 (100 mg) in 1,2-dichlorobenzene (6 mL) there was added a few crystals of p-toluenesulfonic acid, and the mixture was refluxed for 2 hours. The solvent was evaporated and the residue chromatographed on silica gel eluting with a 3:1 mixture of EtOAc and hexane to afford the title compound as a yellow oil.

Step 3: 3-[1-(4-Chlorobenzyl)-4-ethyl-6-(5-phenyl-pyridin-2-ylmethoxy)-4,5-dihydro-1H-thiopyrano[2,3,4-c,d]indol-2-yl]-2,2-dimethylpropanoic acid Following the procedures described in Example 1, Method A, Steps 6 and 7, but substituting the product from Step 2 for methyl 3-[1-(4-chlorobenzyl)-4-methyl-6-hydroxy-4,5-dihydro-1H-thiopyrano [2,3,4-c,d]indol-2-yl]-2,2-dimethylpropanoate as starting material, the title compound was obtained as a cream-colored solid, m.p.: 167°–169° C.

EXAMPLE 93

3-[1-(4-Chlorobenzyl)-6-(5-phenylpyridin-2-ylmethoxy)-4-propyl-4,5-dihydro-1H-thiopyrano[2,3,4-c,d]indol-2-yl]-2,2-dimethylpropanoic acid Following the procedure described in Example 92, Steps 1–3, but substituting 1-bromo-trans-2-pentene for crotyl bromide as starting material, the title compound was obtained as a cream-colored solid, m.p.: 212°–213° C.

EXAMPLE 94

3-[1-(4-Chlorobenzyl)-4-methyl-6-(5-phenyl-1-oxopyridin-2-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 2-chloromethyl-5-phenylpyridine-N-oxide for 5-phenyl-2-picolyl chloride as starting material, the title compound was obtained as a solid, m.p.: 215° C.

EXAMPLE 95

5-[3-[1-(4-Chlorobenzyl)-4-methyl-6-(5-phenyl-1-oxopyridin-2-ylmethoxy)-4,5-dihydro-1H-thiopyrano[2,3,4-c,d]indol-2-yl]-2,2-dimethylpropyl]-1H-tetrazole Following the procedure described in Example 1, Method A, Step 6 and Example 28, but substituting 2-chloromethyl-5-phenylpyridine-N-oxide for 5-phenyl-2-picolyl chloride as starting material, the title compound was obtained as a solid, m.p.: 128° C.

EXAMPLE 96

3-[1-(4-Chlorobenzyl)-4-methyl-6-(quinolin-2-ylmethoxy)-4,5-dihydro-1H-thiopyrano[2,3,4-c,d]indol-2-yl]-2,2-dimethylpropanoic acid Following the procedure described in Example 1, Method A, steps 6–7, but substituting 2-chloromethyl-quinoline for 5-phenyl-2-picolyl chloride as starting material, the title compound was obtained as a solid, m.p.: 190°–191° C.

EXAMPLE 97

3-[1-(4-Chlorobenzyl)-4-methyl-6-(1-oxoquinolin-2-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 2-chloromethyl-quinoline-N-oxide for 5-phenyl-2-picolylchloride as starting material, the title compound was obtained as a solid, m.p.: 123°–128° C.

EXAMPLE 98

3-[1-(4-Chlorobenzyl)-4-methyl-6-(4-phenylbenzyloxy)-4,5-dihydro-1H-thiopyrano[2,3,4-c,d]indol-2-yl]-2,2-dimethylpropanoic acid Following the procedure described in Example 1, Method A, steps 6–7, but substituting 4-phenylbenzyl chloride for 5-phenyl-2-picolyl chloride as starting material, the title compound was obtained as a solid, m.p. 220°–221° C.

Analysis: Calc'd for C$_{36}$H$_{34}$ClNO$_3$S: C, 72.53; H, 5.75; N, 2.35; Found: C, 72.60; H, 5.87; N, 2.33.

EXAMPLE 99

3-[1-(4-Chlorobenzyl)-4-methyl-6-(6-phenylpyridin-2-ylmethoxy)-4,5-dihydro-1H-thiopyrano[2,3,4-c,d]indol-2yl]-2,2-dimethylpropanoic acid Following the procedure described in Example 1, Method A, steps 6–7, but substituting 6-phenyl-2-picolyl chloride for 5-phenyl-2-picolyl chloride as starting material, the title compound was obtained as a solid, m.p. 92°–95° C.

Analysis: Calc'd for $C_{35}H_{33}ClN_2O_3S$: C, 70.40; H, 5.57; N, 4.69; Found: C, 70.54; H, 5.56; N, 4.50.

EXAMPLE 100

3-[1-(4-Chlorobenzyl)-4-methyl-6-(4-phenylpyridin-2-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 4-phenyl-2-picolyl chloride for 5-phenyl-2-picolyl chloride as starting material, the title compound was obtained as a solid, m.p.: 249°–250° C. (dec).

Analysis: Calc'd for $C_{35}H_{31}ClN_2O_3S$: C, 70.63; H, 5.25; N, 4.71; S, 5.39; Found: C, 70.28; H, 5.71; N, 4.54; S, 5.16.

EXAMPLE 101

3-[1-(4-Chlorobenzyl)-4-methyl-6-(2-phenylpyridin-3-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 2-phenyl-3-picolyl chloride for 5-phenyl-2-picolyl chloride as starting material, the title compound was obtained as a solid, m.p.: 200°–201° C.

EXAMPLE 102

3-[1-(4-Chlorobenzyl)-4-methyl-6-(pyridin-2-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 2-picolyl chloride for 5-phenyl-2-picolyl chloride as starting material, the title compound was obtained as a solid, m.p.: 185°–186° C.

EXAMPLE 103

3-[1-(4-Chlorobenzyl)-4-methyl-6-pyridin-3-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 3-picolyl chloride for 5-phenyl-2-picolyl chloride as starting material, the title compound was obtained as a solid, m.p.: 136°–139° C.

Analysis: Calc'd for $C_{29}H_{29}ClN_2O_3S$: C, 66.85; H, 5.61; N, 5.78; S, 6.15; Found: C, 66.94; H, 5.66; N, 5.34; S, 5.84.

EXAMPLE 104

3-[1-(4-Chlorobenzyl)-4-methyl-6-(pyridin-4-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 4-picolyl chloride for 5-phenyl-2-picolyl chloride as starting material, the title compound was obtained as a solid, m.p.: 221°–222° C.

EXAMPLE 105

3-[1-(4-Chlorobenzyl)-4-methyl-6-(2-phenylpyridin-4-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 2-phenyl-4-picolyl chloride for 5-phenyl-2-picolyl chloride as starting material, the title compound was obtained as a solid, m.p.: 149°–169° C.

Analysis: Calc'd for $C_{35}H_{33}ClN_2O_3S$: C, 70.39; H, 5.57; N, 4.69; S, 5.37; Found: C, 70.85; H, 6.01; N, 4.51; S, 5.13.

EXAMPLE 106

3-[1-(4-Chlorobenzyl)-4-methyl-6-(5-methoxypyridin-2-ylmethoxy)-4,5-dihydro-1H-thiopyrano[2,3,4-c,d]indol-2-yl]-2,2-dimethylpropanoic acid Following the procedure described in Example 109, Steps 3–4, but substituting methyl iodide for benzyl chloride as starting material, the title compound was obtained as a solid, m.p. 193°–194° C.

EXAMPLE 107

3-[1-(4-Chlorobenzyl)-4-methyl-6-(5-carboxamidopyridin-2-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 5-cyano-2-picolyl chloride for 5-phenyl-2-picolyl chloride as starting material, the title compound was obtained as a solid, m.p.: 219°–222° C.

EXAMPLE 108

3-[1-(4-Chlorobenzyl)-4-methyl-6-[5-(N,N-dimethylcarboxamido)pyridin-2-ylmethoxy]-4,5-dihydro-1H-thiopyrano[2,3,4-c,d]indol-2-yl]-2,2-dimethylpropanoic acid Step 1: Methyl 3-[1-(4-chlorobenzyl)-4-methyl-6-(5-carbomethoxypyridin-2-ylmethoxy)-4,5-dihydro-1H-thiopyrano[2,3,4-c,d]indol-2-yl]-2,2-dimethylpropanoate Following the procedure described in Example 1, Method A, Step 6, but substituting 5-carbomethoxy-2-picolyl chloride for 5-phenyl-2-picolyl chloride as starting material, the title compound was obtained as a solid.

Step 2: Methyl 3-[1-(4-chlorobenzyl)-4-methyl-6-[5-(N,N-dimethylcarboxamido)pyridin-2-ylmethoxy]-4,5-dihydro-1H-thiopyrano[2,3,4-c,d]-indol-2-yl]-2,2-dimethylpropanoate The diester (173 mg) from Step 1 was added to a solution of dimethylaluminumdimethylamide (1 eq, 0.29 mmol) at 0° C. in $CH_2Cl_2$. Then more dimethylaluminumdimethylamide (0.87 mmol) was added. The mixture was stirred for 36 hours at r.t., then 1N HCl was slowly added. The mixture was extracted with 2×30 mL of EtOAc, the organic layer washed with 30 mL of 25% $NH_4OAc$, dried ($MgSO_4$) and concentrated. Chromatography of the residue on silica gel (EtOAc), afforded the title compound as an oil.

Step 3: 3-[1-(4-Chlorobenzyl)-4-methyl-6-[5-(N,N-dimethylcarboxamido)pyridin-2-ylmethoxy]-4,5-dihydro-1H-thiopyrano[2,3,4-c,d]indol-2-yl]-2,2-dimethylpropanoic acid Following the procedure described in Example 1, Method A, Step 7, but substituting the carboxamido ester from Step 2 for methyl 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate as starting material, the title compound was obtained as a solid, m.p.: 186°–187° C.

EXAMPLE 109

3-[1-(4-Chlorobenzyl)-4-methyl-6-(5-benzyloxypyridin-2-ylmethoxy)-4,5-dihydro-1H-thiopyrano[2,3,4-c,d]indol-2-yl]-2,2-dimethylpropanoic acid Step 1: Methyl 3-[1-(4-chlorobenzyl)-4-methyl-6-[5-(tert-butyldiphenylsilyloxy)pyridin-2-ylmethoxy]-4,5-dihydro-1H-thiopyrano-[2,3,4-c,d]indol-2-yl]-2,2-dimethylpropanoate Following the procedure described in Example 1, Method A, Step 6, but substituting 5-(t-butyldiphenylsilyloxy)-2-picolyl chloride for 5-phenyl-2-picolyl chloride as starting material, the title compound was obtained as an oil.

Step 2: Methyl 3-[1-(4-chlorobenzyl)-4-methyl-6-(5-hydroxypyridin-2-ylmethoxy)-4,5-dihydro-1H-thiopyrano[2,3,4-c,d]indol-2-yl]-2,2-dimethylpropanoate A solution of the silylether (650 mg) from Step 1 in THF (9 mL) was treated with 0.9 mL of a 1M THF solution of n—Bu$_4$NF. After stirring for 3 hours the mixture was extracted with 50 mL EtOAc. The organic layer was washed with 2×30 mL brine, dried (MgSO$_4$) and concentrated. Chromatography of the residue (EtOAc:hexane 1:1) afforded the title compound as an oil.

Step 3: Methyl 3-[1-(4-chlorobenzyl)-4-methyl-6-(5-benzyloxypyridin-2-yl)methoxy)-4,5-dihydro-1H-thiopyrano[2,3,4-c,d]indol-2-yl]-2,2-dimethylpropanoate To a solution of the phenol (80 mg) from Step 2 in 2 mL of DMF was added 4 mg of NaH. The mixture was stirred for 15 minutes, then 22 µL of benzyl chloride was added. After 45 minutes, brine (5 mL) was added to the mixture which was then extracted with Et$_2$O (50 mL). The organic layer was washed with brine (2×20 mL), dried (MgSO$_4$) and concentrated. Chromatography of the residue on silica gel (EtOAc/hexane 30/70) afforded the title compound as an oil.

Step 4: 3-[1-(4-Chlorobenzyl)-4-methyl-6-(5-benzyloxypyridin-2-ylmethoxy)-4,5-dihydro-1H-thiopyrano[2,3,4-c,d]indol-2-yl]-2,2-dimethylpropanoic acid Following the procedure described in Example 1, Method A, Step 7 but substituting the ester from Step 3 for methyl 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate as starting material, the title compound was obtained as a solid, m.p.: 192°–193° C.

EXAMPLE 110

3-[1-(4-Chlorobenzyl)-4-methyl-6-(5-cyanopyridin-2-ylmethoxy)-4,5-dihydro-1H-thiopyrano[2,3,4-c,d]indol-2-yl]-2,2-dimethylpropanoic acid Step 1: Methyl 3-[1-(4-chlorobenzyl)-4-methyl-6-(5-cyanopyridin-2-ylmethoxy)-4,5-dihydro-1H-thiopyrano[2,3,4-c,d]indol-2-yl]-2,2-dimethylpropanoate Following the procedure described in Example 1, Method A, Step 6, but substituting 5-cyano-2-picolyl chloride for 5-phenyl-2-picolyl chloride as starting material, the title compound was obtained as an oil.

Step 2: 3-[1-(4-Chlorobenzyl)-4-methyl-6-(5-cyanopyridin-2-ylmethoxy)-4,5-dihydro-1H-thiopyrano[2,3,4-c,d]indol-2-yl]-2,2-dimethylpropanoic acid The ester (150 mg) from Step 1 was dissolved in 10 mL of DMF and LiI (660 mg) was added. The mixture was refluxed for 18 hours. After cooling to 25° C., the mixture was poured into H$_2$O (25 mL), acidified with 1N HCl and extracted with Et$_2$O (2×25 mL). The organic layer was washed with brine (2×15 mL), dried (MgSO$_4$) and concentrated. The residue was chromatographed on silicic acid, (EtOAc/Hexane 30/70) affording the title compound as a solid, m.p.: 208°–209° C.

EXAMPLE 111

3-[1-(4-Chlorobenzyl)-4-methyl-6-(5-(n-butyl)pyridin-2-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 5-n-butyl-2-picolyl chloride for 5-phenyl-2-picolyl chloride as starting material, the title compound was obtained as a solid, m.p.: 204°–205° C.

EXAMPLE 112

3-[1-(4-Chlorobenzyl)-4-methyl-6-(6-chloropyridin-2-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 6-chloro-2-picolyl chloride for 5-phenyl-2-picolyl chloride as starting material, the title compound was obtained as a solid, m.p.: 151°–153° C.

EXAMPLE 113

3-[1-(4-Chlorobenzyl)-4-methyl-6-(6-chloro-5-phenylpyridin-2-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 6-chloro-5-phenyl-2-picolyl chloride for 5-phenyl-2-picolyl chloride as starting material, the title compound was obtained as a solid, m.p.: 147° C.

EXAMPLE 114

3-[1-(4-Chlorobenzyl)-4-methyl-6-(4-chloro-5-phenylpyridin-2-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 4-chloro-5-phenyl-2-picolyl chloride for 5-phenyl-2-picolyl chloride as starting material, the title compound was obtained as a solid, m.p.: 212° C.

EXAMPLE 115

3-[1-(4-Chlorobenzyl)-4-methyl-6-(4-methoxy-5-phenylpyridin-2-ylmethoxy)-4,5-dihydro-1H-thiopyrano[2,3,4-c,d]indol-2-yl]-2,2-dimethylpropanoic acid Step 1: Methyl 3-[1-(4-chlorobenzyl)-4-methyl-6-(4-methoxy-5-phenylpyridin-2-ylmethoxy)-4,5-dihydro-1H-thiopyrano[2,3,4-c,d]indol-2-yl]-2,2-dimethylpropanoate To a solution of 100 mg of methyl 3-[1-(4-chlorobenzyl)-4-methyl-6-(4-chloro-5-phenylpyridin-2-ylmethoxy)-4,5-dihydro-1H-thiopyrano[2,3,4-c,d]indol-2-yl]-2,2-dimethylpropanoate, from Example 114, in 2 mL of DMF was added 100 mg of MeONa and the resulting solution was refluxed for 2 hours. After cooling, the reaction mixture was poured onto H2O and extracted with EtOAc. The organic layer was washed with brine, dried, evaporated to dryness and purified using flash chromatography (hexane/EtOAc 4:1) to give the title product.

Step 2: 3-[1-(4-Chlorobenzyl)-4-methyl-6-(4-methoxy-5-phenylpyridin-2-ylmethoxy)-4,5-dihydro-1H-thiopyrano[2,3,4-c,d]indol-2-yl]-2,2-dimethylpropanoic acid Following the procedure described in Example 1, Method A, Step 7, but substituting the ester from Step 1 for methyl 3-[4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate as starting material, the title compound was obtained as a solid, m.p.: 160° C.

EXAMPLE 116

3-[1-(4-Chlorobenzyl)-4-methyl-6-(5-benzylpyridin-2-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 5-benzyl-2-picolyl chloride for 5-phenyl-2-picolyl chloride as starting material, the title compound was obtained as a solid, m.p.: 173°–175° C.

EXAMPLE 117

5-[3-[1-(4-Chlorobenzyl)-4-methyl-6-[3-(5-phenylpyridin-2-yl)propoxyl-4,5-dihydro-1H-thiopyrano[2,3,4-c,d]indol-2,-yl]-2,2-dimethylpropyl]-1H-tetrazole Step 1: Methyl 3-[1-(4-chlorobenzyl)-4-methyl-6-tert-butyldimethylsilyloxy-4,5-dihydro-1-H-thiopyrano[2,3,4-c,d]indol-2-yl]-2,2-dimethylpropanoate To a solution of 13.4 g of methyl 3-[1-(4-chlorobenzyl)-4-methyl-6-hydroxy-4,5-dihydro-1-H-thiopyrano[2,3,4-c,d]indol-2-yl]-2,2-dimethylpropanoate from Example 1, Step 5 in 20 mL of CH2Cl2 was added 5 mL of Et3N and 737 mg of DMAP followed by 4.8 g of t-butylchlorodimethylsilane. The reaction mixture was stirred at room temperature for 16 hours, diluted with CH2Cl2 washed successively with 1N HCl, and brine, dried over MgSO4, filtered and concentrated to give the title compound.

Step 2: 4-[1-(4-Chlorobenzyl)-4-methyl-6-t-butyldimethylsilyloxy-4,5-dihydro-1H-thiopyrano[2,3,4-c,d]indol-2-yl]-3,3-dimethylbutyronitrile Following the procedure outlined in Example 27, Steps 1–3 but substituting the ester from Step 1 for methyl 3-[1-(4-chlorobenzyl)-4-methyl-6-(5-phenylpyridin-2-ylmethoxy)-4,5-dihydro-1H-thiopyrano [2,3,4-c,d]indol-2-yl]-2,2-dimethylpropanoate the title compound was obtained.

Step 3: 4-[1-(4-Chlorobenzyl)-4-methyl-6-hydroxy-4,5-dihydro-1-H-thiopyrano[2,3,4-c,d]indol-2-yl]-3,3-dimethylbutyronitrile The nitrile from Step 2 was dissolved in dry THF (100 mL) and was treated at r.t. with 1 equivalent of a 1M solution of n-Bu4NF. The reaction mixture was stirred for 1 hour. Ethyl acetate (500 mL) was then added and the organic phase was washed successively with 1N HCl (2×150 mL), saturated aqueous solution of NaHCO3 (1×150 mL), brine (1×150 mL) and dried over MgSO4. After filtration and removal of the solvent the residue was purified using flash chromatography on silica gel (hexane/EtOAc 3:1) to give the title compound, m.p.: 82°–85° C.

Step 4: 4-[1-(4-Chlorobenzyl)-4-methyl-6-(2,2-diethoxyethoxy)-4,5-dihydro-1H-thiopyrano[2,3,4-c,d]indol-2yl]-3,3-dimethylbutyronitrile To a solution of the phenol from Step 3 (1 g) in dry DMF (25 mL) was added at room temperature 190 mg of NaH (60% dispersion in mineral oil) followed by bromoacetaldehyde diethylacetal 1.1 mL. After 3 hours the mixture was poured onto a saturated aqueous solution of NaHCO3 and extracted with 2×50 mL EtOAc. The combined layers were washed with brine, dried over MgSO4, filtered and concentrated. Chromatography of the residue on silica gel (hexane:EtOAc 3:1) gave the title compound.

Step 5: 4-[1-(4-Chlorobenzyl)-4-methyl-6-(formylmethoxy)-4,5-dihydro-1-H-thiopyrano[2,3,4-c,d]indol-2-yl]-3,3-dimethylbutyronitrile The diethyl acetal from Step 4 (1.1 g) was dissolved in 15 mL of THF and treated with 6N HCl (5 mL). The reaction mixture was heated at 50° C. for 30 minutes, then added to a saturated aqueous solution of NaHCO3 and extracted with EtOAc (3×50 mL). The combined organic phase was washed successively with H2O (1×50 mL), brine (1×50 mL) and dried over MgSO4. After removal of the solvent the residue was purified using flash chromatography (hexane:EtOAc 3:2) to give the title compound.

Step 6: 4-[1-(4-Chlorobenzyl)-4-methyl-6-[3-(5-phenylpyridin-2-yl)-2-propenoxy]-4,5-dihydro-1-H-thiopyrano[2,3,4-c,d]indol-2-yl]-3,3-dimethylbutyronitrile The aldehyde from Step 5 (426 mg) was added to a solution of 5-phenylpyridin-2-ylmethylenetriphenylphosphorane ylide at −70° C. prepared by the addition of 0.72 mL of 1.4M n-BuLi in hexane to 5-phenylpyridine-2-ylmethyltriphenylphosphonium bromide (510 mg) in dry THF 15 mL and stirred for 15 minutes. The cooling bath was then removed and the reaction mixture was stirred for 1 hour. A saturated solution of NH4Cl (1 mL) was then added and the mixture was extracted with EtOAc (3×20 mL). The combined organic phase was washed successively with H2O (30 mL) and brine (30 mL) and dried over MgSO4. After removal of the solvent, purification using flash chromatography (hexane:EtOAc 85:15) gave the title compound as a mixture of cis and trans olefins.

Step 7: 4-[1-(4-Chlorobenzyl)-4-methyl-6-[3-(5-phenylpyridin-2yl)propoxy]-4,5-dihydro-1-H-thiopyrano[2,3,4-c,d]indol-2-yl]-3,3-dimethylbutyronitrile The olefin from Step 6, 171 mg, was dissolved in 2 mL of MeOH and 2 mL of EtOAc then 2 mg of 10% Pd on carbon was added and one atmosphere of hydrogen was applied for 4 hours. Filtration through celite using EtOAc as solvent, evaporation and purification using flash chromatography (hexane:EtOAc 4:1) gave the title compound.

Step 8: 5-[3-[1-(4-Chlorobenzyl)-4-methyl-6-[3-(5-phenylpyridin-2-yl)propoxy]-4,5-dihydro-1-H-thiopyrano[2,3,4-c,d]indol-2-yl]-2,2-dimethylpropyl]-1H-tetrazole Following the procedure described in Example 28 but substituting the nitrile from Step 7 for 4-[1-(4-chlorobenzyl)-4-methyl-6-(5-phenylpyridin-2-ylmethoxy)-4,5-dihydro-1H-thiopyrano[2,3,4-c,d]indol-2- yl]-3,3-dimethylbutyronitrile as starting material the title compound was obtained as a solid, m.p.: 100°–105° C. (dec).

EXAMPLE 118

3-[1-(4-Chlorobenzyl)-4-methyl-6-(isoquinolin-3-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 3-chloromethylisoquinoline for 5-phenyl-2-picolyl chloride as starting material, the title compound was obtained as a solid, m.p.: 209°–211° C.

Analysis: Calc'd for $C_{33}H_{31}ClN_2O_3S$: C, 69.40; H, 5.47; N, 4.90; S, 5.61; Found: C, 69.41; H, 5.84; N, 5.15; S, 5.60.

EXAMPLE 119

3-[1-(4-Chlorobenzyl)-4-methyl-6-(quinolin-4-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 4-bromomethylquinoline for 5-phenyl-2-picolyl chloride as starting material, the title compound was obtained as a solid, m.p.: 235° C. (dec).

EXAMPLE 120

3-[1-(4-Chlorobenzyl)-4-methyl-6-(1,8-naphthyridine-2-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 2-chloromethyl-1,8-naphthyridine for 5-phenyl-2-picolyl chloride as starting material, the title compound was obtained as a solid, m.p.: 135°–140° C.

EXAMPLE 121

5-[3-[1-(4-Chlorobenzyl)]-4-methyl-6-[5-(4-chlorophenyl)pyridin-2-ylmethoxy]-4,5-dihydro-1H-thiopyrano[2,3,4-c,d]indol-2-yl]-2,2-dimethylpropyl]-1H-tetrazole Following the procedure described in Example 117, Step 4 and Example 28, but substituting 5-(4-chlorophenyl)-2-picolyl chloride for bromoacetaldehyde diethylacetal as starting material, the title compound was obtained as a solid, m.p.: 97°–100° C.

EXAMPLE 122

3-[1-(4-Chlorobenzyl)-4-methyl-6-[4-(pyridin-2-yl)benzyloxy]-4,5-dihydro-1H-thiopyrano[2,3,4-c,d]indol-2-yl]-2,2-dimethylpropanoic acid Following the procedure described in Example 1, Method A, Steps 6–7, but substituting 4-(pyridin-2-yl)benzyl chloride for 5-phenyl-2-picolyl chloride as starting material, the title compound was obtained as a solid, m.p.: 231°–233° C.

Analysis: Calc'd for $C_{35}H_{33}ClN_2O_3S$: C, 70.40; H, 5.57; N, 4.69; Found: C, 70.27; H, 5.67; N, 4.45.

EXAMPLE 123

3-[1-(4-Chlorobenzyl)-4-methyl-6-(thien-2-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting thien-2-yl-methyl methanesulfonate for 5-phenyl-2-picolyl chloride as starting material, the title compound was obtained as a solid, m.p.: 163°–164° C.

Analysis: Calc'd for $C_{28}H_{28}ClNO_3S_2$: C, 63.92; H, 5.36; N, 2.66; S, 12.19; Found: C, 63.55; H, 5.73; N, 2.78; S, 12.35.

EXAMPLE 124

3-[1-(4-Chlorobenzyl)-4-methyl-6-(benzyloxy)-4,5-dihydro-1H-thiopyrano[2,3,4-c,d]indol-2-yl]-2,2-dimethylpropanoic acid Following the procedure described in Example 1, Method A, Steps 6–7, but substituting benzyl chloride for 5-phenyl-2-picolyl chloride as starting material, the title compound was obtained as a solid, m.p.: 168°–169° C.

EXAMPLE 125

3-[1-(4-Chlorobenzyl)-4-methyl-6-(3-phenylpropoxy)-4,5-dihydro-1H-thiopyrano[2,3,4-c,d]indol-2-yl]-2,2-dimethylpropanoic acid Following the procedure described in Example 1, Method A, Steps 6–7, but substituting 3-phenylpropyl bromide for 5-phenyl-2-picolyl chloride as starting material, the title compound was obtained as a solid, m.p.: 146°–148° C.

EXAMPLE 126

3-[1-(4-Chlorobenzyl)-4-methyl-6-(3,5-dimethylisoxazol-4-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 4-chloromethyl-3,5-dimethylisoxazole for 5-phenyl-2-picolyl chloride as starting material, the title compound was obtained as a solid, m.p.: 167°–168° C.

Analysis: Calc'd for $C_{29}H_{31}ClN_2O_4S$: C, 64.61; H, 5.80; N, 5.20; Found: C, 64.86; H, 5.76; N, 5.15.

EXAMPLE 127

3-[1-(4-Chlorobenzyl)-4-methyl-6-(2-(4-chlorophenyl)-thiazol-4-ylmethoxy)-4,5-dihydro-1H-thiopyrano[2,3,4-c,d]indol-2-yl]-2,2-dimethylpropanoic acid Following the procedure described in Example 1, Method A, Steps 6–7, but substituting 4-chloromethyl-2-(4-chlorophenyl)thiazole for 5-phenyl-2-picolyl chloride as starting material, the title compound was obtained as a solid, m.p.: 207°–208° C.

EXAMPLE 128

3-[1-(4-Chlorobenzyl)-4-methyl-6-(1-methyl-5-phenyl-1,2,3,6-tetrahydropyridin-2-ylmethoxy)-4,5-dihydro-1H-thiopyrano[2,3,4-c,d]indol-2-yl]-2,2-dimethylpropanoic acid Step 1: Methyl 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate methiodide To a solution of methyl 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate (150 mg) from Example 1, Method A, Step 6 in acetone (5 mL) there was added methyl iodide (1 mL) and the mixture was heated to 65° C., after 2 hours; more methyl iodide was added (0.5 mL) and heating was continued for a further hour. The mixture was cooled and filtered to afford the methiodide as a yellow solid.

Step 2: Methyl 3-[1-(4-chlorobenzyl)-4-methyl-6-(1-methyl-5-phenyl-1,2,3,6-tetrahydropyridin-2-yl methoxy)-4,5-dihydro-1H-thiopyrano [2,3,4-c,d]indol-2-yl]-2,2-dimethylpropanoate To the methiodide from Step 1 (140 mg, 0.186 mmol) suspended in MeOH (5 mL) there was added NaBH$_4$ (38 mg, 1 mmole) and the mixture was stirred at room temperature for 30 minutes. The MeOH was evaporated away and the residue was partitioned between water and EtOAc. The crude material obtained from the organic phase was chromatographed on silica gel, eluting with EtOAc, to afford the title product as a yellow thick oil.

Step 3: 3-[1-(4-Chlorobenzyl)-4-methyl-6-(1-methyl-5-phenyl-1,2,3,6-tetrahydropyridin-2-ylmethoxy)-4,5-dihydro-1H-thiopyrano[2,3,4-c,d]indol-2-yl]-2,2-dimethylpropanoic acid Following the procedure described in Example 1, Method A, Step 7 but substituting the product from Step 2 above for methyl 3-[1-(4-chlorobenzyl-4-methyl-6-(5-phenylpyridin-2-ylmethoxy)-4,5-dihydro-1H-thiopyrano[2,3,4-c,d]indol-2-yl]-2,2-dimethylpropanoate as starting material, the title compound was obtained as a cream-colored solid, m.p.: 170° C. (dec).

EXAMPLE 129

3-[1-(4-Chlorobenzyl)-4-methyl-6-(cyclohexylmethoxy)-4,5-dihydro-1H-thiopyrano[2,3,4-c,d]indol-2-yl]-2,2-dimethylpropanoic acid Following the procedure described in Example 1, Method A, Steps 6-7, but substituting cyclohexylmethyl bromide for 5-phenyl-2-picolyl chloride as starting material, the title compound was obtained as a solid, m.p.: 181°-183° C.

Analysis: Calc'd for C$_{30}$H$_{36}$ClNO$_3$S: C, 68.48; H, 6.90; N, 2.66; S, 6.09; Found: C, 68.54; H, 6.89; N, 2.85; S, 6.05.

EXAMPLE 130

3-[1-(4-Chlorobenzyl)-4-methyl-6-(N-methyl-N-phenethylcarboxamido-methoxy)-4,5-dihydro-1-H-thiopyrano[2,3,4-c,d]indol-2-yl]-2,2-dimethylpropanoic acid Step 1: Methyl 3-[1-(4-Chlorobenzyl)-4-methyl-6-(carbomethoxymethoxy)-4,5-dihydro-1-H-thiopyrano[2,3,4c,d]indol-2-yl]-2,2-dimethylpropanoate Following the procedure described in Example 1, Method A, Step 6, but substituting methyl bromoacetate for 5-phenyl-2-picolyl chloride as starting material, the title compound was obtained as an oil.

Step 2: Methyl 3-[1-(4-chlorobenzyl)-4-methyl-6-(carboxymethoxy)-4,5-dihydro-1-H-thiopyrano[2,3,4-c,d]indol-2-yl]-2,2-dimethylpropanoate The ester from Step 1 (900 mg) was dissolved in MeOH (20 mL) then treated with 1N LiOH (2.7 mL) and the resulting mixture was stirred at r.t. for 1 hour. A solution of 1N HCl was added and the reaction mixture was extracted with EtOAc (3×50 mL). The combined organic phase was washed with brine and dried (MgSO$_4$). Removal of the solvent gave the title compound.

Step 3: Methyl 3-[1-(4-chlorobenzyl)-4-methyl-6-(N-methyl-N-phenethylcarboxamidomethoxy)-4,5-dihydro-1-H-thiopyrano[2,3,4-c,d]indol-2-yl]-2,2-dimethylpropanoate The acid from Step 2, 300 mg, was dissolved in CH$_2$Cl$_2$ (15 mL), DMAP (15 mg) was added followed by N-methylphenethylamine (0.1 mL) and dicyclohexylcarbodimide (152 mg). The resulting reaction mixture was stirred for 2 hours. After removal of the solvent the residue was applied onto a silica gel column which was then eluted with hexane:EtOAc: 3:2 to give the title compound.

Step 4: 3-[1-(4-Chlorobenzyl)-4-methyl-6-(N-methyl-N-phenethylcarboxamidomethoxy)-4,5-dihydro-1-H-thiopyrano[2,3,4-c,d]indol-2-yl]-2,2-dimethylpropanoic acid Following the procedure described in Example 1, Method A, Step 7, but substituting the ester from Step 3 for methyl 3-[1-(4-chlorobenzyl)-4-methyl-6-(5-phenylpyridin-2-ylmethoxy)-4,5-dihydro-1H-thiopyrano [2,3,4-c,d]indol-2-yl]-2,2-dimethylpropanoate as starting material, the title compound was obtained as a solid, m.p.: 72.5° C.

EXAMPLE 131

3-[1-(4-Chlorobenzyl)-4-methyl-6-(naphth-2-ylmethoxy)-4,5-dihydro-1H-thiopyrano[2,3,4-c,d]indol-2-yl]-2,2-dimethylpropanoic acid Following the procedure described in Example 1, Method A, Steps 6-7, but substituting 2-bromomethylnaphthalene for 5-phenyl-2-picolyl chloride as starting material, the title compound was obtained as a solid, m.p.: 183° C.

EXAMPLE 132

5-[3-[1-(4-Chlorobenzyl)-4-methyl-6-(naphth-2-ylmethoxy)-4,5-dihydro-1H-thiopyrano[2,3,4-c,d]indol-2-yl]-2,2-dimethylpropyl]-1H-tetrazole Following the procedure described in Example 117, Step 4 and Example 28 but substituting 2-bromomethylnaphthalene for bromoacetaldehyde diethyl acetal as starting material, the title compound was obtained as a solid, m.p.: 126° C.

EXAMPLE 133

5-[3-[1-(4-Chlorobenzyl)-4-methyl-6-(5-phenyloxazol-2-ylmethoxy)-4,5-dihydro-1H-thiopyrano[2,3,4-c,d]indol-2-yl]-2,2-dimethylpropyl]-1H-tetrazole Following the procedure described in Example 117, Step 4 and Example 28 but substituting 2-chloromethyl-5-phenyloxazole for bromoacetaldehyde diethylacetal as starting material, the title compound was obtained as a solid, m.p.: 110° C. (dec).

EXAMPLE 134

5-[3-[1-(4-Chlorobenzyl)-4-methyl-6-[5-(4-methoxyphenyl)pyridin-2-ylmethoxy]-4,5-dihydro-1H-thiopyrano[2,3,4-c,d]indol-2-yl]-2,2-dimethylpropyl]]-1H-tetrazole Following the procedure described in Example 117, Step 4 and Example 28 but substituting 5-(4-methoxyphenyl)-2-picolyl chloride for bromoacetaldehyde diethylacetal as starting material, the title compound was obtained as a solid, m.p.: 110°-115° C.

EXAMPLE 135

5-[3-[1-(4-Chlorobenzyl)-4-methyl-6-[5-(1-naphthyl)-pyridin-2-ylmethoxy]-4,5-dihydro-1H-thiopyrano[2,3,4-c,d]indol-2-yl]-2,2-dimethylpropyl]-1H-tetrazole Following the procedure described in Example 117, Step 4 and Example 28 but substituting 5-(1-naphthyl)-2-picolyl chloride for bromoacetaldehyde diethylacetal as starting material, the title compound was obtained as a solid, m.p.: 210°–212° C. (dec).

EXAMPLE 136

5-[3-[1-(4-Chlorobenzyl)-4-methyl-6-(5-phenylpyrazin-2-ylmethoxy)-4,5-dihydro-1H-thiopyrano[2,3,4-c,d]indol-2-yl]-2,2-dimethylpropyl]-1H-tetrazole Following the procedure described in Example 117, Step 4 and Example 28 but substituting 2-chloromethyl-5-phenylpyrazine for bromoacetaldehyde diethylacetal as starting material, the title compound was obtained as a solid, m.p.: 210° C. (dec).

EXAMPLE 137

5-[3-[1-(4-Chlorobenzyl)-4-methyl-6-(5-phenylpyrimidin-2-ylmethoxy)-4,5-dihydro-1H-thiopyrano[2,3,4-c,d]indol-2-yl]-2,2-dimethylpropyl]-1H-tetrazole Following the procedure described in Example 117, Step 4 and Example 28 but substituting 2-chloromethyl-5-phenylpyrimidine for bromoacetaldehyde diethylacetal as starting material, the title compound was obtained as a solid, m.p.: 226° C.

EXAMPLE 138

5-[3-[1-(4-Chlorobenzyl)-4-methyl-6-(2-phenylfuro[3,2-b]pyridin-5-ylmethoxy)-4,5-dihydro-1H-thiopyrano[2,3,4-c,d]indol-2-yl]-2,2-dimethylpropyl]-1H-tetrazole Following the procedure described in Example 117, Step 4 and Example 28, but substituting 5-chloromethyl-2-phenylfurano[3,2-b]pyridine for bromoacetaldehyde diethylacetal as starting material, the title compound was obtained as a solid, m.p.: 210°–212° C.

EXAMPLE 139

3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoic acid S,S-dioxide Step 1: Methyl 3-[6-acetoxy-1-(4-chlorobenzyl)-4-methyl-4,5-dihydro-1H-thiopyrano[2,3,4-c,d]indol-2-yl]-2,2-dimethylpropanoate The phenol from Example 1, Method A, Step 5 (395 mg) was dissolved in 10 mL CH$_2$Cl$_2$ at r.t. under nitrogen atmosphere and treated sequentially with pyridine (0.36 mL) and acetyl chloride (95 μL). After 30 minutes, the mixture was poured onto 1N HCl and extracted (3×) with EtOAc. The organic layers were washed with water, dried (MgSO$_4$) and evaporated. Recrystallisation of the residue from EtOAc/hexane 1:2 provided the title compound.

Step 2: Methyl 3-[6-acetoxy-1-(4-chlorobenzyl)-4-methyl-4,5-dihydro-1H-thiopyrano[2,3,4-c,d]indol-2-yl]-2,2-dimethylpropanoate S,S-dioxide A solution of the acetate from Step 1 (111 mg) and 3-chloroperoxybenzoic acid (148 mg) in 2 mL of CH$_2$Cl$_2$ was stirred for 24 hours at room temperature then poured onto saturated NaHCO$_3$ solution. After extraction with EtOAc (3×) the organic layers were washed with brine (2×), dried (MgSO$_4$) and concentrated in vacuo. Column chromatography of the residue (EtOAc/hexane 1:4) provided the title compound as a solid.

Step 3: Methyl 3-[1-(4-chlorobenzyl)-6-hydroxy-4-methyl-4,5-dihydro-1H-thiopyrano[2,3,4-c,d]indol-2-yl]-2,2-dimethylpropanoate S,S-dioxide The sulfone from Step 2 (68 mg), K$_2$CO$_3$ (90 mg) and MeOH (2 mL) were combined and heated to 60° C. under nitrogen for 1 hour. The solution was cooled, poured onto 1N HCl, extracted with EtOAc (3×) and the organic layer washed twice with brine. Removal of the dried (MgSO$_4$) solvent provided the title compound as a solid.

Step 4: 3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoic acid S,S-dioxide Following the procedure described in Example 1, Method A, Steps 6 and 7 but substituting the phenol from Step 3 for methyl 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate as starting material gave the title compound as a solid, m.p.: 232° C.

EXAMPLE 140

3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoic acid S-oxide Step 1: Methyl 3-[6-acetoxy-1-(4-chlorobenzyl)-4-methyl-4,5-dihydro-1H-thiopyrano[2,3,4-c,d]indol-2-yl]-2,2-dimethylpropanoate S-oxide A solution of the acetate from Example 139, Step 1 (209 mg) and 3-chloroperoxybenzoic acid (93 mg) in 4 mL CH$_2$Cl$_2$ was stirred for 16 hours at room temperature then poured onto saturated NaHCO$_3$ solution. After extraction with EOAc (3×) the organic layers were washed with brine (2×), dried (MgSO$_4$) and evaporated. Chromatography of the residue (EtOAc/hexane 1:2) provided the title compound as a solid.

Step 2: 3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoic acid S-oxide Following the procedure described in Example 139, Step 3 and Example 1, Method A, Steps 6 and 7 but substituting the sulfoxide from Step 1 for methyl 3-[6-acetoxy-1-(4-chlorobenzyl)-4-methyl-4,5-dihydro-1H-thiopyrano[2,3,4-c,d]indol-2-yl]-2,2-dimethylpropanoate S,S-dioxide as starting material, the title compound was obtained as a solid, m.p.: 118°–124° C.

EXAMPLE 141

(R*,S*)
3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoic acid S-oxide Step 1: (R*,S*) Methyl 3-[6-acetoxy-1-(4-chlorobenzyl)-4-methyl-4,5-dihydro-1H-thiopyrano[2,3,4-c,d]indol-2-yl]-2,2-dimethylpropanoate S-oxide The sulfoxide from Example 140, Step 1 (mixture of diastereomers) was chromatographed on silica gel (hexane/EtOAc 1:2) and the less polar sulfoxide collected to provide (after removal of the solvent) the title compound as a solid.

Step 2: (R*,S*) 3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoic acid S-oxide Following the procedure described in Example 139, Step 3 and Example 1, Method A, Steps 6 and 7 but substituting the sulfoxide from Step 1 for methyl 3-[6-acetoxy-1-(4-chlorobenzyl)-4-methyl-4,5-dihydro-1H-thiopyrano[2,3,4-c,d]indol-2-yl]-2,2-dimethylpropanoate S,S-dioxide as starting material, the title compound was obtained as a solid, m.p.: 197°–198° C.

Analysis: Calc'd for $C_{35}H_{33}ClN_2O_4S$: C, 68.56; H, 5.42; N, 4.57; Found: C, 68.39; H, 5.47; N, 4.56.

EXAMPLE 142

(R*,R*)
3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate S-oxide Step 1: (R*,R*) Methyl 3-[6-acetoxy-1-(4-chlorobenzyl)-4-methyl-4,5-dihydro-1H-thiopyrano [2,3,4-c,d]indol-2-yl]-2,2-dimethylpropanoate S-oxide The sulfoxide from Example 140, Step 1 (mixture of diastereomers) was chromatographed on silica gel (hexane/EtOAc 1:2) and the more polar sulfoxide collected to provide (after removal of the solvent) the title compound as a solid.

Step 2: (R*,R*) 3-[1-(4-Chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoic acid S-oxide Following the procedure described in Example 139, Step 3 and Example 1, Method A, Steps 6 and 7 but substituting the sulfoxide from Step 1 for methyl 3-[6-acetoxy-1-(4-chlorobenzyl-4-methyl-4,5-dihydro-1H-thiopyrano[2,3,4c,d]indol-2-yl]-2,2-dimethylpropanoate S,S-dioxide as starting material, the title compound was obtained as a solid, m.p.: 132°–135° C.

Analysis: Calc'd for $C_{35}H_{33}ClN_2O_4S$: C, 68.56; H, 5.42; N, 4.57; Found: C, 68.83; H, 5.63; N, 4.38.

EXAMPLE 143

3-[1-(4-Chlorobenzyl)-7-(5-phenylpyridin-2-ylmethoxy)-1,4-dihydrothiepino[2,3,4-c,d]indol-2-yl]-2,2-dimethylpropanoic acid Step 1: Methyl 3-[1-(4-chlorobenzyl)-3-(2-formylethylthio)-5-hydroxyindol-2-yl]-2,2-dimethylpropanoate To a solution of 3:3'-dithiodipropionaldehyde (J. Org. Chem., 1967, 32, 3425) (490 mg, 2.75 mmol) in 1,2-dichloroethane (7.5 mL), at room temperature there was added sulfuryl chloride (338 mg, 2.5 mmol) and the resulting yellow solution stirred for 5 minutes. A portion of this solution (6 μL) was then added dropwise, at 0° C., to a solution of methyl 3-[1-(4-chlorobenzyl)-5-hydroxyindol-2-yl]-2,2-dimethylpropanoate from Example 91, Step 2, (988 mg, 2.66 mmol) in DMF (12 mL) and the resulting mixture was stirred at 0° C. for 1 hour. The mixture was then diluted with $H_2O$ (50 mL) and extracted twice with $CH_2Cl_2$. The organic phases were washed with $H_2O$ 3 times, then dried ($MgSO_4$) and evaporated to dryness. The crude product was used without further purification.

Step 2: Methyl 3-[1-(4-chlorobenzyl)-7-hydroxy-1,4-dihydrothiepino[2,3,4-c,d]indol-2-yl]-2,2-dimethylpropanoate The crude product from Step 1 was dissolved in $Et_2O$ (50 mL) and the solution saturated with HCl gas. After 30 minutes the mixture was washed with $H_2O$ four times, dried and evaporated to a residue which was chromatographed on silica gel, eluting with a 2:1 mixture of hexane-EtOAc, to afford the title compound as a thick oil.

Step 3: 3-[1-(4-Chlorobenzyl)-7-(5-phenylpyridin-2-ylmethoxy)-1,4-dihydrothiepino[2,3,4-c,d]indol-2-yl]-2,2-dimethylpropanoic acid Following the procedure described in Example 1, Method A, Steps 6 and 7, but substituting the product from Step 2 for methyl 3-[1-(4-chlorobenzyl)-4-methyl-6-hydroxy-4,5-dihydro-1H-thiopyrano [2,3,4-c,d]indol-2-yl]-2,2-dimethylpropanoate as starting material, the title compound was obtained as a solid, m.p.: 220°–222° C.

EXAMPLE 144

3-[1-(4-Chlorobenzyl)-7-(5-phenylpyridin-2-ylmethoxy)-1,4,5,6-tetrahydrothiepino[2,3,4-c,d]indol-2-yl]-2,2-dimethylpropanoic acid Step 1: Methyl 3-[1-(4-chlorobenzyl)-7-hydroxy-1,4,5,6-tetrahydrothiepino[2,3,4-c,d]indol-2-yl]-2,2-dimethylpropanoate A mixture of methyl 3-[1-(4-chlorobenzyl)-7-hydroxy-1,4-dihydrothiepino[2,3,4-c,d]indol-2-yl]-2,2-dimethylpropanoate from Example 143, Step 2 (330 mg) and 10% Pd on charcoal (500 mg) in MeOH (20 mL) was hydrogenated at 40 psi for 16 hours. After filtration of the catalyst, the filtrate was evaporated to afford the title product as a thick oil.

Step 2: 3-[1-(4-Chlorobenzyl)-7-(5-phenylpyridin-2-ylmethoxy)-1,4,5,6-tetrahydrothiepino[2,3,4-c,d]indol-2-yl]-2,2-dimethylpropanoic acid Following the procedure described in Example 1, Method A, Steps 6 and 7 but substituting the product from Step 1 for methyl 3-[1-(4-chlorobenzyl)-4-methyl-6-hydroxy-4,5-dihydro-1H-thiopyrano [2,3,4-c,d]indol-2-yl]-2,2-dimethylpropanoate as starting material, the title compound was obtained as a solid.

Analysis: Calc'd for $C_{35}H_{33}ClN_2O_3S$: C, 70.39; H, 5.57; N, 4.69; S, 5.37; Cl, 5.94; Found: C, 70.04; H, 5.87; N, 4.61; S, 5.30; Cl, 6.03.

EXAMPLE 145

3-[1-(4-Chlorobenzyl)-4-methyl-6-(5-phenylpyridin-2-ylmethylthio)-4,5-dihydro-1H-thiopyrano[2,3,4-c,d]indol-2-yl]-2,2-dimethylpropanoic acid Step 1: 3-[6-Dimethylthiocarbamoyloxy-4-methyl-4,5-dihydro-1H-thiopyrano[2,3,4-c,d]indol-2-yl]-2,2-dimethylpropanoic acid, lactam To a suspension of NaH (60% dispersion in oil, 1.045 g, 26.1 mmol) in DMF (70 mL) there was added 3-(4-methyl-6-hydroxy-4,5-dihydro-1H-thiopyrano [2,3,4-c,d]indol-2-yl]-2,2-dimethylpropanoic acid lactam (from Example 1, Method B, Step 4; 6.0 g, 20.9 mmol) and the mixture was stirred at r.t. for 45 minutes. The mixture was cooled to 0° C., and there was added in portions dimethylthiocarbamoyl chloride (3.23 g, 26.1 mmol). Stirring was continued at r.t. 16 hours, the mixture was quenched with $H_2O$ and extracted with $Et_2O$ 3 times. The combined organic extracts were washed with $H_2O$ 3 times, dried and evaporated to a residue which was stirred with $Et_2O$ (50 μL) for 30 minutes and filtered to afford the title compound as a beige solid.

Step 2: 3-[6-Dimethylcarbamoylthio-4-methyl-4,5-dihydro-1H-thiopyrano[2,3,4-c,d]indol-2-yl]-2,2-dimethylpropanoic acid, lactam The product from Step 1 (5.59 g) was heated neat to 210°-215° C. for 20 hours. After cooling, the product was crystallized from EtOAc to afford the title compound as a yellow solid.

Step 3: Methyl 3-(6-mercapto-4-methyl-4,5-dihydro-1H-thiopyrano[2,3,4-c,d]indol-2-yl]-2,2-dimethylpropanoate To a solution of Na (722 mg, 31.4 mmol) in MeOH (75 mL) there was added the product from Step 2 (2.94 g, 7.86 mmol) and the mixture was refluxed under a nitrogen atmosphere for 18 hours. More Na (200 mg) in MeOH (10 mL) was added and refluxing was continued for another 24 hours. The MeOH was evaporated and the residue was partitioned between $H_2O$ and $Et_2O$. The aqueous phase was acidified with 6N HCl and extracted with $Et_2O$ (3×). These extracts were washed with $H_2O$ (3×), dried and evaporated to an oily residue. This was esterified by dissolving in MeOH (60 mL), adding thionyl chloride (1.4 g, 11.8 mmol) and stirring at room temperature for 5 hours. The MeOH was evaporated and the residue triturated with $Et_2O$ and filtered to afford the disulfide of the title compound. This was suspended in dioxane (15 mL) and $H_2O$ (2 mL), and there was added triphenyl phosphine (670 mg, 2.56 mmol) and 6N HCl (2 drops). The mixture was heated to 60° C. for 15 minutes, then at room temperature for 1 hour. The mixture was diluted with EtOAc (50 mL) and filtered. The residue obtained on evaporation of the filtrate was chromatographed on silica gel, eluting with a 3:1 mixture of hexane and EtOAc, to afford the title compound as a thick oil.

Step 4: Methyl 3-[4-methyl-6-(5-phenylpyridin-2-ylmethylthio)-4,5-dihydro-1H-thiopyrano[2,3,4-c,d]indol-2-yl]-2,2-dimethylpropanoate A mixture of product from Step 3 (1.1 g, 3.28 mmol), 5-phenyl-2-picolyl chloride (1.67 g, 8.2 mmol) and $Et_3N$ (1.01 g, 10 mmol) in THF (30 mL) was stirred at r.t. under a nitrogen atmosphere overnight. The THF was evaporated and the residue was dissolved in EtOAc (75 mL). The solution was washed with $H_2O$ 3 times, dried and evaporated to a residue which was chromatographed on silica gel, eluting with a 2:1 mixture of hexane and EtOAc, to afford the title compound as a yellow solid.

Step 5: Methyl 3-[1-(4-chlorobenzyl)-4-methyl-6-(5-phenylpyridin-2-ylmethylthio)-4,5-dihydro-1H-thiopyrano[2,3,4-c,d]indol-2-yl]-2,2-dimethylpropanoate To a solution of product from Step 4 (502 mg, 1 mmol) in DMF (15 mL), at 0° C. there was added 36 mg NaH powder (1.5 mmol) and the mixture was stirred at 0° C. for 5 minutes. There was added a solution of 4-chlorobenzylchloride (483 mg, 3 mmol) in DMF (1.5 mL) and stirring was continued for 75 minutes at 0° C. Water was added (100 mL), the mixture was acidified with 2N HCl, and extracted twice with $Et_2O$. These extracts afforded a crude product which was chromatographed on silica gel, eluting with a 2:2 mixture of hexane and EtOAc, to afford the title product as a thick oil.

Step 6: 3-[1-(4-Chlorobenzyl)-4-methyl-6-(5-phenylpyridin-2-ylmethylthio)-4,5-dihydro-1H-thiopyrano[2,3,4-c,d]indol-2-yl-2,2-dimethylpropanoic acid Following the procedure described in Example 1, Method A, Step 7, but substituting the product from Step 5 above for methyl 3-[1-(4-chlorobenzyl-4-methyl-6-(5-phenylpyridin-2-ylmethoxy)-4,5-dihydro-1H-thiopyrano[2,3,4-c,d]indol-2-yl]-2,2-dimethylpropanoate as starting material, the title compound was obtained as a cream-colored solid, m.p.: 194°-196° C.

EXAMPLE 146

4-[1-(4-Chlorobenzyl)-4-methyl-6-(5-phenylpyridin-2ylmethythio)-4,5-dihydro-1H-thiopyrano[2,3,4-c,d]indol-2-yl]-3,3-dimethylbutanoic acid Following the procedures described in Example 27, Steps 1-4, but substituting the ester from Example 145, Step 5 for 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropanoate as starting material, the title compound was obtained as a cream-colored solid, m.p.: 167°-169° C.

EXAMPLE 147

5-[3-[1-(4-Chlorobenzyl)-4-methyl-6-(5-phenylpyridin-2-ylmethylthio)-4,5-dihydro-1H-thiopyrano[2,3,4-c,d]indol-2-yl]-2,2-dimethylpropyl]-1H-tetrazole Following the procedure described in Example 28, but substituting 4-[1-(4-chlorobenzyl)-4-methyl-6-(5-phenylpyridin-2-ylmethylthio)-4,5-dihydro-1H-thiopyrano[2,3,4-c,d]indol-2-yl]-3,3-dimethylbutyronitrile from Example 146 for 4-[1-(4-chlorobenzyl)-4-methyl-6-(5-phenylpyridin-2-ylmethoxy)-4,5-dihydro-1H-thiopyrano[2,3,4-c,d]indol-2-yl]-3,3-dimethylbutyronitrile as starting material, the title compound was obtained as a white solid, m.p.: 131°-143° C.

EXAMPLE 148

5-[3-[1-(4-Chlorobenzyl)-4-methyl-6-(5-phenylpyridin-2-ylmethoxymethyl)-4,5-dihydro-1H-thiopyrano[2,3,4-c,d]indol-2-yl]-2,2-dimethylpropyl]-1H-tetrazole Step 1: 4-[1-(4-Chlorobenzyl)-4-methyl-6-trifluoromethanesulfonyloxy-4,5-dihydro-1H-thiopyrano[2,3,4-c,d]indol-2-yl]-3,3-dimethylbutyronitrile A solution of 4-[1-(4-chlorobenzyl)-4-methyl-6-hydroxy-4,5-dihydro-1H-thiopyrano[2,3,4-c,d]indol-2-yl]-3,3-dimethylbutyronitrile (1 g from Example 117, Step 3) in $CH_2Cl_2$ (25 mL) at 0° C. was added pyridine (0.38 mL) followed dropwise by trifluoromethanesulfonic anhydride (0.5 mL). The resulting reaction mixture was stirred for 30 minutes, diluted with $CH_2Cl_2$ (100 mL) washed successively with 1N HCl, a saturated aqueous solution of $NaHCO_3$, brine and dried over $MgSO_4$. Purification of the residue using flash chromatography (hexane:EtOAc 3:1) gave the title compound.

Step 2: 4-[1-(4-Chlorobenzyl)-4-methyl-6-carbomethoxy-4,5-dihydro-1H-thiopyrano[2,3,4-c,d]indol-2-yl]-3,3-dimethylbutyronitrile A solution of the triflate ester from Step 1 (1.2 g) was dissolved in DMSO (12 mL) and MeOH (9 mL) then $Et_3N$ (0.66 mL) was added followed by diphenylphosphinoethane (2.6 g) and $Pd(OAc)_2$ (1.5 g). Carbon monoxide was bubbled through the reaction mixture for 5 minutes then heated at 70°-80° C. while an atmosphere of CO was maintained for two days. The heterogenous reaction mixture was filtered through celite and washed with EtOAc. After removal of the solvent, purification by flash chromatography (hexane:EtOAc 4:1) gave the title compound.

Step 3: 4-[1-(4-Chlorobenzyl)-4-methyl-6-hydroxymethyl-4,5-dihydro-1H-thiopyrano[2,3,4-c,d]indol-2-yl]-3,3-dimethylbutyronitrile The ester from Step 2 (890 mg) was dissolved in dry THF (20 mL) cooled to 0° C. then $LiBH_4$ (500 mg) was added. The resulting mixture was stirred at r.t. for 16 hours, then poured carefully to 1N HCl and extracted with EtOAc (3×50 mL). The combined organic phase was successively washed with a saturated aqueous solution of NaHCO$_3$, brine and dried over MgSO$_4$. Evaporation of the solvent gave the title compound, which was used as such for the next step.

Step 4: 5-[3-[1-(4-Chlorobenzyl)-4-methyl-6-(5-phenylpyridin-2-ylmethoxymethyl)-4,5-dihydro-1-H-thiopyrano[2,3,4-c,d]indol-2-yl]-2,2-dimethylpropyl]-1H-tetrazole Following the procedure described in Example 1, Method A, Step 6 and Example 28, but substituting the alcohol from Step 3 for methyl 3-[1-(4-chlorobenzyl)-4-methyl-6-(5-phenylpyridin-2-ylmethoxy)-4,5-dihydro-1H-thiopyrano[2,3,4-c,d]indol-2,2-dimethylpropanoate as starting material, the title compound was obtained as a solid, m.p.: 100°-105° C. (dec).

EXAMPLE 149

5-[3-[1-(4-Chlorobenzyl)-4-methyl-6-(5-phenylpyridin-2-ylethyl)-4,5-dihydro-1H-thiopyrano[2,3,4-c,d]indol-2-yl]-2,2-dimethylpropyl]-1H-tetrazole Step 1: 4-[1-(4-Chlorobenzyl)-4-methyl-6-carboxaldehyde-4,5-dihydro-1H-thiopyrano[2,3,4-c,d]indol-2-yl]-3,3-dimethylbutyronitrile The primary alcohol from Example 148, Step 3 (186 mg) was dissolved in CH$_2$Cl$_2$ (5 mL) and MnO$_2$ (368 mg) was added at once. The reaction mixture was heated to 40° C. for 16 hours, then filtered through celite and the celite washed with EtOAc. After removal of the solvent the title compound was obtained and used as such for the next step.

Step 2: 5-[3-[1-(4-Chlorobenzyl)-4-methyl-6-(5-phenylpyridin-2-ylethyl)-4,5-dihydro-1-H-thiopyrano[2,3,4-c,d]indol-2-yl]-2,2-dimethylpropyl]-1H-tetrazole Following the procedure described in Example 117, Step 6 and 7 and Example 28 but substituting the aldehyde from Step 1 for 4-[1-(4-chlorobenzyl)-4-methyl-6-(formylmethoxy)-4,5-dihydro-1-H-thiopyrano [2,3,4-c,d]indol-2yl]-3,3-dimethylbutyronitrile as starting material, the title compound was obtained as a solid, m.p.: 188°-190° C.

What is claimed is:

1. A compound of the formula:

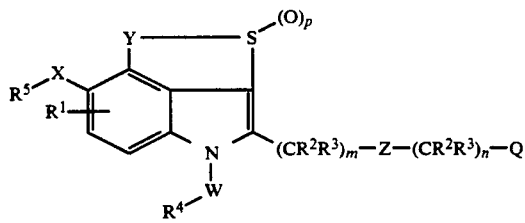

wherein:

$R^1$ is H, lower alkyl, cycloalkyl, lower alkoxy, perhalo lower alkenyl, CN, NO$_2$, CF$_3$, N$_3$, N(R$^6$)$_2$, NR$^6$COR$^7$, NR$^6$CON(R$^6$)$_2$, OR$^6$, SR$^8$, S(O)R$^8$, S(O)$_2$R$^8$, S(O)$_2$N(R$^6$)$_2$, COR$^7$, CON(R$^6$)$_2$, CO$_2$R$^9$, or halogen;

$R^2$ is H, lower alkyl, hydroxy, or lower alkoxy, or two $R^2$ groups on adjacent carbon atoms may be a bond;

$R^3$ is H or lower alkyl;

$R^2$ and $R^3$ on the same carbon atom may be a double-bonded oxygen (=O);

$R^4$ is H, [aryl(R$^{10}$)$_2$]$_t$, lower alkyl, alkyl, cycloalkyl, lower alkenyl, phenyl lower alkenyl, perhalophenyl, or substituted lower alkyl wherein the substituted is [aryl(R$^{10}$)$_2$]$_t$, phenoxy, or N-morpholino;

$R^5$ is alkyl, cycloalkyl, aryl(R$^{10}$)$_2$, CONR$^6$R$^{11}$, substituted lower alkyl wherein the substitutent is [aryl(R$^{10}$)$_2$]$_t$, or substituted tetrahydropyridyl wherein the substituent is phenyl or lower alkyl;

$R^6$ is H or lower alkyl, or two $R^6$ groups attached to the same nitrogen may form a saturated ring of 5 or 6 members, optionally containing a second heteroatom chosen from O, S, or NR$^2$;

$R^7$ is H, lower alkyl, phenyl, p-tolyl, or CF$_3$;

$R^8$ is lower alkyl, phenyl, p-tolyl, or CF$_3$;

$R^9$ is H, lower alkyl, or benzyl;

$R^{10}$ is H, lower alkyl, cycloalkyl, lower alkoxy, benzyl, benzyloxy, perhalo lower alkenyl, CN, NO$_2$, CF$_3$, N$_3$, N(R$^6$)$_2$, NR$^6$COR$^7$, NR$^6$CON(R$^6$)$_2$, OR$^6$, SR$^8$, S(O)R$^8$, S(O)$_2$R$^8$, S(O)$_2$N(R$^6$)$_2$, COR$^7$, CON(R$^6$)$_2$, CO$_2$R$^9$, halogen hydroxy- or lower alkoxy-tetrahydropyranyl, or 1-hydroxy- or 1-lower alkoxy-1-thiazol-2,4, or 5-yl lower alkyl;

$R^{11}$ is $R^{10}$-phenyl lower alkyl;

$R^{12}$ is H or lower alkyl;

$R^{13}$ is H or lower alkyl;

$R^{14}$ is lower alkyl, $R^{10}$-phenyl, CF$_3$, or N(R$^6$)$_2$;

$R^{15}$ is CO$_2$H, N(R$^6$)$_2$, or NHCOR$^7$;

$R^{16}$ is —(CH$_2$)$_s$—C(R$^{17}$)$_2$—(CH$_2$)$_s$—R$^{18}$ or —CH$_2$CON(R$^{20}$)$_2$;

$R^{17}$ is H or lower alkyl;

$R^{18}$ is a) 2,5-dioxo-1-pyrrolidinyl, (3-pyridinylcarbonyl)amino, 1,3-dihydro-1,3,-dioxo-2H-isoindol-2-yl, 1,3-dihydro-2H-isoindol-2-yl, 2,4-imidazolinedion-1-yl, 2,6-piperidinedion-1-yl, 2-imidazolyl, 2-oxo-1,3,-dioxolen-4-yl, piperidin-1-yl, morpholin-1-yl, or piperazin-1-yl, or b) the radical V-R$^{19}$;

$R^{19}$ contains up to 20 carbon atoms and is (1) an alkyl group or (2) an alkyl carbonyl group of an organic acyclic or monocyclic carboxylic acid containing not more than 1 heteroatom in the ring;

$R^{20}$ is H or lower alkyl or 2 $R^{20}$ groups attached to the same nitrogen may form a saturated ring of 5 or 6 members, optionally containing a second heteroatom chosen from O, S, or NR$^2$;

$R^{21}$ is H, lower alkyl, lower alkylcarbonyl, or lower alkylsulfonyl;

Q is CO$_2$R$^9$, CN$_4$H, —OH, —CH$_2$OH, —CHO, —CON(R$^6$)$_2$, —CON(OH)R$^6$, —CONHS(O)$_2$R$^{14}$, —COCN$_4$H, —CONR$^6$(CH$_2$)$_r$R$^{15}$, —N(R$^6$)$_2$, —NHCOR$^7$, —NHS(O)$_2$R$^{14}$, —NHCOCO$_2$R$^9$, —CO$_2$R$^{16}$, —CONHCN, or —CONHCN$_4$H;

U is CH$_2$, O, or S;

V is O, S, or NR$^9$;

W is CH$_2$ or CO, or S(O)$_2$ when $R^4$ is not H;

X is (CH$_2$)$_q$U—, —U(CH$_2$)$_q$—, —CH=CH—, or —CH$_2$OCH$_2$—;

Y is —CH$_2$C(R$^{12}$)$_2$—, —CH=CR$^{13}$—, —CH$_2$=CHCH$_2$—, or —(CH$_2$)$_3$—;

Z is a bond, O, S, NR$^{21}$, or CONR$^9$;

m is 0 to 3;

n is 1 to 3 when Z is O, S, NR$^{21}$, or CONR$^9$;

n is 0 to 3 when Z is a bond;

p is 0 to 2;

q is 0 to 3;

r is 1 to 3;
s is 0 or 1;
t is 1 or 2;
aryl is phenyl, pyridinyl, quinolinyl, isoquinolinyl, thiazolyl, thienyl, oxazolyl, pyrimidinyl, pyrazinyl, furopyridinyl, naphthyl, 1,8-naphthyridinyl, or methylenedioxyphenyl or the N-oxides thereof;
or a pharmaceutically acceptable salt thereof.

2. A compound of claim 1 of the formula:

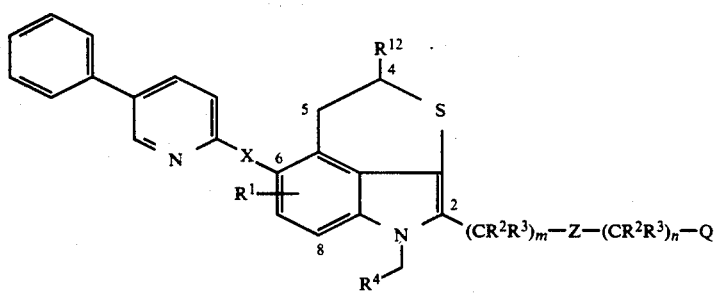

wherein:
$R^1$ is H, lower alkyl, or halogen;
$R^4$ is alkyl, cycloalkyl, [aryl($R^{10}$)$_2$]$_t$, or substituted lower alkyl wherein the substitutent is [aryl($R^{10}$)$_2$]$_t$;
$R^{10}$ is H or lower alkyl;
Q is —CO$_2$H, CN$_4$H, or —CONHS(O)$_2R^{14}$; and q is 1.

3. A compound of claim 1 of formula Ib

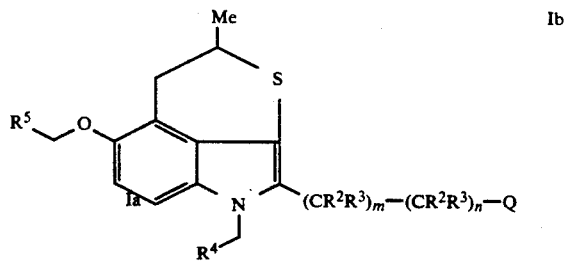

wherein the substituents are as follows:

| | $R^4$ | $R^5$ | $(CR^2R^3)_m$-$(CR^2R^3)_n$ | Q |
|---|---|---|---|---|
| 1 | 4-ClC$_6$H$_4$ | 5-C$_6$H$_5$-2-C$_5$H$_3$N$^+$ | CH$_2$C(Me)$_2$ | CO$_2$H |
| 2 | n-Pr | 5-C$_6$H$_5$-2-C$_5$H$_3$N | CH$_2$C(Me)$_2$ | CO$_2$H |
| 3 | H | 5-C$_6$H$_5$-2-C$_5$H$_3$N | CH$_2$C(Me)$_2$ | CO$_2$H |
| 4 | C$_6$H$_5$ | 5-C$_6$H$_5$-2-C$_5$H$_3$N | CH$_2$C(Me)$_2$ | CO$_2$H |
| 5 | 4-MeOC$_6$H$_4$ | 5-C$_6$H$_5$-2-C$_5$H$_3$N | CH$_2$C(Me)$_2$ | CO$_2$H |
| 6 | 3-MeOC$_6$H$_4$ | 5-C$_6$H$_5$-2-C$_5$H$_3$N | CH$_2$C(Me)$_2$ | CO$_2$H |
| 7 | 4-MeS(O)$_2$C$_6$H$_4$ | 5-C$_6$H$_5$-2-C$_5$H$_3$N | CH$_2$C(Me)$_2$ | CO$_2$H |
| 8 | 4-MeSC$_6$H$_4$ | 5-C$_6$H$_5$-2-C$_5$H$_3$N | CH$_2$C(Me)$_2$ | CO$_2$H |
| 9 | 4-C$_6$H$_5$C$_6$H$_4$ | 5-C$_6$H$_5$-2-C$_5$H$_3$N | CH$_2$C(Me)$_2$ | CO$_2$H |
| 10 | 4-NC-C$_6$H$_4$ | 5-C$_6$H$_5$-2-C$_5$H$_3$N | CH$_2$C(Me)$_2$ | CO$_2$H |
| 11 | C$_6$H$_5$(CH$_2$)$_2$ | 5-C$_6$H$_5$-2-C$_5$H$_3$N | CH$_2$C(Me)$_2$ | CO$_2$H |
| 12* | 3,4-CH$_2$O$_2$C$_6$H$_3$ | 5-C$_6$H$_5$-2-C$_5$H$_3$N | CH$_2$C(Me)$_2$ | CO$_2$H |
| 13 | C$_6$H$_5$OCH$_2$ | 5-C$_6$H$_5$-2-C$_5$H$_3$N | CH$_2$C(Me)$_2$ | CO$_2$H |
| 14 | C$_6$H$_5$CH=CH (E-isomer) | 5-C$_6$H$_5$-2-C$_5$H$_3$N | CH$_2$C(Me)$_2$ | CO$_2$H |
| 15 | c-Hex | 5-C$_6$H$_5$-2-C$_5$H$_3$N | CH$_2$C(Me)$_2$ | CO$_2$H |
| 16 | CH$_2$=CH | 5-C$_6$H$_5$-2-C$_5$H$_3$N | CH$_2$C(Me)$_2$ | CO$_2$H |
| 17 | Me(CH$_2$)$_8$ | 5-C$_6$H$_5$-2-C$_5$H$_3$N | CH$_2$C(Me)$_2$ | CO$_2$H |
| 18 | C$_6$H$_5$CH$_2$ | 5-C$_6$H$_5$-2-C$_5$H$_3$N | CH$_2$C(Me)$_2$ | CO$_2$H |
| 19 | c-Hex-(CH$_2$)$_2$ | 5-C$_6$H$_5$-2-C$_5$H$_3$N | CH$_2$C(Me)$_2$ | CO$_2$H |
| 20* | 2-C$_4$H$_3$S | 5-C$_6$H$_5$-2-C$_5$H$_3$N | CH$_2$C(Me)$_2$ | CO$_2$H |
| 21* | 2-C$_5$H$_4$N | 5-C$_6$H$_5$-2-C$_5$H$_3$N | CH$_2$C(Me)$_2$ | CO$_2$H |
| 22* | 2-C$_9$H$_6$N | 5-C$_6$H$_5$-2-C$_5$H$_3$N | CH$_2$C(Me)$_2$ | CO$_2$H |
| 23 | 5-C$_6$H$_5$-2-C$_5$H$_3$N | 5-C$_6$H$_5$-2-C$_5$H$_3$N | CH$_2$C(Me)$_2$ | CO$_2$H |
| 24* | 1-Ada-CH$_2$ | 5-C$_6$H$_5$-2-C$_5$H$_3$N | CH$_2$C(Me)$_2$ | CO$_2$H |
| 25 | 3-CF$_3$C$_6$H$_4$ | 5-C$_6$H$_5$-2-C$_5$H$_3$N | CH$_2$C(Me)$_2$CH$_2$ | CO$_2$H |
| 26 | 3-CF$_3$C$_6$H$_4$ | 5-C$_6$H$_5$-2-C$_5$H$_3$N | CH$_2$C(Me)$_2$CH$_2$ | CN$_4$H$^+$ |
| 27 | 4-ClC$_6$H$_4$ | 5-C$_6$H$_5$-2-C$_5$H$_3$N | CH$_2$C(Me)$_2$CH$_2$ | CO$_2$H |
| 28 | 4-ClC$_6$H$_4$ | 5-C$_6$H$_5$-2-C$_5$H$_3$N | CH$_2$C(Me)$_2$CH$_2$ | CN$_4$H |
| 29 | C$_6$H$_5$ | 5-C$_6$H$_5$-2-C$_5$H$_3$N | CH$_2$C(Me)$_2$CH$_2$ | CO$_2$H |
| 30 | C$_6$H$_5$ | 5-C$_6$H$_5$-2-C$_5$H$_3$N | CH$_2$C(Me)$_2$CH$_2$ | CN$_4$H |
| 31 | 3-MeOC$_6$H$_4$ | 5-C$_6$H$_5$-2-C$_5$H$_3$N | CH$_2$C(Me)$_2$CH$_2$ | CO$_2$H |
| 32 | 3-MeOC$_6$H$_4$ | 5-C$_6$H$_5$-2-C$_5$H$_3$N | CH$_2$C(Me)$_2$CH$_2$ | CN$_4$H |
| 33 | 4-FC$_6$H$_4$ | 5-C$_6$H$_5$-2-C$_5$H$_3$N | CH$_2$C(Me)$_2$CH$_2$ | CO$_2$H |
| 34 | 4-FC$_6$H$_4$ | 5-C$_6$H$_5$-2-C$_5$H$_3$N | CH$_2$C(Me)$_2$CH$_2$ | CN$_4$H |
| 35 | 3-ClC$_6$H$_4$ | 5-C$_6$H$_5$-2-C$_5$H$_3$N | CH$_2$C(Me)$_2$CH$_2$ | CO$_2$H |
| 36 | 3-ClC$_6$H$_4$ | 5-C$_6$H$_5$-2-C$_5$H$_3$N | CH$_2$C(Me)$_2$CH$_2$ | CN$_4$H |
| 37 | 3-FC$_6$H$_4$ | 5-C$_6$H$_5$-2-C$_5$H$_3$N | CH$_2$C(Me)$_2$CH$_2$ | CO$_2$H |
| 38 | 3-FC$_6$H$_4$ | 5-C$_6$H$_5$-2-C$_5$H$_3$N | CH$_2$C(Me)$_2$CH$_2$ | CN$_4$H |
| 39* | 2-C$_5$H$_4$N | 5-C$_6$H$_5$-2-C$_5$H$_3$N | CH$_2$C(Me)$_2$CH$_2$ | CO$_2$H |
| 40* | 2-C$_5$H$_4$N | 5-C$_6$H$_5$-2-C$_5$H$_3$N | CH$_2$C(Me)$_2$CH$_2$ | CN$_4$H |
| 41 | C$_6$H$_5$(CH$_2$)$_2$ | 5-C$_6$H$_5$-2-C$_5$H$_3$N | CH$_2$C(Me)$_2$CH$_2$ | CO$_2$H |
| 42 | C$_6$H$_5$(CH$_2$)$_2$ | 5-C$_6$H$_5$-2-C$_5$H$_3$N | CH$_2$C(Me)$_2$CH$_2$ | CN$_4$H |
| 43 | c-Hex | 5-C$_6$H$_5$-2-C$_5$H$_3$N | CH$_2$C(Me)$_2$CH$_2$ | CO$_2$H |
| 44 | c-Hex | 5-C$_6$H$_5$-2-C$_5$H$_3$N | CH$_2$C(Me)$_2$CH$_2$ | CN$_4$H |

-continued

|     | R⁴ | R⁵ | $(CR^2R^3)_m$-$(CR^2R^3)_n$ | Q |
|---|---|---|---|---|
| 45 | 4-ClC₆H₄ | 5-C₆H₅-2-C₅H₃N | CH₂C(Me)₂CH₂ | CONHS(O)₂Me |
| 46 | 4-ClC₆H₄ | 5-C₆H₅-2-C₅H₃N | CH₂C(Me)₂CH₂ | CONHS(O)₂C₆H₅ |
| 47 | 4-ClC₆H₄ | 5-C₆H₅-2-C₅H₃N | CH₂C(Me)₂CH₂ | CONHS(O)₂CF₃ |
| 48 | 4-ClC₆H₄ | 5-C₆H₅-2-C₅H₃N | CH₂C(Me)₂(CH₂)₂ | CO₂H |
| 49 | 4-ClC₆H₄ | 5-C₆H₅-2-C₅H₃N | CH₂C(Me)₂(CH₂)₂ | CN₄H |
| 50 | 4-ClC₆H₄ | 5-C₆H₅-2-C₅H₃N | — | CO₂H |
| 51 | 4-ClC₆H₄ | 5-C₆H₅-2-C₅H₃N | CH₂ | CO₂H |
| 52 | 4-ClC₆H₄ | 5-C₆H₅-2-C₅H₃N | (CH₂)₂ | CO₂H |
| 53 | 4-ClC₆H₄ | 5-C₆H₅-2-C₅H₃N | (CH₂)₂ | CN₄H |
| 54 | 4-ClC₆H₄ | 5-C₆H₅-2-C₅H₃N | (CH₂)₂C(Me)₂ | CO₂H |
| 55 | 4-ClC₆H₄ | 5-C₆H₅-2-C₅H₃N | CH₂C(Me)₂ | CON(OH)Me |
| 56 | 4-ClC₆H₄ | 5-C₆H₅-2-C₅H₃N | CH₂C(Me)₂ | CONH₂ |
| 57 | 4-ClC₆H₄ | 5-C₆H₅-2-C₅H₃N | CH₂C(Me)₂ | CONHMe |
| 58 | 4-ClC₆H₄ | 5-C₆H₅-2-C₅H₃N | CH₂C(Me)₂ | CON(Me)₂ |
| 59 | 4-ClC₆H₄ | 5-C₆H₅-2-C₅H₃N | CH₂C(Me)₂ | CONHCH₂CO₂H |
| 60 | 4-ClC₆H₄ | 5-C₆H₅-2-C₅H₃N | CH₂C(Me)₂ | CONH(CH₂)₃NHAc |
| 61 | 4-ClC₆H₄ | 5-C₆H₅-2-C₅H₃N | CH₂C(Me)₂ | CONH(CH₂)₃NH₂ |
| 62 | 4-ClC₆H₄ | 5-C₆H₅-2-C₅H₃N | CH₂C(Me)₂ | CONHn-Bu |
| 63 | 4-ClC₆H₄ | 5-C₆H₅-2-C₅H₃N | CH₂C(Me)₂ | NH₂ |
| 64 | 4-ClC₆H₄ | 5-C₆H₅-2-C₅H₃N | CH₂C(Me)₂ | NHAc |
| 65 | 4-ClC₆H₄ | 5-C₆H₅-2-C₅H₃N | CH₂C(Me)₂ | NHCOCO₂Et |
| 66 | 4-ClC₆H₄ | 5-C₆H₅-2-C₅H₃N | CH₂C(Me)₂ | NHCOCO₂H |
| 67 | 4-ClC₆H₄ | 5-C₆H₅-2-C₅H₃N | CH₂C(Me)₂ | NHS(O)₂C₆H₅ |
| 89 (+)-isomer | 4-ClC₆H₄ | 5-C₆H₅-2-C₅H₃N | CH₂C(Me)₂ | CO₂H |
| 90 (−)-isomer | 4-ClC₆H₄ | 5-C₆H₅-2-C₅H₃N | CH₂C(Me)₂ | CO₂H |
| 94* | 4-ClC₆H₄ | 5-C₆H₅-2-C₅H₃N(O) | CH₂C(Me)₂ | CO₂H |
| 95* | 4-ClC₆H₄ | 5-C₆H₅-2-C₅H₃N(O) | CH₂C(Me)₂CH₂ | CN₄H |
| 96* | 4-ClC₆H₄ | 2-C₉H₆N | CH₂C(Me)₂ | CO₂H |
| 97* | 4-ClC₆H₄ | 2-C₉H₆N(O) | CH₂C(Me)₂ | CO₂H |
| 98 | 4-ClC₆H₄ | 4-C₆H₅CH₄ | CH₂C(Me)₂ | CO₂H |
| 99 | 4-ClC₆H₄ | 6-C₆H₅-2-C₅H₃N | CH₂C(Me)₂ | CO₂H |
| 100 | 4-ClC₆H₄ | 4-C₆H₅-2-C₅H₃N | CH₂C(Me)₂ | CO₂H |
| 101 | 4-ClC₆H₄ | 2-C₆H₅-3-C₅H₃N | CH₂C(Me)₂ | CO₂H |
| 102 | 4-ClC₆H₄ | 2-C₅H₄N⁺ | CH₂C(Me)₂ | CO₂H |
| 103 | 4-ClC₆H₄ | 3-C₅H₄N | CH₂C(Me)₂ | CO₂H |
| 104 | 4-ClC₆H₄ | 4-C₅H₄N | CH₂C(Me)₂ | CO₂H |
| 105 | 4-ClC₆H₄ | 2-C₆H₅-4-C₅H₃N | CH₂C(Me)₂ | CO₂H |
| 106 | 4-ClC₆H₄ | 5-MeO-2-C₅H₃N | CH₂C(Me)₂ | CO₂H |
| 107 | 4-ClC₆H₄ | 5-H₂NCO-2-C₅H₃N | CH₂C(Me)₂ | CO₂H |
| 108 | 4-ClC₆H₄ | 5-(Me)₂NCO-2-C₅H₃N | CH₂C(Me)₂ | CO₂H |
| 109 | 4-ClC₆H₄ | 5-C₆H₅CH₂O-2-C₅H₃N | CH₂C(Me)₂ | CO₂H |
| 110 | 4-ClC₆H₄ | 5-NC-2-C₅H₃N | CH₂C(Me)₂ | CO₂H |
| 111 | 4-ClC₆H₄ | 5-n-Bu-2-C₅H₃N | CH₂C(Me)₂ | CO₂H |
| 112 | 4-ClC₆H₄ | 6-Cl-2-C₅H₃N | CH₂C(Me)₂ | CO₂H |
| 113 | 4-ClC₆H₄ | 6-Cl-5-C₆H₅-2-C₅H₂N | CH₂C(Me)₂ | CO₂H |
| 114 | 4-ClC₆H₄ | 4-Cl-5-C₆H₅-2-C₅H₂N | CH₂C(Me)₂ | CO₂H |
| 115 | 4-ClC₆H₄ | 4-MeO-5-C₆H₅-2-C₅H₂N | CH₂C(Me)₂ | CO₂H |
| 116 | 4-ClC₆H₄ | 5-C₆H₅CH₂-2-C₅H₃N | CH₂C(Me)₂ | CO₂H |
| 117 | 4-ClC₆H₄ | 5-C₆H₅-2-C₅H₃N(CH₂)₂ | CH₂C(Me)₂CH₂ | CN₄H |
| 118* | 4-ClC₆H₄ | 3-C₉H₆N | CH₂C(Me)₂ | CO₂H |
| 119* | 4-ClC₆H₄ | 4-C₉H₆N | CH₂C(Me)₂ | CO₂H |
| 120* | 4-ClC₆H₄ | 2-C₈H₅N₂ | CH₂C(Me)₂ | CO₂H |
| 121 | 4-ClC₆H₄ | 5-(4-ClC₆H₄)-2-C₅H₃N | CH₂C(Me)₂ | CN₄H |
| 122 | 4-ClC₆H₄ | 4-(2-C₅H₄N)C₆H₄ | CH₂C(Me)₂ | CO₂H |
| 123* | 4-ClC₆H₄ | 2-C₄H₃S | CH₂C(Me)₂ | CO₂H |
| 124 | 4-ClC₆H₄ | C₆H₅ | CH₂C(Me)₂ | CO₂H |
| 125 | 4-ClC₆H₄ | C₆H₅(CH₂)₂ | CH₂C(Me)₂ | CO₂H |
| 126* | 4-ClC₆H₄ | 3,5-Me₂-4-C₃NO | CH₂C(Me)₂ | CO₂H |
| 127* | 4-ClC₆H₄ | 2-(4-ClC₆H₄)-4-C₃NS | CH₂C(Me)₂ | CO₂H |
| 128* | 4-ClC₆H₄ | 1-Me-5-C₆H₅-2-C₅H₆N | CH₂C(Me)₂ | CO₂H |
| 129 | 4-ClC₆H₄ | c-Hex | CH₂C(Me)₂ | CO₂H |
| 130 | 4-ClC₆H₄ | C₆H₅(CH₂)₂N(Me)CO | CH₂C(Me)₂ | CO₂H |
| 131* | 4-ClC₆H₄ | 2-C₁₀H₇ | CH₂C(Me)₂ | CO₂H |
| 132* | 4-ClC₆H₄ | 2-C₁₀H₇ | CH₂C(Me)₂CH₂ | CN₄H |
| 133* | 4-ClC₆H₄ | 5-C₆H₅-2-C₃HNO | CH₂C(Me)₂CH₂ | CN₄H |
| 134 | 4-ClC₆H₄ | 5-(4-MeOC₆H₄)-2-C₅H₃N | CH₂C(Me)₂CH₂ | CN₄H |
| 135* | 4-ClC₆H₄ | 5-(1-C₁₀H₇)-2-C₅H₃N | CH₂C(Me)₂CH₂ | CN₄H |
| 136* | 4-ClC₆H₄ | 5-C₆H₅-2-C₄H₂N₂ | CH₂C(Me)₂CH₂ | CN₄H |
| 137* | 4-ClC₆H₄ | 5-C₆H₅-2-C₄H₂N₂ | CH₂C(Me)₂CH₂ | CN₄H |
| 138* | 4-ClC₆H₄ | 2-C₆H₅-5-C₇H₃NO | CH₂C(Me)₂CH₂ | CN₄H |
| 150* | 4-ClC₆H₄ | 3-[C₃H₃NS-C₃H₅(MeO)]-C₆H₄ | CH₂C(Me)₂ | CO₂H |
| 151* | 4-ClC₆H₄ | 1-CO₂Me-2-C₁₀H₆ | CH₂C(Me)₂ | CO₂H |
| 152 | 4-ClC₆H₄ | 3-MeO-C₆H₄ | CH₂C(Me)₂ | CO₂H |
| 153 | 3-CF₃C₆H₄ | 5-C₆H₅-2-C₅H₃N | CH₂C(Me)₂CH₂ | CO₂H |
| 154 | 3-CF₃C₆H₄ | 5-C₆H₅-2-C₅H₃N | CH₂C(Me)₂CH₂ | CN₄H |
| 155 | 3-ClC₆H₄ | 5-C₆H₅-2-C₅H₃N | CH₂C(Me)₂CH₂ | CONHS(O)₂Me |
| 156 | 4-ClC₆H₄ | 5-C₆H₅-2-C₅H₃N | CH₂C(Me)₂CH₂ | CONH₂ |
| 157 | 2-ClC₆H₄ | 5-C₆H₅-2-C₅H₃N | CH₂C(Me)₂CH₂ | CN₄H |
| 158 | 2-ClC₆H₄ | 5-C₆H₅-2-C₅H₃N | CH₂C(Me)₂CH₂ | CO₂H |

-continued

| | $R^4$ | $R^5$ | $(CR^2R^3)_m$-$(CR^2R^3)_n$ | Q |
|---|---|---|---|---|
| 159 | 3,4-Cl$_2$C$_6$H$_3$ | 5-C$_6$H$_5$-2-C$_5$H$_3$N | CH$_2$C(Me)$_2$CH$_2$ | CN$_4$H |
| 160 | 3,4-Cl$_2$C$_6$H$_3$ | 5-C$_6$H$_5$-2-C$_5$H$_3$N | CH$_2$C(Me)$_2$CH$_2$ | CO$_2$H |
| 161 | 4-ClC$_6$H$_4$ | 5-C$_6$H$_5$-2-C$_5$H$_3$N | CH$_2$C(Me)$_2$CH$_2$ | CONHCN$_4$H |
| 162 | 4-ClC$_6$H$_4$ | 5-C$_6$H$_5$-2-C$_5$H$_3$N | CH$_2$C(Me)$_2$CH$_2$ | CON(OH)Me |
| 163 | 4-ClC$_6$H$_4$ | 5-C$_6$H$_5$-2-C$_5$H$_3$N | CH$_2$C(Me)$_2$CH$_2$ | CONHCN |
| 164* | 2-C$_{10}$H$_7$ | 5-C$_6$H$_5$-2-C$_5$H$_3$N | CH$_2$C(Me)$_2$CH$_2$ | CO$_2$H |
| 165* | 3-(4-MeO-4-C$_5$H$_8$O)-C$_6$H$_4$ | 5-C$_6$H$_5$-2-C$_5$H$_3$N | CH$_2$C(Me)$_2$CH$_2$ | CO$_2$H |
| 166 | C$_6$F$_5$ | 5-C$_6$H$_5$-2-C$_5$H$_3$N | CH$_2$C(Me)$_2$CH$_2$ | CO$_2$H |
| 167* | 3-C$_4$H$_8$NO-C$_6$H$_4$ | 5-C$_6$H$_5$-2-C$_5$H$_3$N | CH$_2$C(Me)$_2$CH$_2$ | CO$_2$H |
| 168* | 4-(4-HO-4-C$_5$H$_8$O)-C$_6$H$_4$ | 5-C$_6$H$_5$-2-C$_5$H$_3$N | CH$_2$C(Me)$_2$CH$_2$ | CO$_2$H |
| 169* | 4-MeO-3-(4-HO-4-C$_5$H$_8$O)-C$_6$H$_4$ | 5-C$_6$H$_5$-2-C$_5$H$_3$N | CH$_2$C(Me)$_2$CH$_2$ | CO$_2$H |
| 170* | 4-(4-EtO-4-C$_5$H$_8$O)-C$_6$H$_4$ | 5-C$_6$H$_5$-2-C$_5$H$_3$N | CH$_2$C(Me)$_2$CH$_2$ | CO$_2$H |
| 171* | 4-(4-EtO-4-C$_5$H$_8$O)-C$_6$H$_4$ | 5-C$_6$H$_5$-2-C$_5$H$_3$N | CH$_2$C(Me)$_2$CH$_2$ | CO$_2$H |
| 172 | 4-ClC$_6$H$_4$ | 5-C$_6$H$_5$-2-C$_5$H$_3$N | (CH$_2$)$_2$CHMe | CO$_2$H |

4. A compound of claim 1 of formula Ic

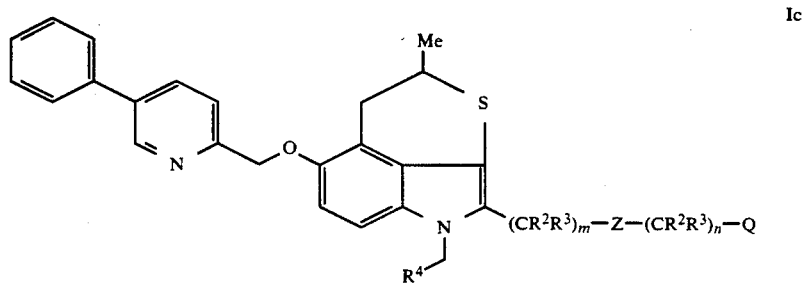

Ic wherein the substituents are as follows:

| | $R^4$ | $(CR^2R^3)_m$ | Z | $(CR^2R^3)_n$ | Q |
|---|---|---|---|---|---|
| 68 | 4-ClC$_6$H$_4$ | CH$_2$ | O | CH$_2$ | CO$_2$H |
| 69 | 4-ClC$_6$H$_4$ | CH$_2$ | O | CH(Me) | CO$_2$H |
| 70 | 4-ClC$_2$H$_4$ | CH$_2$ | S | CH$_2$ | CO$_2$H |
| 71 | 4-ClC$_6$H$_4$ | CH$_2$ | S | (CH$_2$)$_2$ | CO$_2$H |
| 72 | 4-ClC$_6$H$_4$ | CH$_2$ | S | CH$_2$CH(Et) | CO$_2$H |
| 73 | 4-ClC$_6$H$_4$ | CH$_2$ | S | CH$_2$CH(Et) (S) isomer | CO$_2$H |
| 74 | 4-ClC$_6$H$_4$ | CH$_2$ | S | CH$_2$CH(Et) (R) isomer | CO$_2$H |
| 75 | 4-ClC$_6$H$_4$ | CH$_2$ | S | CH$_2$CH(Me) | CO$_2$H |
| 76 | 4-ClC$_6$H$_4$ | CH$_2$ | S | CH$_2$CH(OMe) | CO$_2$H |
| 77 | 4-ClC$_6$H$_4$ | CH$_2$ | S | C(Me)$_2$CH$_2$ | CO$_2$H |
| 78 | 4-ClC$_6$H$_4$ | CH$_2$ | S | CH$_2$C(Me)$_2$ | CO$_2$H |
| 79 | 4-ClC$_6$H$_4$ | CH$_2$ | O | (CH$_2$)$_2$ | CN$_4$H |
| 80 | 4-ClC$_6$H$_4$ | (CH$_2$)$_2$ | O | CH$_2$ | CO$_2$H |
| 81 | 4-ClC$_6$H$_4$ | (CH$_2$)$_2$ | O | CH$_2$ | CN$_4$H |
| 82 | 4-ClC$_6$H$_4$ | (CH$_2$)$_2$ | O | CH(Me) | CO$_2$H |
| 83 | 4-ClC$_6$H$_4$ | (CH$_2$)$_2$ | O | CH(Me) | CN$_4$H |
| 84 | 4-ClC$_6$H$_4$ | (CH$_2$)$_2$ | S | CH(Me) | CO$_2$H |
| 85 | 4-ClC$_6$H$_4$ | (CH$_2$)$_2$ | O | (CH$_2$)$_2$ | CO$_2$H |
| 86 | 4-ClC$_6$H$_4$ | (CH$_2$)$_2$ | O | (CH$_2$)$_2$ | CN$_4$H |
| 87 | C$_6$H$_5$ | (CH$_2$)$_2$ | O | CH(Me) | CO$_2$H |
| 173 | 3-ClC$_6$H$_4$ | (CH$_2$)$_2$ | O | CH(Me) | CO$_2$H |
| 174 | 3-ClC$_6$H$_4$ | (CH$_2$)$_2$ | O | CH(Et) | CO$_2$H |
| 175 (racemic) | 4-ClC$_6$H$_4$ | (CH$_2$)$_2$ | O | CH(Et) | CO$_2$H |
| 176 (isomer 1) | 4-ClC$_6$H$_4$ | (CH$_2$)$_2$ | O | CH(Et) | CO$_2$H |
| 177 (isomer 2) | 4-ClC$_6$H$_4$ | (CH$_2$)$_2$ | O | CH(Et) | CO$_2$H |
| 178 (isomer 3) | 4-ClC$_6$H$_4$ | (CH$_2$)$_2$ | O | CH(Et) | CO$_2$H |
| 179 (isomer 4) | 4-ClC$_6$H$_4$ | (CH$_2$)$_2$ | O | CH(Et) | CO$_2$H |
| 180 | 4-ClC$_6$H$_4$ | (CH$_2$)$_2$ | O | C(Me)$_2$ | CO$_2$H |
| 181 | 4-ClC$_6$H$_4$ | (CH$_2$)$_2$ | O | CH(Me) | CONHS(O)$_2$Me |
| 182 (racemic) | 4-ClC$_6$H$_4$ | (CH$_2$)$_2$ | O | CH(Et) | CONHS(O)$_2$Me |
| 183 (isomer 1) | 4-ClC$_6$H$_4$ | (CH$_2$)$_2$ | O | CH(Et) | CONHS(O)$_2$Me |
| 184 (isomer 2) | 4-ClC$_6$H$_4$ | (CH$_2$)$_2$ | O | CH(Et) | CONHS(O)$_2$Me |

-continued

| | R⁴ | (CR²R³)ₘ | Z | (CR²R³)ₙ | Q |
|---|---|---|---|---|---|
| 185 | 4-ClC₆H₄ | (CH₂)₂ | O | CH(Et) | CONHS(O)₂Ph |
| 186 | 4-ClC₆H₄ | (CH₂)₂ | S | CH₂CH(Et) | CO₂H |
| 187 | 4-ClC₆H₄ | CH₂ | O | (CH₂)₂ | CO₂H |
| 188 | 4-ClC₆H₄ | CH₂ | O | CH(Me)CH₂ | CO₂H |
| 189 | 4-ClC₆H₂ | CH₂ | O | CH(Et)CH₂ | CO₂H |
| 190 | 4-ClC₆H₄ | (CH₂)₂ | O | CH(Me)CH₂ | CO₂H |
| 191 | 4-ClC₆H₄ | CH₂ | S | CH(Me)CH₂ | CO₂H |
| 192 | 4-ClC₆H₄ | CH₂ | S | CH₂CH(Et) | CONHS(O)₂Me |
| 193 | 4-ClC₆H₄ | CH₂ | NH | (CH₂)₂ | CO₂H |
| 194 | 4-ClC₆H₄ | (CH₂)₂ | NH | CH(Me) | CO₂H |
| 195 | 4-ClC₆H₄ | — | S | CH(Me)CH₂ | CO₂H |
| 196 | 4-ClC₆H₅ | — | CON(Me) | CH₂ | CO₂H |
| 197 | 4-ClC₆H₅ | CH₂ | CON(Me) | CH₂ | CO₂H |
| 198 | 4-ClC₆H₅ | CH₂ | CON(Me) | CH(Me) | CO₂H |
| 199 | 4-ClC₆H₅ | CH₂ | CON(Me) | CH[CH(Me)₂] | CO₂H |
| 200 | 4-ClC₆H₅ | CH₂ | CON(Me) | CH[CH₂CH(Me)₂] | CO₂H |
| 201 | 4-ClC₆H₅ | CH₂ | CON(Me) | CH(CH₂Ph) | CO₂H |
| 220 | 4-ClC₆H₅ | (CH₂)₂ | N(COMe) | CH(Me) | CO₂H |
| 221 | 4-ClC₆H₅ | (CH₂)₂ | N[S(O)₂Me] | CH(Me) | CO₂H |

5. A compound of claim 1 of formula Id

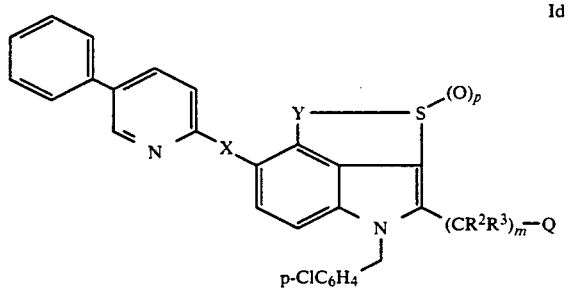

Id wherein the substituents are as follows:

6. A compound of claim 1 of formula Ie

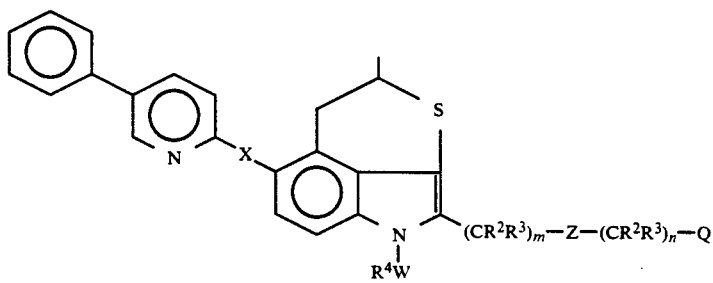

wherein the substituents are as follows:

| | p | X | Y | (CR²R³)ₘ | Q |
|---|---|---|---|---|---|
| 88 | 0 | CH₂O | CH₂C(Me)₂ | CH₂C(Me)₂ | CO₂H |
| 91 | 0 | CH₂O | (CH₂)₂ | CH₂C(Me)₂ | CO₂H |
| 92 | 0 | CH₂O | CH₂CH(Et) | CH₂C(Me)₂ | CO₂H |
| 93 | 0 | CH₂O | CH₂CH(n-Pr) | CH₂C(Me)₂ | CO₂H |
| 139 | 2 | CH₂O | CH₂CH(Me) | CH₂C(Me)₂ | CO₂H |
| 140 Mixture | 1 | CH₂O | CH₂CH(Me) | CH₂C(Me)₂ | CO₂H |
| 141 (R*,S*) | 1 | CH₂O | CH₂CH(Me) | CH₂C(Me)₂ | CO₂H |
| 142 (R*,R*) | 1 | CH₂O | CH₂CH(Me) | CH₂C(Me)₂ | CO₂H |
| 143 | 0 | CH₂O | CH=CHCH₂ | CH₂C(Me)₂ | CO₂H |
| 144 | 0 | CH₂O | (CH₂)₃ | CH₂C(Me)₂ | CO₂H |
| 145 | 0 | CH₂S | CH₂CH(Me) | CH₂C(Me)₂ | CO₂H |
| 146 | 0 | CH₂S | CH₂CH(Me) | CH₂C(Me)₂CH₂ | CO₂H |
| 147 | 0 | CH₂S | CH₂CH(Me) | CH₂C(Me)₂CH₂ | CN₄H |
| 148 | 0 | CH₂OCH₂ | CH₂CH(Me) | CH₂C(Me)₂CH₂ | CN₄H |
| 149 | 0 | (CH₂)₂ | CH₂CH(Me) | CH₂C(Me)₂CH₂ | CN₄H |
| 202 | 0 | CHCH (E-isomer) | CH₂CH(Me) | CH₂C(Me)₂CH₂ | CN₄H |
| 203 | 0 | O | CH₂CH(Me) | CH₂C(Me)₂CH₂ | CN₄H |
| 204 | 0 | S | CH₂CH(Me) | CH₂C(Me)₂CH₂ | CN₄H |
| 205 | 0 | CH₂O | CH=C(Me) | CH₂C(Me)₂ | CO₂H |
| 206 | 0 | CH₂O | CH=C(Me) | CH₂C(Me)₂CH₂ | CN₄H |
| 207++ | 0 | CH₂O | CH=C(Me) | CH₂C(Me)₂ | CO₂H |

++N-substituent on indole ring is 3-F—C₆H₄—CH₂—

| | X | R⁴W | (CR²R³)ₘ-Z-(CR²R³)ₙ | Q |
|---|---|---|---|---|
| 208 | CH₂O | C₆H₅CO | CH₂C(Me)₂ | CO₂H |
| 209 | CH₂O | C₆H₅S(O)₂ | CH₂C(Me)₂CH₂ | CN₄H |
| 210 | (CH₂)₂ | C₆H₅CH₂ | CH₂C(Me)₂CH₂ | CO₂H |
| 211 | (CH₂)₂ | 3-FC₆H₄CH₂ | CH₂C(Me)₂CH₂ | CO₂H |
| 212 | (CH₂)₂ | 3-FC₆H₄CH₂ | CH₂C(Me)₂CH₂ | CN₄H |
| 213 | (CH₂)₂ | 3-FC₆H₄CH₂ | CH₂C(Me)₂CH₂ | CONHS(O)₂Me |
| 214 | (CH₂)₂ | 4-ClC₆H₄CH₂ | (CH₂)₂OCH(Me) | CO₂H |
| 215 | CH=CH (E-isomer) | 4-ClC₆H₄CH₂ | (CH₂)₂OCH(Et) | CO₂H |
| 216 | CH₂O | 4-ClC₆H₄CH₂ | COC(Me)₂CH₂ | CN₄H |
| 217 | CH₂O | 4-ClC₆H₄CH₂ | CH(OMe)C(Me)₂CH₂ | CN₄H |
| 218 | CH₂O | 4-ClC₆H₄CH₂ (E-isomer) | CH=CHCH₂ | CO₂H |
| 219 | CH₂O | 4-ClC₆H₄CH₂ (E-isomer) | CH=CHCH(Me) | CO₂H |

7. A pharmaceutical composition comprising a therapeutically effective amount of a compound of claim 1 and a pharmaceutically acceptable carrier.

8. The pharmaceutical composition of claim 7 additionally comprising an effective amount of a second active ingredient selected from the group consisting of non-steroidal anti-inflammatory drugs; peripheral analgesic agents; cyclooxygenase inhibitors; leukotriene antagonists; leukotriene biosynthesis inhibitors; $H_1$- or $H_2$-receptor antagonists; antihistaminic agents; prostaglandin antagonists; and ACE antagonists.

9. A pharmaceutical composition according to claim 8, wherein the second active ingredient is a non-steroidal anti-inflammatory drug.

10. A pharmaceutical composition of claim 9, wherein the weight ratio of said compound of claim 1 to said second active ingredient ranges from about 1000:1 to 1:1000.

11. A method of preventing the synthesis, the action, or the release of SRS-A or leukotrienes in a mammal which comprises administering to said mammal an effective amount of a compound of claim 1.

12. The method of claim 11 wherein the mammal is man.

13. A method of treating asthma in a mammal comprising administering to a mammal in need of such treatment a therapeutically effective amount of a compound of claim 1.

14. A method of treating inflammatory diseases of the eye in a mammal which comprises administering to a mammal in need of such treatment a therapeutically effective amount of a compound of claim 1.

15. The method of claim 14 wherein the mammal is man.

* * * * *